US012215326B2

(12) United States Patent
Zhang et al.

(10) Patent No.: US 12,215,326 B2
(45) Date of Patent: Feb. 4, 2025

(54) RNA-TARGETING SYSTEM

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Feng Zhang, Cambridge, MA (US); Patrick Hsu, Cambridge, MA (US); Jonathan S. Gootenberg, Cambridge, MA (US); Aaron Smargon, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/632,067

(22) Filed: Jun. 23, 2017

(65) Prior Publication Data
US 2017/0306335 A1    Oct. 26, 2017

Related U.S. Application Data

(63) Continuation-in-part of application No. PCT/US2015/067151, filed on Dec. 21, 2015.

(60) Provisional application No. 62/096,324, filed on Dec. 23, 2014, provisional application No. 62/098,059, filed on Dec. 30, 2014, provisional application No. 62/181,641, filed on Jun. 18, 2015, provisional application No. 62/181,667, filed on Jun. 18, 2015.

(51) Int. Cl.
| | |
|---|---|
| *C12N 15/63* | (2006.01) |
| *C12N 9/22* | (2006.01) |
| *C12N 15/11* | (2006.01) |
| *C12N 15/115* | (2010.01) |
| *C12N 15/82* | (2006.01) |
| *C12N 15/86* | (2006.01) |

(52) U.S. Cl.
CPC .............. *C12N 15/63* (2013.01); *C12N 9/22* (2013.01); *C12N 15/11* (2013.01); *C12N 15/111* (2013.01); *C12N 15/115* (2013.01); *C12N 15/86* (2013.01); *C12Y 301/21004* (2013.01); *C07K 2319/09* (2013.01); *C12N 2310/10* (2013.01); *C12N 2310/16* (2013.01); *C12N 2310/20* (2017.05); *C12N 2330/51* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 6,603,061 B1 | 8/2003 | Armstrong et al. | |
| 7,868,149 B2 | 1/2011 | Boukharov et al. | |
| 8,507,272 B2 | 8/2013 | Zhang et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 10,544,405 B2* | 1/2020 | Weiss ................. | C12N 15/8216 |
| 11,312,945 B2* | 4/2022 | Weiss ............. | C12Y 301/21004 |
| 2009/0100536 A1 | 4/2009 | Adams et al. | |
| 2011/0059502 A1 | 3/2011 | Chalasani | |
| 2014/0170753 A1 | 6/2014 | Zhang | |
| 2014/0179006 A1 | 6/2014 | Zhang | |
| 2014/0179770 A1* | 6/2014 | Zhang .................... | C12N 15/86 |
| | | | 514/44 R |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |

(Continued)

FOREIGN PATENT DOCUMENTS

| | | |
|---|---|---|
| EP | 2771468 B1 | 2/2015 |
| EP | 2784162 B1 | 4/2015 |

(Continued)

OTHER PUBLICATIONS

Hsu et al Development and Applications of CRISPR-Cas9 for Genome Engineering Cell 157, Jun. 5, 2014 pp. 1292-1278.*
Sampson et al A CRISPR/Cas system mediates bacterial innate immune evasion and virulence | N AT U R E | vol. 4 9 7 | May 9, 2013 pp. 254-258.*
Chu et al.,Increasing the efficiency of homology-directed repair for CRISPR-Cas9-induced precise gene editing in mammalian cells (Nature biotechnology ; May 2015; pp. 543-549).*
Garneau et al The CRISPR/Cas bacterial immune system cleaves bacteriophage and plasmid DNA Nature 2010; pp. 67-71.*

(Continued)

*Primary Examiner* — Maria G Leavitt
(74) *Attorney, Agent, or Firm* — F. Brent Nix, Esq.; Christopher D. Southgate, Esq.; Johnson, Marcou, Isaacs & Nix, LLC

(57) ABSTRACT

The invention provides for systems, methods, and compositions for targeting RNA. In particular, the invention provides a non-naturally occurring or engineered RNA-targeting system comprising an RNA-targeting Cas protein and at least one RNA-targeting guide RNA, wherein said RNA-targeting guide RNA is capable of hybridizing with a target RNA in a cell.

36 Claims, 11 Drawing Sheets

Specification includes a Sequence Listing.

(56) References Cited

U.S. PATENT DOCUMENTS

| | | | |
|---|---|---|---|
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0248702 | A1 | 9/2014 | Zhang et al. |
| 2014/0256046 | A1 | 9/2014 | Zhang et al. |
| 2014/0273231 | A1 | 9/2014 | Zhang et al. |
| 2014/0273232 | A1 | 9/2014 | Zhang et al. |
| 2014/0273234 | A1 | 9/2014 | Zhang et al. |
| 2014/0287938 | A1 | 9/2014 | Zhang et al. |
| 2014/0310830 | A1 | 10/2014 | Zhang et al. |
| 2015/0031134 | A1 | 1/2015 | Zhang et al. |
| 2015/0184139 | A1 | 7/2015 | Zhang et al. |
| 2015/0329875 | A1* | 11/2015 | Gregory ............... C12N 15/90 435/462 |
| 2015/0353905 | A1* | 12/2015 | Weiss ................. C07K 14/195 435/348 |
| 2017/0081674 | A1* | 3/2017 | Beetham ............ C12N 15/8213 |
| 2017/0233703 | A1* | 8/2017 | Xie ....................... C12N 15/90 514/44 R |
| 2018/0044700 | A1* | 2/2018 | Doudna ............... C12Y 301/00 |

FOREIGN PATENT DOCUMENTS

| | | | |
|---|---|---|---|
| EP | 2764103 B1 | | 8/2015 |
| WO | WO 2010/075424 | * | 7/2010 |
| WO | 2014018423 A2 | | 1/2014 |
| WO | 2014093595 A1 | | 6/2014 |
| WO | 2014093622 A2 | | 6/2014 |
| WO | 2014093635 A1 | | 6/2014 |
| WO | 2014093655 A2 | | 6/2014 |
| WO | 2014093661 A2 | | 6/2014 |
| WO | 2014093694 A1 | | 6/2014 |
| WO | 2014093701 A1 | | 6/2014 |
| WO | 2014093709 A1 | | 6/2014 |
| WO | 2014093712 A1 | | 6/2014 |
| WO | 2014093718 A1 | | 6/2014 |
| WO | WO2014113493 | * | 7/2014 |
| WO | 2014204723 A1 | | 12/2014 |
| WO | 2014204724 A1 | | 12/2014 |
| WO | 2014204725 A1 | | 12/2014 |
| WO | 2014204726 A1 | | 12/2014 |
| WO | 2014204727 A1 | | 12/2014 |
| WO | 2014204728 A1 | | 12/2014 |
| WO | 2014204729 A1 | | 12/2014 |
| WO | 2015065964 A1 | | 5/2015 |
| WO | 2015089351 A1 | | 6/2015 |
| WO | 2015089354 A1 | | 6/2015 |
| WO | 2015089364 A1 | | 6/2015 |
| WO | 2015089419 A2 | | 6/2015 |
| WO | 2015089427 A1 | | 6/2015 |
| WO | 2015089462 A1 | | 6/2015 |
| WO | 2015089465 A1 | | 6/2015 |
| WO | 2015089473 A9 | | 6/2015 |
| WO | 2015089486 A2 | | 6/2015 |
| WO | 2016028682 A1 | | 2/2016 |
| WO | 2016049163 A2 | | 3/2016 |
| WO | 2016049258 A2 | | 3/2016 |
| WO | WO 2016049258 | * | 3/2016 |
| WO | 2014/113493 A1 | | 7/2017 |

OTHER PUBLICATIONS

Mali et al CAS9 transcriptional activators for target specificity screening and paired nickases for cooperative genome engineering Nature Biotechnology vol. 31 No. 9 Sep. 2013 pp. 833-840.*

Nishimasu et al., Crystal Structure of Cas9 in Complex with Guide RNA and Target DNA Cell 156, 935-949, Feb. 27, 2014.*

Esvelt et al Orthogonal Cas9 proteins for RNmA-guided gene regulation and editing Nature Methods 2013, pp. 1116-1121.*

Hirano et al., Structure and Engineering of Francisella novicida Cas9 2016, Cell 164, 950-961.*

Nishimasu et al . Supplemental information. Crystal Structure of Cas9 in Complex with Guide RNA and Target DNA vol. 156, Issue 5, Feb. 27, 2014, pp. 935-949.*

Timothy R. Sampson, et al., A CRISPR/Cas System Mediates Bacterial Innate Immune Evasion and Virulence, Nature (Apr. 14, 2013) vol. 497, No. 7448, p. 254-257.

Prashant Mali et al., CAS9 Transcriptional Activators for Target Specificity Screening and Paired Nickases . . . , Nature Biotechnology (2013) vol. 31, No. 9, p. 833-838.

Prashant Mali et al., Supplementary Information: CAS9 Transcriptional Activators for Target Specificity . . . , Nature Biotechnology (2013) vol. 31, No. 9, p. 833-838.

Fu, Y. et al., Targeted Genome Editing in Human Cells Using CRISPR/Cas Nucleases and Truncated Guide RNAsc, (Jan. 1, 2014) The Use of CRISPR/CAS9, ZFNS and Talens. in Generating Site-Specific Genome Alterations, Methods of Enzymology ISSN 1557-7988, vol. 546, p. 21-45.

Krzysztof Chylinski, et al., The tracrRNA and Cas9 Families of Type II CRISPR-Cas Immunity Systems, RNA Biology (May 1, 2013) vol. 10, No. 5, p. 727-737.

Timothy R. Sampson, et al., Supplementary Information: A CRISPR/Cas System Mediates Bacterial Innate Immune Evasion and Virulence, Nature (Apr. 14, 2013) vol. 497, No. 7448, p. 254-257.

Belhaj, K. et al., "Plant genome editing made easy: targeted mutagenesis in model and crop plants using the CRISPR/Cas system", Plant Methods, vol. 9, No. 39, pp. 1-10, Published: Oct. 11, 2013.

Brooks, Christopher et al., "Efficient Gene Editing in Tomato in the First Generation Using the Clustered Regularly Interspaced Short Palindromic Repeats/CRISPR-Associated9 System1", Plant Pysiology, vol. 166, pp. 1292-1297, Nov. 2014.

Shan, Q. et al., "Targeted genome modification of crop plants using a CRISPR-Cas system", Nature Biotechnology, vol. 31, No. 8, pp. 686-688, Aug. 2013.

Feng, Zhengyan et al., "Efficient genome editing in plants using a CRISPR/Cas system", Cell Research, vol. 23, pp. 1229-1232, Published online: Aug. 20, 2013.

Xie, Kabin et al., "RNA-Guided Genome Editing in Plants Using a CRISPR-Cas System", Molecular Plant, vol. 6, No. 6, pp. 1975-1983, Nov. 2013.

Xu, Rongfang et al., "Gene targeting using the Agrobacterium tumefaciens-mediated CRISPR-Cas system in rice", Rice, vol. 7, No. 5, pp. 1-4, 2014.

Zhou, Xiaohong et al., "Exploiting SNPs for biallelic CRISPR mutations in the outcrossing woody perennial *Populus* reveals 4-coumarate: CoA ligase specificity and redundancy", New Phytologist, vol. 208, pp. 298-301, 2015.

Caliando, B.J. et al., "Targeted DNA degradation using a CRISPR device stably carried in the host genome", Nature Communications, l 6:6989, pp. 1-10, Published: May 19, 2015.

Tsai, S.Q. et al., "Dimeric CRISPR RNA-guided FokI nucleases for highly specific genome editing", Nat Biotechnology, vol. 32, No. 6, pp. 569-576, Jun. 2014.

Platt, R.J. et al., "CRISPR-Cas9 Knockin Mice for Genome Editing and Cancer Modeling", Cell, vol. 59, pp. 440-455, Oct. 9, 2014.

Sapranauskas, Rimantas et al., "The *Streptococcus thermophilus* CRISPR/Cas system provides immunity in *Escherichia coli*", Nucleic Acids Research, vol. 39, No. 21, pp. 9275-9282, Published online: Aug. 3, 2011.

Mojica, Francisco J. M. et al., "Biological significance of a family of regularly spaced repeats in the genomes of Archaea, Bacteria and mitochondria", Molecular Microbiology, vol. 36, No. 1, pp. 244-246, 2000.

Van Embden, J. D. A. et al., "Genetic Variation and Evolutionary Origin of the Direct Repeat Locus of Mycobacterium tuberculosis Complex Bacteria", Journal of Bacteriology, vol. 182, No. 9, pp. 2393-2401, Accepted Jan. 26, 2000.

Mojica, F.J.M. et al., "Intervening Sequences of Regularly Spaced Prokaryotic Repeats Derive from Foreign Genetic Elements", Journal of Molecular Evolution, vol. 60, Issue 2, pp. 174-182, Feb. 2005.

Nishimasu, Hiroshi et al., "Crystal Structure of Cas9 in Complex with Guide RNA and Target DNA", Cell, vol. 156, No. 5, pp. 935-949, Feb. 27, 2014.

(56) References Cited

OTHER PUBLICATIONS

Kleinstiver, Benjamin P. et al., "Engineered CRISPR-Cas9 nucleases with altered PAM specificities", Nature, vol. 523, No. 7561, pp. 481-485, Jul. 23, 2015.
Nishimasu, Hiroshi et al., "Crystal Structure of *Staphylococcus aureus* Cas9", Cell, vol. 162, pp. 1113-1126 Aug. 27, 2015.
Bland, Charles et al. "CRISPR Recognition Tool (CRT): a tool for automatic detection of clustered regularly Interspaced palindromic repeats", BMC Bioinformatics, vol. 8, No. 209, pp. 1-8, Published: Jun. 18, 2007.
Cong, Le et al., "Multiplex Genome Engineering Using CRISPR/Cas Systems", Science, vol. 339, No. 6121, pp. 819-823, Feb. 15, 2013.
Jiang, Wenyan et al., "RNA-guided editing of bacterial genomes using Crispr-Cas systems", Nature Biotechnology, vol. 31, No. 3, pp. 233-239, Mar. 2013.
Wang, Haoyi et al., "One-Step Generation of Mice Carrying Mutations in Multiple Genes by CRISPR/Cas-Mediated Genome Engineering", Cell, vol. 153, pp. 1-9, May 9, 2013.
Konermann, Silvana et al., "Optical control of mammalian endogenous transcription and epigenetic states", Nature, vol. 500, pp. 472-478, Aug. 22, 2013.
Ran, F.A. et al., "Double nicking by RNA-guided CRISPR Cas9 for enhanced genome editing specificity", Cell, vol. 154, No. 6, pp. 1-18, Sep. 12, 2013.
Hsu, P.D. et al., "DNA targeting specificity of RNA-guided Cas9 nucleases", Nature Biotechnology, vol. 31, No. 9, pp. 827-834, Sep. 2013.
Ran, F.A. et al., "Genome engineering using the CRISPR-Cas9 system", Nature Protocols, vol. 8, No. 11, pp. 2281-2308, 2013.
Shalem, O. et al., "Genome-Scale CRISPR-Cas9 Knockout Screening in Human Cells", Science, vol. 343, No. 6166, pp. 84-87, Jan. 3, 2014.
Wu, Xuebing et al., "Genome-wide binding of the CRISPR endonuclease cas9 in mammalian cells", Nature Biotechnology, pp. 1-7, Published Online: Apr. 20, 2014.
Hsu, P.D. et al., "Development and Applications of CRISPR-Cas9 for Genome Engineering", Cell, pp. 1262-1278, vol. 157, Jun. 5, 2014.
Wang, Tim et al., "Genetic screens in human cells using the CRISPR/Cas9 system", Science, vol. 343, No. 6166, pp. 80-84, Jan. 3, 2014.
Doench, John G et al., "Rational design of highly active sgRNAs for CrIsPr-Cas9-mediated gene inactivation", Nature Biotechnology, pp. 1-6, Published Online: Sep. 3, 2014.
Swiech, Lukasz et al., "In vivo interrogation of gene function in the mammalian brain using CrIsPr-Cas9", Nature Biotechnology, pp. 1-9, Published Online: Sep. 3, 2014.
Konermann, Silvana et al., "Genome-scale transcriptional activation by an engineered CRISPR-Cas9 complex", Nature, vol. 517, No. 7536, pp. 583-588, Jan. 29, 2015.
Zetche, Bernd et al., "A Split Cas9 Architecture for Inducible Genome Editing and Transcription Modulation", Nature Biotechnology, vol. 33, No. 2, pp. 139-142, Feb. 2015.
Chen, Sidi et al., "Genome-wide CRISPR screen in a mouse model of tumor growth and metastasis", Cell, vol. 160, No. 6, pp. 1246-1260, Mar. 12, 2015.
Ran, F.A. et al., "In vivo genome editing using *Staphylococcus aureus* Cas9", Nature, vol. 520, pp. 186-193, Apr. 9, 2015.
Shalem, O. et al., "High-throughput functional genomics using CRISPR-Cas9", Nature Reviews, vol. 16, pp. 299-311, May 2015.
Xu, Han et al., "Sequence determinants of improved CRISPR sgRNA design", Genome Research, vol. 25, pp. 1147-1157, accepted in revised form Jun. 10, 2015.
Parnas, Oren et al., "A genome-wide CRISPR screen in primary immune cells to dissect regulatory networks", Cell, vol. 162, No. 3, pp. 675-686, Jul. 30, 2015.
Ramanan, Vyas et al., "CRISPR/Cas9 cleavage of viral DNA efficiently suppresses hepatitis B virus", Nature, Scientific Reports, 5:10833, pp. 1-9, Published: Jun. 2, 2015.
Canver, M.C. et al., "BCL11A enhancer dissection by Cas9-mediated in situ saturating mutagenesis", Nature, vol. 527, pp. 192-197, Nov. 12, 2015.
Zetche, Bernd et al., "Cpf1 is a single RNA-guided endonuclease of a Class 2 CRISPR-Cas system", Cell, vol. 163, No. 3, pp. 759-771, Oct. 22, 2015.
Shmakov, Sergey et al., "Discovery and Functional Characterization of Diverse Class 2 CRISPR-Cas Systems", Molecular Cell, vol. 60, pp. 1-13, Nov. 5, 2015.
Slaymaker, I.M. et al., "Rationally engineered Cas9 nucleases with improved specificity", Science, pp. 1-7, Dec. 1, 2015.
Sampson, T.R. et al., "A CRISPR-CAS System Mediates Bacterial Innate Immune Evasion and Virulence", Nature, vol. 497, No. 7448, pp. 254-257, May 9, 2013.
Jansen, R. et al., "Identification of genes that are associated with DNA repeats in prokaryotes", Molecular Microbiology, vol. 43, Issue 6, pp. 1-17, Published: Apr. 25, 2002.
Panda G, Ray A. Comparative structural and dynamics study of free and gRNA-bound FnCas9 and SpCas9 proteins. Comput Struct Biotechnol J. Aug. 4, 2022;20:4172-4184.
Rice P, Longden I, Bleasby A. EMBOSS: the European Molecular Biology Open Software Suite. Trends Genet. Jun. 2000;16(6):276-7.

\* cited by examiner ctgaacatcacactataaagtaatcaagcttgcattgtctaacgtagtttaccaataatattcagcaactgaaacttaattaattttgtaaattattcctaaaagtttctagttggacacattgtatcaataaataatcacgaaacagtttacagcaaaatgttgatcttcaacatactacc gattttgtagtg gatattttcattagttcgaacggtaacagattgtcatcgtgttattaagttctgttgacttgaattaataaacattcaattaaggatttcaaagatcaacctgtgtaacagtgttattatagtgtttgttttgcaaaagtcgttttacaacagagttgtatgatgg ⟪ Sca by seq ⟫ aaagcattcaataataataaaaataagtaggtctaaaagtgaattttctagctacttaaacaacagtacataccaaatatctaacaactgaaacttacagctaatcttttttcatttgctttcataattcaacatagttatttaataagtctagtttactaaaacatcatttaaaataattt tttcgtaagttattttattttttattcatccagattttcacttaaagatcgatgataaatttgattgttcatgtatggttgacttgaatgtgattagaaaagtaaacgaaactattaagagatgtatcaaataattatcagatcaaatgatttttgggtaaattttattaaa ⟪ Sca by seq ⟫

FIG. 9B

SEQUENCE LISTING

```
<160> NUMBER OF SEQ ID NOS: 36

<210> SEQ ID NO 1
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 1
nnnnnnnnnn nnnnnnnnnn gtttttgtac tctcaagatt tagaaataaa tcttgcagaa      60
gctacaaaga taaggcttca tgccgaaatc aacaccctgt cattttatgg cagggtgttt     120
tcgttattta atttttt                                                    137

<210> SEQ ID NO 2
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
```

<221> NAME/KEY: modified_base
<222> LOCATION: (1)..(20)
<223> OTHER INFORMATION: a, c, t, g, unknown or other

<400> SEQUENCE: 2
nnnnnnnnnn nnnnnnnnnn gtttttgtac tctcagaaat gcagaagcta caaagataag   60
gcttcatgcc gaaatcaaca ccctgtcatt ttatggcagg gtgttttcgt tatttaattt  120
ttt                                                                123

<210> SEQ ID NO 3
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 3
nnnnnnnnnn nnnnnnnnnn gtttttgtac tctcagaaat gcagaagcta caaagataag   60
gcttcatgcc gaaatcaaca ccctgtcatt ttatggcagg gtgttttttt             110

<210> SEQ ID NO 4
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 4
nnnnnnnnnn nnnnnnnnnn gttttagagc tagaaatagc aagttaaaat aaggctagtc   60
cgttatcaac ttgaaaaagt ggcaccgagt cggtgctttt tt                     102

<210> SEQ ID NO 5
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 5
nnnnnnnnnn nnnnnnnnnn gttttagagc tagaaatagc aagttaaaat aaggctagtc   60
cgttatcaac ttgaaaaagt gttttttt                                      88

<210> SEQ ID NO 6
<211> LENGTH: 76
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 6
nnnnnnnnnn nnnnnnnnnn gttttagagc tagaaatagc aagttaaaat aaggctagtc    60
cgttatcatt tttttt                                                    76

<210> SEQ ID NO 7
<211> LENGTH: 7
<212> TYPE: PRT
<213> ORGANISM: Simian virus 40

<400> SEQUENCE: 7

Pro Lys Lys Lys Arg Lys Val
1               5

<210> SEQ ID NO 8
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 8

Lys Arg Pro Ala Ala Thr Lys Lys Ala Gly Gln Ala Lys Lys Lys Lys
1               5                   10                  15

<210> SEQ ID NO 9
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 9

Pro Ala Ala Lys Arg Val Lys Leu Asp
1               5

<210> SEQ ID NO 10
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 10

Arg Gln Arg Arg Asn Glu Leu Lys Arg Ser Pro
1               5                   10

<210> SEQ ID NO 11
<211> LENGTH: 38
<212> TYPE: PRT
<213> ORGANISM: Homo sapiens

<400> SEQUENCE: 11

Asn Gln Ser Ser Asn Phe Gly Pro Met Lys Gly Gly Asn Phe Gly Gly
1               5                   10                  15
```

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 12
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 12

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 13
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 13

Val Ser Arg Lys Arg Pro Arg Pro
1               5

<210> SEQ ID NO 14
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 14

Pro Pro Lys Lys Ala Arg Glu Asp
1               5

<210> SEQ ID NO 15
<211> LENGTH: 8
<212> TYPE: PRT
<213> ORGANISM: Homo sapiens

<400> SEQUENCE: 15

Pro Gln Pro Lys Lys Lys Pro Leu
1               5

<210> SEQ ID NO 16
<211> LENGTH: 12
<212> TYPE: PRT
<213> ORGANISM: Mus musculus

<400> SEQUENCE: 16

Ser Ala Leu Ile Lys Lys Lys Lys Lys Met Ala Pro
1               5                   10

<210> SEQ ID NO 17
<211> LENGTH: 5
<212> TYPE: PRT
<213> ORGANISM: Influenza virus

<400> SEQUENCE: 17

Asp Arg Leu Arg Arg
1               5

<210> SEQ ID NO 18
<211> LENGTH: 7
<212> TYPE: PRT
<213> ORGANISM: Influenza virus

<400> SEQUENCE: 18

Pro Lys Gln Lys Lys Arg Lys
1               5

<210> SEQ ID NO 19
<211> LENGTH: 10
<212> TYPE: PRT
<213> ORGANISM: Hepatitis delta virus

<400> SEQUENCE: 19

Arg Lys Leu Lys Lys Lys Ile Lys Lys Leu
1               5                   10

<210> SEQ ID NO 20
<211> LENGTH: 10
<212> TYPE: PRT
<213> ORGANISM: Mus musculus

<400> SEQUENCE: 20

Arg Glu Lys Lys Lys Phe Leu Lys Arg Arg
1               5                   10

<210> SEQ ID NO 21
<211> LENGTH: 20
<212> TYPE: PRT
<213> ORGANISM: Homo sapiens

<400> SEQUENCE: 21

Lys Arg Lys Gly Asp Glu Val Asp Gly Val Asp Glu Val Ala Lys Lys
1               5                   10                  15

Lys Ser Lys Lys
            20

<210> SEQ ID NO 22
<211> LENGTH: 17
<212> TYPE: PRT
<213> ORGANISM: Homo sapiens

<400> SEQUENCE: 22

Arg Lys Cys Leu Gln Ala Gly Met Asn Leu Glu Ala Arg Lys Thr Lys
1               5                   10                  15

Lys

<210> SEQ ID NO 23
<211> LENGTH: 4
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 23

Gly Gly Gly Ser
1

<210> SEQ ID NO 24
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 26
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 27
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30
```

Gly Gly Ser Gly Gly Gly Ser Gly Gly Gly Ser Gly Gly Gly
            35                  40                  45

Gly Ser Gly Gly Gly Gly Ser Gly Gly Gly Ser
    50                  55                  60

<210> SEQ ID NO 28
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Gly Gly Ser Gly Gly Gly Ser Gly Gly Gly Ser
1               5                   10

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Glu Ala Ala Ala Lys Ala
1               5

<210> SEQ ID NO 30
<211> LENGTH: 130
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
ugcccugacu gcuucguggu agauaugcuu gcuuuuguua auugguugua ggggauuuau     60
ugaaaaauau gaaauauggu aauuugauga ugaugacaaa aaagaagcuu uugaucgggg    120
augguaacaa                                                          130

<210> SEQ ID NO 31
<211> LENGTH: 111
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
guaccaaaua auuaaugcuc uguaaucauu uaaaaguauu uugaacggac cucuguuuga     60
cacgucugaa uaacuaaaaa gcaaaaauuu gccaccuaag uggcuuuuuu u             111

<210> SEQ ID NO 32
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 32
guuguuagau uauuugguau guacuugugu uaguuuaaag uagcuagaaa auucacuuuu    60
agaccuacuu auuuuu    76

<210> SEQ ID NO 33
<211> LENGTH: 376
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
ctgaaacatc acactataaa agtaatcaag cttgccattg tctaacagta gtttaccaaa    60
taattcagca actgaaactt aattaatttt gtaaattatt cctaaaagtt tctagttgga   120
cacattgtat caaataatat aatcacgaaa acagttttac agcaaaatgt tgatctcaac   180
atactaccaa agcattcaaa taataaaaat aagtaggtct aaaagtgaat tttctagcta   240
ctttaaacta acacaagtac ataccaaata atctaacaac tgaaacttac agctaatctt   300
tttcatttgc tttgataatt ctaacatagt ttattaaata gtctagttta ctaaaaaact   360
catttaaaaa taattt   376

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gtctaagaac tttaaataat    20

<210> SEQ ID NO 35
<211> LENGTH: 156
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
aaataataaa aataagtagg tctaaaagtg aattttctag ctactttaaa ctaacacaag    60
tacataccaa ataatctaac aactgaaact tacagctaat cttttcatt tgctttgata   120 attctaacat agtttattaa atagtctagt ttacta    156

<210> SEQ ID NO 36
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 36

```
aaaaaaagcc acttaggtgg caaatttttg cttttttagtt attcagacgt gtcaaacaga      60
ggtccgttca aaatactttt aaatgattac agagcattaa ttatttggt               109
```

RNA-TARGETING SYSTEM

RELATED APPLICATIONS AND INCORPORATION BY REFERENCE

This application is a continuation-in-part of International patent application Serial No. PCT/US2015/067151 filed Dec. 21, 2015 and published as PCT Publication No. WO2016/106236 on Jun. 30, 2016 and which claims the benefit of and priority from U.S. application Ser. No. 62/096,324, filed Dec. 23, 2014, U.S. application Ser. No. 62/098,059, filed Dec. 30, 2014, U.S. application Ser. No. 62/181,641, filed Jun. 18, 2015 and U.S. application Ser. No. 62/181,667, filed Jun. 18, 2015.

The foregoing application, and all documents cited therein or during their prosecution ("appln. Cited documents") and all documents cited or referenced in the appln. cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant number MH100706, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 23, 2016, is named 47627.99.2009_SL.txt and is 12 bytes in size.

FIELD OF THE INVENTION

The present invention generally relates to systems, methods and compositions used for the control of gene expression involving sequence targeting, such as perturbation of gene transcripts or RNA editing, that may use vector systems related to Clustered Regularly Interspaced Short Palindromic Repeats (CRISPR) and components thereof.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new RNA targeting technologies that enable diverse applications, such as RNA knockdown, translational regulation or transcript splicing, trafficking, and visualization. Simple and scalable tools to study and manipulate RNA lag significantly behind their DNA counterparts. Existing RNA interference technologies, which enable cleavage or inhibition of desired transcripts, have significant off-target effects and remain challenging engineering targets due to their key role in endogenous processes. One of the key limitations in RNA engineering has been the lack of RNA-binding domains that can be easily retargeted. The MS2 RNA-binding domain, for example, recognizes an invariable 21 nt RNA sequence, requiring genomic modification to tag a desired transcript. While *pumilio* homology domains possess modular repeats similar to TAL effectors, with each protein module recognizing a separate RNA base, they recognize only 8 nucleotides of RNA and have proved difficult to reprogram in practice. Transcriptional activation and repression can also be achieved through Cas9-mediated recruitment of protein effectors. However, such modes of transcriptional control only allow coarse gene regulation via DNA promoter or enhancer regions of interest. Hence, there remains a need for RNA engineering technologies that are affordable, easy to set up, scalable, and amenable to targeting multiple RNA targets.

Sampson et al. (2013, Nature 497:254-258) describe a natural CRISPR-Cas-mediated system that represses an endogenous transcript in *Francisella novicida*. This system uses the Cas protein Cas9 of *Francisella novicida*, a unique, small, CRISPR/Cas-associated RNA (scaRNA), and trans-activating crRNA (tracrRNA) to repress an endogenous transcript encoding a bacterial lipoprotein. The system has not been transferred yet into heterologous cells.

Citation or identification of any document in this application is not an admission that such document is available as prior art to the present invention.

SUMMARY OF THE INVENTION

There exists a pressing need for alternative and robust systems and techniques for RNA targeting with a wide array of applications. This invention addresses this need and provides related advantages. The targeting system described herein has dual functionality as it can target both DNA and RNA depending on the targeting guide selected. Aspects of the RNA-targeting system described herein may be modified accordingly for use as a DNA-targeting system. The RNA-targeting system also referred to as RNA-targeting CRISPR/Cas or the CRISPR-Cas RNA-targeting system of the present application which is based on an RT (RNA-targeting) type II Cas protein (e.g. the Cas9 from the bacterial pathogen *Francisella novicida*) does not require the generation of customized proteins to target specific RNA sequences but rather a single Cas enzyme can be programmed by an RNA molecule to recognize a specific RNA target, in other words the Cas enzyme can be recruited to a specific RNA target using said RNA molecule. Adding the novel RNA-targeting system of the present application to the repertoire of RNA targeting technologies may transform the study and perturbation or editing of RNA through direct RNA detection, analysis and manipulation. To utilize the RNA-targeting system of the present application effectively for RNA targeting without deleterious effects, it is critical to understand aspects of engineering and optimization of these RNA targeting tools.

The RNA-targeting systems, the vector systems, the vectors and the compositions described herein may be used in various RNA-targeting applications, altering or modifying synthesis of a gene product, such as a protein, RNA cleavage, RNA editing, RNA splicing; trafficking of target RNA, tracing of target RNA, isolation of target RNA, visualization of target RNA, etc.

Accordingly, in a further aspect, the invention provides a method for altering, modifying or modulating synthesis of a gene product, in particular a protein. The said method may comprise introducing into a cell containing and expressing an RNA molecule encoding the gene product, in particular the protein, an engineered or non-naturally occurring CRISPR-Cas RNA-targeting system as taught herein comprising an RNA-targeting Cas protein (such as e.g. the Cas9 from the bacterial pathogen *Francisella novicida*) and an RNA-targeting guide RNA that targets the RNA molecule encoding the gene product, wherein the RNA-targeting guide RNA comprises an scaRNA sequence and a tracrRNA sequence, which scaRNA sequence and tracrRNA sequence are capable of at least partially hybridizing, whereby synthesis of the gene product, in particular the protein, is altered; and, wherein the RNA-targeting Cas protein and the RNA-targeting guide RNA do not naturally occur together. In a preferred embodiment, said method comprises introducing into a cell containing an RNA molecule encoding said gene product, in particular said protein, a vector system comprising one or more vectors comprising:
  a) a first regulatory element operably linked to a polynucleotide sequence encoding an RNA-targeting guide RNA, wherein said RNA-targeting guide RNA is capable of hybridizing with said target RNA, wherein said RNA-targeting guide RNA comprises:
    (i) a small CRISPR/Cas system associated RNA (scaRNA) sequence, and
    (ii) a trans-activating CRISPR/Cas system RNA (tracrRNA) sequence, wherein said scaRNA and said tracrRNA are capable of at least partially hybridizing, and
  b) a second regulatory element operably linked to a polynucleotide sequence encoding an RNA-targeting Cas protein,
  wherein components (a) and (b) are located on the same or different vectors of the system; whereby synthesis of said gene product, in particular said protein, is modulated. In a preferred embodiment the cell is a eukaryotic cell, and in more preferred embodiment the eukaryotic cell is a mammalian cell, and in an even more preferred embodiment the mammalian cell is a human cell. In an embodiment of the invention, the synthesis of the gene product is decreased or suppressed. In a further embodiment of the invention, the synthesis of the gene product is suppressed by knock-down of the RNA molecule encoding the gene product. In another embodiment of the invention, the synthesis of the gene product is increased. In an embodiment of the invention, the synthesis of the gene product, in particular the protein, is modulated by editing the RNA molecule encoding the gene product, e.g. the protein. In an embodiment of the invention, the synthesis of the gene product, in particular the protein, is modulated by splicing the RNA molecule encoding the gene product, e.g. the protein.

In an aspect, the invention provides a method for targeting RNA. Said method may comprise introducing into a cell containing a target RNA, a vector system as taught herein comprising one or more vectors comprising:
  a) a first regulatory element operably linked to a polynucleotide sequence encoding an RNA-targeting guide RNA, wherein said RNA-targeting guide RNA is capable of hybridizing with said target RNA, wherein said RNA-targeting guide RNA comprises:
    (i) a small CRISPR/Cas system associated RNA (scaRNA) sequence, and
    (ii) a trans-activating CRISPR/Cas system RNA (tracrRNA) sequence, wherein said scaRNA and said tracrRNA are capable of at least partially hybridizing, and
  b) a second regulatory element operably linked to a polynucleotide sequence encoding an RNA-targeting Cas protein, wherein components (a) and (b) are located on the same or different vectors of the system; whereby said RNA-targeting guide RNA directs said RNA-targeting Cas protein to said target RNA.

Also disclosed herein is a method for tracing a target RNA into a cell comprising:
  introducing into the cell containing the target RNA a non-naturally occurring or engineered vector system comprising one or more vectors comprising:
    a) a first regulatory element operably linked to a polynucleotide sequence encoding an RNA-targeting guide RNA, wherein the RNA-targeting guide RNA is capable of hybridizing with the target RNA, wherein the RNA-targeting guide RNA comprises:
      (i) a small CRISPR/Cas system associated RNA (scaRNA) sequence, and
      (ii) a trans-activating CRISPR/Cas system RNA (tracrRNA) sequence, wherein the scaRNA and the tracrRNA are capable of at least partially hybridizing, and
    b) a second regulatory element operably linked to a polynucleotide sequence encoding an RNA-targeting Cas protein, wherein the RNA-targeting Cas protein is fused to an identification tag, wherein components (a) and (b) are located on the same or different vectors of the system, and
  visualizing the identification tag.

Further disclosed herein is a method of isolating a target RNA from a cell comprising:
  introducing into a cell containing the target RNA a non-naturally occurring or engineered vector system comprising one or more vectors comprising:
    a) a first regulatory element operably linked to a polynucleotide sequence encoding an RNA-targeting guide RNA, wherein the RNA-targeting guide RNA is capable of hybridizing with the target RNA, wherein the RNA-targeting guide RNA comprises:
      (i) a small CRISPR/Cas system associated RNA (scaRNA) sequence, and
      (ii) a trans-activating CRISPR/Cas system RNA (tracrRNA) sequence, wherein the scaRNA and the tracrRNA are capable of at least partially hybridizing, and
    b) a second regulatory element operably linked to a polynucleotide sequence encoding an RNA-targeting Cas protein, wherein the RNA-targeting Cas protein is fused to a tag or associated with a bead, wherein components (a) and (b) are located on the same or different vectors of the system, and separating the target RNA from the cell using the tag or the bead.

In particular, an object of the current invention is to further enhance the specificity of RNA targeting (RT) type II Cas system of the present invention given individual guide RNAs through thermodynamic tuning of the binding specificity of the guide RNA to target RNA.

In one aspect, the invention provides an engineered, non-naturally occurring CRISPR-Cas RNA-targeting system comprising an RT type II Cas protein and an RNA-targeting guide RNA that targets an RNA molecule for transcribing a gene product in a cell, whereby the guide RNA targets the RNA molecule transcribing the gene product and the Cas protein binds to and optionally cleaves the RNA molecule encoding the gene product, whereby expression of the gene product is altered or modulated; and, wherein the Cas protein and the guide RNA do not naturally occur together. The invention comprehends the RNA-targeting guide RNA which optionally comprises a guide sequence fused to a tracr sequence. In an embodiment of the invention the Cas protein is a type II CRISPR-Cas protein having RNA targeting properties and in a preferred embodiment the Cas protein is a Cas9 protein e.g. from the bacterial pathogen *Francisella novicida* or orthologs or homologs or fragments thereof having similar RNA targeting properties. The invention further comprehends the Cas protein to be used according to the invention being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to an RNA-targeting guide RNA that targets an RNA molecule encoding a gene product and a second regulatory element operably linked to an RNA-targeting Cas protein. Components (a) and (b) may be located on same or different vectors of the system. The RNA-targeting guide RNA targets the RNA molecule encoding the gene product in a cell and the RNA-targeting Cas protein binds to and optionally cleaves the RNA molecule encoding the gene product, whereby expression of the gene product is altered; and the RNA-targeting Cas protein and the RNA-targeting guide RNA do not naturally occur together. In particular embodiments, the invention comprehends the RNA-targeting guide RNA to comprise a small CRISPR/Cas system associated RNA (scaRNA) sequence fused to a tracr sequence. In particular embodiments, the RNA-targeting guide RNA comprises a guide (sequence directing recognition of the target RNA), a tracr mate and a tracr RNA sequence, wherein the tracr mate hybridizes with the tracr RNA. In an embodiment of the invention the RNA-targeting Cas protein is an RT type II CRISPR-Cas protein and in a preferred embodiment the Cas protein is a Cas9 protein such as FnCas9 protein. The invention further comprehends the Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the RNA-targeting system comprises: (a) a first regulatory element operably linked to a tracr mate sequence and one or more insertion sites for inserting one or more guide sequences upstream of the tracr mate sequence, wherein when expressed, the guide sequence directs sequence-specific binding of an RNA-targeting CRISPR complex to a target sequence in a eukaryotic cell, wherein the RNA-targeting CRISPR complex comprises an RNA-targeting type II Cas enzyme complexed with (1) the guide sequence that is hybridized to the target sequence, and (2) the tracr mate sequence that is hybridized to the tracr sequence; and (b) a second regulatory element operably linked to an enzyme-coding sequence encoding said RNA-targeting type II Cas enzyme comprising a nuclear localization sequence; wherein components (a) and (b) are located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of an RNA-targeting CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in MATLAB, Bowtie, Geneious, Biopython and SeqMan. In some embodiments, the RNA-targeting CRISPR complex comprises one or more nuclear localization sequences of sufficient strength to drive accumulation of said RNA-targeting CRISPR complex in a detectable amount in the nucleus of a eukaryotic cell. Without wishing to be bound by theory, it is believed that a nuclear localization sequence is not necessary for RNA-targeting CRISPR complex activity in eukaryotes, but that including such sequences may enhance activity of the system especially as to targeting RNA molecules in the nucleus. In some embodiments, the RNA-targeting enzyme is a type II Cas system enzyme. In some embodiments, the CRISPR enzyme is a Cas9 enzyme. In some embodiments, the Cas9 enzyme is *Francisella novicida* Cas9, (Fn) and may include mutated Cas9 derived from these organisms. The enzyme may be an RT (Fn) Cas9 homolog or ortholog. In some embodiments, the CRISPR enzyme is codon-optimized for expression in a eukaryotic cell. In some embodiments, the CRISPR enzyme directs cleavage of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U 5' segment in LTR of HTLV-I (Mol. Cell. Biol., Vol. 8 (1), p. 466-472, 1988); SV40 enhancer; and the intron sequence between exons 2 and 3 of rabbit B-globin (Proc. Natl. Acad. Sci. USA., Vol. 78 (3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In one aspect, the invention provides a vector comprising a regulatory element operably linked to an enzyme-coding sequence encoding a Type II RT Cas CRISPR enzyme. In some embodiments, said regulatory element drives transcription of the CRISPR enzyme in a eukaryotic cell such that said RNA-targeting enzyme accumulates in a detectable amount in the nucleus of the eukaryotic cell. In some embodiments, the regulatory element is a polymerase II promoter. In some embodiments, the RNA-targeting enzyme is a type II CRISPR system enzyme. In some embodiments, the CRISPR enzyme is a Cas9 enzyme. In some embodiments, the Cas9 enzyme is *Francisella novicida* Cas9 (FnCas9), and may include mutated Cas9 derived from these organisms. In some embodiments, the RNA targeting enzyme is codon-optimized for expression in a eukaryotic cell. In some embodiments, the RNA targeting enzyme directs cleavage of one or two strands at the location of the target sequence. In some embodiments, the RNA targeting enzyme lacks DNA strand cleavage activity.

The RNA-targeting enzyme may be an RNA targeting Cas9 homolog or ortholog, particularly of a *Francisella novicida* Cas9 enzyme. In some embodiments, the CRISPR enzyme lacks the ability to cleave one or more strands of a target sequence to which it binds.

In one aspect, the invention provides a eukaryotic host cell comprising (a) a first regulatory element operably linked to an RNA-targeting guide sequence comprising one or more insertion sites for inserting one or more guide sequences, wherein when expressed, the guide sequence directs sequence-specific binding of an RNA-targeting complex to an RNA target sequence in a eukaryotic cell, wherein the RNA-targeting complex comprises an RNA-targeting type II Cas enzyme complexed with (1) the RNA-targeting guide RNA. In further particular embodiments, the RNA-targeting complex may comprise (1) the guide sequence of the RNA-targeting guide RNA that is hybridized to the target sequence, and (2) the tracr mate sequence that is hybridized to the tracr sequence; and/or (b) a second regulatory element operably linked to an enzyme-coding sequence encoding said Type II RT Cas enzyme. In some embodiments, the host cell comprises components (a) and (b). In some embodiments, component (a), component (b), or components (a) and (b) are stably integrated into a genome of the host eukaryotic cell. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different RNA target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the RT-type II Cas enzyme comprises one or more nuclear localization sequences of sufficient strength to drive accumulation of said CRISPR enzyme in a detectable amount of a eukaryotic cell. The CRISPR enzyme used according to the invention is a type II RT Cas CRISPR system enzyme. In some embodiments, the CRISPR enzyme is a Cas9 enzyme. In some embodiments, the Cas9 enzyme is a *Francisella novicida* Type II RT Cas9, and may include mutated Cas9 derived from these organisms. The enzyme may be an RT Cas9 homolog or ortholog. In some embodiments, the CRISPR enzyme is codon-optimized for expression in a eukaryotic cell. In some embodiments, the RNA-targeting CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

With respect to use of the CRISPR-Cas system generally, mention is made of the documents, including patent applications, patents, and patent publications cited throughout this disclosure as embodiments of the invention can be used as in those documents. CRISPR-Cas system(s) (e.g., single or multiplexed) can be used in conjunction with recent advances in crop genomics. Such CRISPR-Cas system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas system(s) can be used with regard to plants in Site-Directed Integration (SDI) or Gene Editing (GE) or any Near Reverse Breeding (NRB) or Reverse Breeding (RB) techniques. With respect to use of the CRISPR-Cas system in plants, mention is made of the University of Arizona website "CRISPR-PLANT" (http://www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi: 10.1186/1746-4811-9-39); Brooks, "Efficient gene editing in tomato in the first generation using the CRISPR/Cas9 system," Plant Physiology September 2014 U.S. Plant Pat. No. 114,247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi: 10.1038/cr.2013.114; published online 20 Aug. 2013; Xie, "RNA-guided genome editing in plants using a CRISPR-Cas system," Mol Plant. 2013 November;6 (6): 1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061-*Agrobacterium*-Mediated Plant Transformation Method; U.S. Pat. No. 7,868,149-Plant Genome Sequences and Uses Thereof and US 2009/0100536-Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13 (2): 85-96; each of which is incorporated by reference herein including as to how herein embodiments may be used as to plants. Accordingly, reference herein to animal cells may also apply, mutatis mutandis, to plant cells unless otherwise apparent.

In one aspect, the invention provides a kit comprising one or more of the components described herein. In some embodiments, the kit comprises a vector system and instructions for using the kit. In some embodiments, the vector system comprises one or more of an RNA-targeting type II Cas enzyme and an RNA targeting guide RNA, wherein the RNA-targeting guide RNA comprises (i) a small CRISPR/Cas system associated RNA (scaRNA) sequence, and (ii) a trans-activating CRISPR/Cas system RNA (tracrRNA) sequence, wherein said scaRNA and said tracrRNA are capable of at least partially hybridizing. In particular embodiments, the kit comprises a vector system comprising (a) a first regulatory element operably linked to a tracr mate sequence and one or more insertion sites for inserting one or more guide sequences upstream of the tracr mate sequence, wherein when expressed, the guide sequence directs sequence-specific binding of an RNA-targeting CRISPR complex to an RNA target sequence in a eukaryotic cell, wherein the RNA-targeting CRISPR complex comprises a Type II RT Cas CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the kit comprises components (a) and (b) located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of an RNA-targeting CRISPR complex to a different target RNA sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the RNA-targeting enzyme comprises one or more nuclear localization sequences of sufficient strength to drive accumulation of said enzyme in a detectable amount in the nucleus of a eukaryotic cell. In some embodiments, the RNA-targeting enzyme is a type II CRISPR system enzyme. In some embodiments, the RNA-targeting enzyme is a Cas9 enzyme. In some embodiments, the Cas9 enzyme is *Francisella novicida* Type II RT Cas9, and may include mutated Cas9 derived from this organism. The enzyme may be a Cas9 homolog or ortholog. In some embodiments, the CRISPR enzyme is codon-optimized for expression in a eukaryotic cell. In some embodiments, the RNA-targeting enzyme lacks DNA strand cleavage activity. In some embodiments the RNA-targeting enzyme lacks RNA cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modulating synthesis of protein in a eukaryotic cell. In some embodiments, the method comprises allowing a CRISPR complex to bind to the target RNA to effect cleavage of said target RNA thereby modifying the transcription of a protein translated from said RNA, wherein the RNA-targeting complex comprises an RNA-targeting type II Cas enzyme complexed with an RNA-targeting guide RNA hybridized to a target sequence. In particular embodiments, the RNA-targeting complex comprises an RNA-targeting type II Cas enyme complexed with a guide sequence hybridized to a target sequence within said target RNA, wherein said guide sequence is linked to a tracr mate sequence which in turn hybridizes to a tracr sequence. In some embodiments, said RNA-targeting enzyme cleaves said target RNA. In some embodiments, said cleavage results in decreased transcription of a target gene. In some embodiments, the method further comprises editing said RNA, wherein said editing results in a mutation comprising an insertion, deletion, or substitution of one or more nucleotides of said target RNA. In some embodiments, said editing results in one or more amino acid changes in a protein translated from the RNA target sequence. In some embodiments, the method further comprises delivering one or more vectors to said eukaryotic cell, wherein the one or more vectors drive expression of one or more of: the RNA-targeting type II Cas enzyme and the RNA-targeting guide RNA. In further embodiments the vectors drive expression of the RNA-targeting type II Cas enzyme the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing an RNA-targeting complex to bind to the RNA corresponding to said polynucleotide such that said binding results in increased or decreased expression of said polynucleotide; wherein the RNA-targeting complex comprises an RNA-targeting type II Cas enzyme complexed with an RNA-targeting guide RNA hybridized to a target RNA sequence corresponding to said polynucleotide. In particular embodiments, the RNA-targeting complex comprises an RNA-targeting type II Cas enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the RNA-targeting enzyme and the RNA-targeting guide RNA. More particularly the one or more vectors drive expression of one or more of, the guide sequence linked to the tracr mate sequence, and the tracr sequence.

In one aspect, the invention provides a method of generating a model eukaryotic cell comprising a modified transcript of a disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: an RNA-targeting type II Cas enzyme and an RNA-targeting guide RNA. In particular embodiments, the one or more vectors drive expression of one or more of an RNA targeting enzyme, a guide sequence linked to a tracr mate sequence, and a tracr sequence; the method may further comprise (b) allowing an RNA-targeting complex to bind to a target RNA to effect cleavage of or binding to the target RNA of said disease gene, wherein the RNA-targeting complex comprises the RNA-targeting enzyme complexed with the RNA-targeting guide RNA hybridized to the target sequence. In particular embodiments, the RNA-targeting complex comprises the RNA-targeting enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease transcript. In some embodiments, said cleavage or binding results in decreased translation of a target RNA. In some embodiments, this results in a mutation comprising an insertion, deletion, or substitution of one or more nucleotides of said target RNA. In some embodiments, said mutation results in one or more amino acid changes in a protein transcription from an RNA comprising the target sequence.

In one aspect, the invention provides a method for developing a biologically active agent that modulates a cell signaling event associated with a disease RNA. In some embodiments, a disease RNA is any RNA associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease RNA, thereby developing said biologically active agent that modulates said cell signaling event associated with said disease RNA.

In one aspect, the invention provides a recombinant polynucleotide comprising a sequence corresponding to an RNA-targeting guide RNA. In particular embodiments, the RNA-targeting guide RNA comprises a guide sequence upstream of a tracr mate sequence, wherein the guide sequence when expressed directs sequence-specific binding of an RNA-targeting complex to a corresponding target sequence present in a eukaryotic cell. In some embodiments, the target sequence is a viral sequence present in a eukaryotic cell. In some embodiments, the target RNA sequence is a proto-oncogene RNA or an oncogene RNA.

In one aspect the invention provides for a method of selecting one or more cell(s) by introducing one or more modifications in the RNA in the one or more cell(s), the method comprising: introducing one or more vectors into the cell(s), wherein the one or more vectors drive expression of one or more of: a CRISPR enzyme, a guide sequence linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more cell(s) in which one or more mutations have been introduced to be selected. In a preferred embodiment, the CRISPR enzyme is Cas9. In another aspect of the invention the cell to be selected may be a eukaryotic cell. Aspects of the invention allow for selection of specific cells without requiring a selection marker or a two-step process that may include a counter-selection system. The cell(s) may be prokaryotic or eukaryotic cells.

With respect to mutations of the CRISPR enzyme, when the enzyme is not SpCas9, mutations may be made at any or all residues corresponding to positions 10, 762, 840, 854, 863 and/or 986 of *Francisella novicida* (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. In an aspect the invention provides as to any or each or all embodiments herein-discussed wherein the CRISPR enzyme comprises at least one or more, or at least two or more mutations, wherein the at least one or more mutation or the at least two or more mutations is as to D10, E762, H840, N854, N863, or D986 according to SpCas9 protein, e.g., D10A, E762A, H840A, N854A, N863A and/or D986A as to SpCas9, or N580 according to SaCas9, e.g., N580A as to SaCas9, or any corresponding mutation(s) in a Cas9 of an ortholog to Sp or Sa, or the CRISPR enzyme comprises at least one mutation wherein at least H840 or N863A as to Sp Cas9 or N580A as to Sa Cas9 is mutated; e.g., wherein the CRISPR enzyme comprises H840A, or D10A and H840A, or D10A and N863A, according to SpCas9 protein, or any corresponding mutation(s) in a Cas9 of an ortholog to Sp protein or Sa protein.

In a further aspect, the invention involves a computer-assisted method for identifying or designing potential compounds to fit within or bind to a CRISPR-Type II RT Cas system or a functional portion thereof or vice versa (a computer-assisted method for identifying or designing potential CRISPR-Type II RT systems or a functional portion thereof for binding to desired compounds) or a computer-assisted method for identifying or designing potential CRISPR-Type II RT Cas systems (e.g., with regard to predicting areas of the CRISPR-Type II RT Cas system to be able to be manipulated—for instance, based on crystal structure data or based on data of FnCas9 orthologs, or with respect to where a functional group such as an activator or repressor can be attached to the CRISPR-Type II RT Cas system, or as to Type II RT Cas (such as FnCas9) truncations or as to designing nickases), said method comprising:

using a computer system, e.g., a programmed computer comprising a processor, a data storage system, an input device, and an output device, the steps of:

(a) inputting into the programmed computer through said input device data comprising the three-dimensional co-ordinates of a subset of the atoms from or pertaining to the CRISPR-Type II RT Cas crystal structure, e.g., in the CRISPR-Type II RT Cas system binding domain or alternatively or additionally in domains that vary based on variance among such Cas orthologs or as to such Cass or as to nickases or as to functional groups, optionally with structural information from CRISPR-Type II RT Cas system complex(es), thereby generating a data set;

(b) comparing, using said processor, said data set to a computer database of structures stored in said computer data storage system, e.g., structures of compounds that bind or putatively bind or that are desired to bind to a CRISPR-Type II RT Cas system or as to Type II RT Cas (such as FnCas9) orthologs (e.g., as Cas9s or as to domains or regions that vary amongst Cas9 orthologs) or as to the CRISPR-Type II RT Cas crystal structure or as to nickases or as to functional groups;

(c) selecting from said database, using computer methods, structure(s)—e.g., CRISPR-Type II RT Cas structures that may bind to desired structures, desired structures that may bind to certain CRISPR-Type II RT Cas structures, portions of the CRISPR-Type II RT Cas system that may be manipulated, e.g., based on data from other portions of the CRISPR-Type II RT Cas crystal structure and/or from Type II RT Cas (e.g. FnCas9) orthologs, truncated versions, novel nickases or particular functional groups, or positions for attaching functional groups or functional-group-CRISPR-Type II RT Cas systems;

(d) constructing, using computer methods, a model of the selected structure(s); and (e) outputting to said output device the selected structure(s);

and optionally synthesizing one or more of the selected structure(s);

and further optionally testing said synthesized selected structure(s) as or in a CRISPR-Type II RT Cas system;

or, said method comprising: providing the co-ordinates of at least two atoms of the CRISPR-Type II RT Cas (e.g. FN Cas9 crystal structure, e.g., at least two atoms of the herein Crystal Structure Table of the CRISPR-Cas9 crystal structure or co-ordinates of at least a sub-domain of the CRISPR-Type II RT Cas crystal structure ("selected co-ordinates")), providing the structure of a candidate comprising a binding molecule or of portions of the CRISPR-Type II RT Cas system that may be manipulated, e.g., based on data from other portions of the CRISPR-Type II RT Cas crystal structure and/or from Type II RT Cas orthologs, or the structure of functional groups, and fitting the structure of the candidate to the selected co-ordinates, to thereby obtain product data comprising CRISPR-Type II RT Cas structures that may bind to desired structures, desired structures that may bind to certain CRISPR-Type II RT Cas structures, portions of the CRISPR-Type II RT Cas system that may be manipulated, truncated Type II RT Cas's, novel nickases, or particular functional groups, or positions for attaching functional groups or functional-group-CRISPR-Type II RT Cas systems, with output thereof; and optionally synthesizing compound(s) from said product data and further optionally comprising testing said synthesized compound(s) as or in a CRISPR-Type II RT Cas system.

The testing can comprise analyzing the CRISPR-Type II RT Cas system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (e.g. POWERPOINT), internet, email, documentary communication such as a computer program (e.g. WORD) document and the like. Accordingly, the invention also comprehends computer readable media containing: atomic co-ordinate data according to the herein-referenced Crystal Structure, said data defining the three dimensional structure of CRISPR-Type II RT Cas or at least one sub-domain thereof, or structure factor data for CRISPR-Type II RT Cas, said structure factor data being derivable from the atomic co-ordinate data of herein-referenced Crystal Structure. The computer readable media can also contain any data of the foregoing methods. The invention further comprehends methods a computer system for generating or performing rational design as in the foregoing methods containing either: atomic co-ordinate data according to herein-referenced Crystal Structure, said data defining the three dimensional structure of CRISPR-Type II RT Cas or at least one sub-domain thereof, or structure factor data for CRISPR-Type II RT Cas, said structure factor data being derivable from the atomic co-ordinate data of herein-referenced Crystal Structure. The invention further comprehends a method of doing business comprising providing to a user the computer system or the media or the three dimensional structure of CRISPR-Type II RT Cas or at least one sub-domain thereof, or structure factor data for CRISPR-Type II RT Cas, said structure set forth in and said structure factor data being derivable from the atomic co-ordinate data of herein-referenced Crystal Structure, or the herein computer media or a herein data transmission.

A "binding site" or an "active site" comprises or consists essentially of or consists of a site (such as an atom, a functional group of an amino acid residue or a plurality of such atoms and/or groups) in a binding cavity or region, which may bind to a compound such as a nucleic acid molecule, which is/are involved in binding.

By "fitting", is meant determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further.

By "root mean square (or rms) deviation", we mean the square root of the arithmetic mean of the squares of the deviations from the mean.

By a "computer system", is meant the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data. The data storage means may be RAM or means for accessing computer readable media of the invention. Examples of such systems are computer and tablet devices running Unix, Windows or Apple operating systems.

By "computer readable media", is meant any medium or media, which can be read and accessed directly or indirectly by a computer e.g., so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; thumb drive devices; cloud storage devices and hybrids of these categories such as magnetic/optical storage media.

In particular embodiments of the invention, the conformational variations in the crystal structures of the CRISPR-Type II RT Cas system or of components of the CRISPR-Type II RT Cas provide important and critical information about the flexibility or movement of protein structure regions relative to nucleotide (RNA or DNA) structure regions that may be important for CRISPR-Type II RT system function. The structural information provided for Type II RT Cas (Cas9 and e.g., *Francisella novicida* Cas9) as the CRISPR enzyme in the present application may be used to further engineer and optimize the CRISPR-Type II RT Cas system and this may be extrapolated to interrogate structure-function relationships in other RNA-targeting CRISPR enzyme systems as well, e.g., other Type II CRISPR enzyme systems.

The invention comprehends optimized functional CRISPR-Type II RT Cas enzyme systems. In particular the CRISPR enzyme comprises one or more mutations that converts it to an RNA binding protein to which functional domains exhibiting a function of interest may be recruited or appended or inserted or attached. In certain embodiments, the CRISPR-Type II RT Cas enzyme may comprises one or more mutations. In some embodiments, the RNA-targeting CRISPR enzyme has one or more mutations in a catalytic domain, wherein when transcribed, the RNA-targeting guide sequence directs sequence-specific binding of an RNA-targeting CRISPR complex to the target sequence, and wherein the enzyme further comprises a functional domain.

The structural information provided herein allows for interrogation of RNA-targeting RNA guide interaction with the target RNA and the Type II RT Cas enzyme (e.g., FnCas9) permitting engineering or alteration of RNA-targeting structure to optimize functionality of the entire RNA-targeting (CRISPR-Cas) system. For example, the RNA-targeting RNA guide may be extended, without colliding with the Cas protein by the insertion of adaptor proteins that can bind to RNA. These adaptor proteins can further recruit effector proteins or fusions which comprise one or more functional domains.

The compositions of the invention encompass a non-naturally occurring or engineered composition that may comprise an RNA-targeting guide RNA (Rt-gRNA) comprising a guide sequence capable of hybridizing to an RNA target sequence of interest in a cell and an RNA-targeting Cas enzyme, wherein the RNA-targeting Cas enzyme comprises two or more mutations, such that the enzyme has altered or diminished nuclease activity compared with the wild type enzyme. In particular embodiments, the RNA-targeting guide RNA is modified by the insertion of distinct RNA sequence(s) that bind to one or more adaptor proteins, and wherein the adaptor protein further recruits one or more heterologous functional domains. An aspect of the invention encompasses methods of modifying an RNA of interest to change RNA translation in a cell by introducing into the cell any of the compositions described herein.

An aspect of the invention is that the above elements are comprised in a single composition or comprised in individual compositions. These compositions may advantageously be applied to a host to elicit a functional effect on the RNA level.

In general, the RNA-targeting guide RNA (Rt-gRNA) is modified in a manner that provides specific binding sites (e.g., aptamers) for adapter proteins comprising one or more functional domains (e.g., via fusion protein) to bind to. The modified Rt-gRNA are modified such that once the Rt-gRNA forms a CRISPR complex (i.e. RNA-targeting enzyme binding to Rt-gRNA and target) the adapter proteins bind and, the functional domain on the adapter protein is positioned in a spatial orientation which is advantageous for the attributed function to be effective. The skilled person will understand that modifications to the Rt-gRNA which allow for binding of the adapter+functional domain but not proper positioning of the adapter+functional domain (e.g., due to steric hinderance within the three dimensial structure of the CRISPR complex) are modifications which are not intended.

As explained herein the functional domains may be, for example, one or more domains from the group comprising, consisting essentially of, or consisting of methylase activity, demethylase activity, translation activation activity, translation repression activity, histone modification activity, RNA cleavage activity, DNA cleavage activity, nucleic acid binding activity, and molecular switches (e.g., light inducible). In some cases it is advantageous that additionally at least one NLS is provided. In some instances, it is advantageous to position the NLS at the N terminus. When more than one functional domain is included, the functional domains may be the same or different.

The RNA targeting guide RNA or Rt-gRNA may be designed to include multiple binding recognition sites (e.g., aptamers) specific to the same or different adapter protein. The Rt-gRNA may be designed to bind to the promoter region −1000-+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified Rt-gRNA may be one or more modified Rt-gRNAs targeted to one or more target loci (e.g., at least 1 sgRNA, at least 2 sgRNA, at least 5 sgRNA, at least 10 sgRNA, at least 20 sgRNA, at least 30 sg RNA, at least 50 sgRNA) comprised in a composition.

Where the RNA targeting enzyme has natural RNA nuclease activity, the RT enzyme may be modified to have diminished nuclease activity e.g., nuclease inactivation of at least 70%, at least 80%, at least 90%, at least 95%, at least 97%, or 100% as compared with the wild type enzyme; or to put in another way, a Cas9 enzyme having advantageously about 0% of the nuclease activity of the non-mutated or wild type Cas9 enzyme or CRISPR enzyme, or no more than about 3% or about 5% or about 10% of the nuclease activity of the non-mutated or wild Type II RT Cas enzyme, e.g. of the non-mutated or wild type *Francisella novicida* Cas9 enzyme or CRISPR enzyme. This is possible by introducing mutations into the nuclease domains of the *Francisella novicida* Cas9 and orthologs thereof.

The inactivated Type II RT Cas CRISPR enzyme may have associated (e.g., via fusion protein) one or more functional domains, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that sgRNAs are designed to provide proper spacing for functional use (Fok1) as specifically described in Tsai et al. Nature Biotechnology, Vol. 32, Number 6, (June 2014). The adaptor protein may utlilize known linkers to attach such functional domains. In some cases it is advantageous that additionally at least one NLS is provided. In some instances, it is advantageous to position the NLS at the N terminus. When more than one functional domain is included, the functional domains may be the same or different.

In general, the positioning of the one or more functional domain on the inactivated Type II RT Cas CRISPR enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR enzyme.

Due to crystal structure experiments on SpCas9, the Applicant has identified that positioning the functional domain in the Rec1 domain, the Rec2 domain, the HNH domain, or the PI domain of the *Francisella novicida* Cas9 protein or any ortholog corresponding to these domains is advantageous. Positioning of the functional domains to the Rec1 domain or the Rec2 domain, of the protein or any ortholog corresponding to these domains, in some instances may be preferred. Positioning of the functional domains to the Rec1 domain at position 553, Rec1 domain at 575, the Rec2 domain at any position of 175-306 or replacement thereof, the HNH domain at any position of 715-901 or replacement thereof, or the PI domain at position 1153 of the *Francisella novicida* protein or any ortholog corresponding to these domains, in some instances may be preferred. Fok1 functional domain may be attached at the N terminus. When more than one functional domain is included, the functional domains may be the same or different.

The adaptor protein may be any number of proteins that binds to an aptamer or recognition site introduced into the modified Rt-gRNA and which allows proper positioning of one or more functional domains, once the Rt-gRNA has been incorporated into the RNA-targeting complex, to affect the target or other polynucleotides or proteins associated therewith with the attributed function. As explained in detail in this application such may be coat proteins, preferably bacteriophage coat proteins. The functional domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains.

Thus, the modified Rt-gRNA, the (inactivated) Type II RT Cas CRISPR enzyme (with or without functional domains), and the binding protein with one or more functional domains, may each individually be comprised in a composition and administered to a host individually or collectively. Alternatively, these components may be provided in a single composition for administration to a host. Administration to a host may be performed via viral vectors known to the skilled person or described herein for delivery to a host (e.g., lentiviral vector, adenoviral vector, AAV vector). As explained herein, use of different selection markers and concentration of Rt-gRNA (e.g., dependent on whether multiple Rt-gRNAs are used) may be advantageous for eliciting an improved effect.

The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals. (See, e.g., Platt et al., Cell (2014), 159 (2): 440-455, or PCT patent publications cited herein, such as WO 2014/093622 (PCT/US2013/074667), which are not believed prior to the present invention or application). For example, the target cell comprises Type II RT Cas CRISPR enzyme (e.g., FnCas9) conditionally or inducibly (e.g., in the form of Cre dependent constructs) and/or the adapter protein conditionally or inducibly and, on expression of a vector introduced into the target cell, the vector expresses that which induces or gives rise to the condition of CRISPR enzyme (e.g., FnCas9) expression and/or adaptor expression in the target cell. By applying the teaching and compositions of the current invention with the known method of creating a CRISPR complex, inducible RNA events affected by functional domains are also an aspect of the current invention. One more example of this is the creation of a CRISPR RNA knock-in/conditional transgenic animal (e.g., mouse comprising e.g., a Lox-Stop-polyA-Lox (LSL) cassette) and subsequent delivery of one or more compositions providing one or more modified Rt-gRNA (e.g.,-200 nucleotides to TSS of a target gene of interest for gene activation purposes) as described herein (e.g., modified Rt-gRNA with one or more aptamers recognized by coat proteins, e.g., MS2), one or more adapter proteins as described herein (MS2 binding protein linked to one or more VP64) and means for inducing the conditional animal (e.g., Cre recombinase for rendering Type II RT Cas expression inducible). Alternatively, the adaptor protein may be provided as a conditional or inducible element with a conditional or inducible CRISPR enzyme to provide an effective model for screening purposes, which advantageously only requires minimal design and administration of specific sgRNAs for a broad number of applications.

In any of the vector systems, vectors, compositions or methods described herein one or more amino acid residues of the RNA-targeting Cas protein may be modified. Modification may comprise mutation of one or more, or two or more, or three or more, amino acid residues of the RNA-targeting Cas protein. The one or more, or two or more, or three or more, mutations may be in one or more catalytically active domains of the RNA-targeting Cas protein.

In any such mutants the RNA-targeting Cas protein may have reduced or abolished nuclease activity compared with an RNA-targeting Cas protein lacking said mutations. Any of such one or more, or two or more, or three or more, mutations may be in a catalytically active domain of the RNA-targeting Cas protein comprising a RuvCI, RuvCII or RuvCIII domain.

In any of the vector systems, vectors, compositions or methods described herein the RNA-targeting Cas protein may comprise one or more heterologous functional domains.

The one or more heterologous functional domains may comprise one or more nuclear localization signal (NLS) domains, or at least two or more NLS domains.

The one or more heterologous functional domains may comprise one or more transcriptional activation domains, such as VP64. The one or more heterologous functional domains may comprise one or more transcriptional repression domains, such as a KRAB domain or a SID domain. The one or more heterologous functional domains may comprise one or more nuclease domains, such as Fok1. The one or more heterologous functional domains may have one or more of the following activities: methylase activity, demethylase activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity and nucleic acid binding activity.

The one or more heterologous functional domains may be at or near the amino-terminus of the RNA-targeting Cas protein and/or at or near the carboxy-terminus of the RNA-targeting Cas protein.

The one or more heterologous functional domains may be fused to the RNA-targeting Cas protein or tethered to the RNA-targeting Cas protein or linked to the RNA-targeting Cas protein by a linker moiety.

In any of the vector systems, vectors, compositions or methods described herein the RNA-targeting Cas protein may comprise an RNA-targeting Cas protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium* or *Corynebacterium*. The RNA-targeting Cas protein may comprise a chimeric RNA-targeting Cas protein comprising a first fragment from a first RNA-targeting Cas protein ortholog and a second fragment from a second RNA-targeting Cas protein ortholog, and wherein the first and second RNA-targeting Cas protein orthologs are different and wherein at least one of the first and second orthologs is *Francisella novicida*. At least one of the first and second RNA-targeting Cas protein orthologs may comprise an RNA-targeting Cas protein from an organism comprising *Streptococcus, Campylobacter, Nitratifractor, Staphylococcus, Parvibaculum, Roseburia, Neisseria, Gluconacetobacter*, Azospirillum, Sphaerochaeta, *Lactobacillus, Eubacterium* or *Corynebacterium*.

In any of the vector systems, vectors, compositions or methods described herein the tracrRNA may comprise one or more protein-binding RNA aptamers. The scaRNA may comprise one or more protein-binding RNA aptamers. The one or more aptamers are capable of binding a bacteriophage coat protein. The bacteriophage coat protein may be selected from the group comprising QB, F2, GA, fr, JP501, MS2, M12, R17, BZ13, JP34, JP500, KUI, M11, MX1, TW18, VK, SP, FI, ID2, NL95, TW19, AP205, ¢Cb5, ¢Cb8r, ¢Cb12r, ¢Cb23r, 7s and PRR1. Preferably, the bacteriophage coat protein is MS2.

In any of the vector systems, vectors, compositions or methods described herein the tracrRNA may be 30 or more, 40 or more or 50 or more nucleotides in length.

In any of the vector systems, vectors, compositions or methods described herein the RNA-targeting Cas protein may be further modified (e.g. by the introduction of one or more amino acid mutations, by truncation/deletion and/or insertion of one or more specific amino acids or amino acid sequences) to alter PAM specificity.

In any of the vector systems, vectors, compositions or methods described herein multiple Rt-gRNAs may be delivered, wherein each Rt-gRNAs is specific for a different target RNA whereby there is multiplexing.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53 (c) EPC and Rule 28 (b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2B provides a graph representing the processing states of tracrRNA as determined by RNA sequencing (SEQ ID NO: 36).

FIG. 9A-9C provides scaRNA sequences. FIG. 9A provides the sequence of scaRNA from Sampson et al. (2013, Nature 497:254-258) (SEQ ID NOS. 30-32, respectively, in order of appearance). FIG. 9B provides the sequence of Applicants' scaRNA from RNA sequencing (SEQ ID NO: 33) and FIG. 9C provides RNA Seq reads on ScaRNA (SEQ ID NO: 34).

Figure 1:
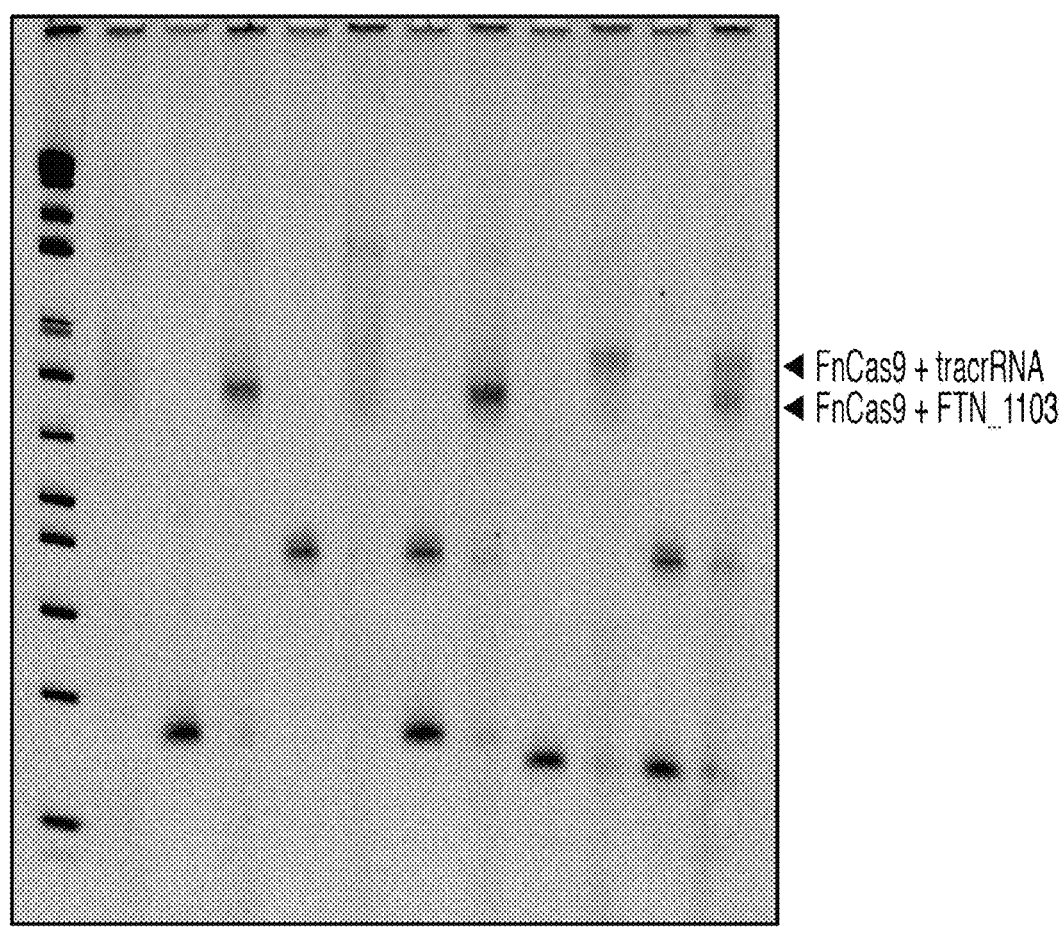
FIG. 1 provides a photograph representing a gel shift assay showing FnCas9 binding to tracr RNA, sgRNA, and FTN_1103.

The figures herein are for illustrative purposes only and are not necessarily drawn to scale.

DETAILED DESCRIPTION OF THE INVENTION

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") enzyme, including sequences encoding or delivering a Cas enzyme (DNA and/or RNA-targeting) enzyme, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g., CRISPR RNA and transactivating (tracr) RNA or a single guide RNA (sgRNA) (chimeric RNA)), a small RNA-targeting CRISPR/Cas system associated sequence ("sca-RNA") or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

The term "RNA-targeting system" refers collectively to transcripts and other elements involved in the expression of or directing the activity of RNA-targeting CRISPR-associated ("Cas") genes, including sequences encoding an RNA-targeting Cas protein and an RNA-targeting guide RNA comprising an RNA-targeting small CRISPR/Cas system associated RNA (scaRNA) sequence and an RNA-targeting trans-activating CRISPR/Cas system RNA (tracrRNA) sequence, or other sequences and transcripts from an RNA-targeting CRISPR locus. In general, an RNA-targeting system is characterized by elements that promote the formation of an RNA-targeting complex at the site of a target RNA sequence. In the context of formation of an RNA-targeting complex, "target sequence" refers to an RNA sequence to which an RNA-targeting guide RNA is designed to have complementarity, where hybridization between an target sequence and an RNA-targeting guide RNA promotes the formation of an RNA-targeting complex. In some embodiments, a target sequence is located in the nucleus or cytoplasm of a cell.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAST, Novoalign (Novocraft Technologies; available at www.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence may be selected to target any target sequence. In some embodiments, the target sequence is a sequence within a genome of a cell. Exemplary target sequences include those that are unique in the target genome.

As used herein, the term "RNA-targeting guide RNA" is any polynucleotide sequence having sufficient complementarity with a target RNA sequence to hybridize with the target RNA sequence and direct sequence-specific binding of an RNA-targeting complex to the target RNA sequence. In some embodiments, the degree of complementarity between an RNA-targeting guide sequence (within an RNA-targeting guide RNA) and its corresponding target RNA sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAST, Novoalign (Novocraft Technologies; available at www.novocraft.com), ELAND (Illumina, San Diego, CA), SOAP (available at soap.genomics.org.cn), and Maq (available at maq.sourceforge.net). The ability of an RNA-targeting guide sequence (within an RNA-targeting guide RNA) to direct sequence-specific binding of an RNA-targeting complex to a target RNA sequence may be assessed by any suitable assay. For example, the components of an RNA-targeting CRISPR system sufficient to form an RNA-targeting complex, including the RNA-targeting guide sequence to be tested, may be provided to a host cell having the corresponding target RNA sequence, such as by transfection with vectors encoding the components of the RNA-targeting complex, followed by an assessment of preferential targeting (e.g., cleavage) within the target RNA sequence, such as by Surveyor assay as described herein. Similarly, cleavage of a target RNA sequence may be evaluated in a test tube by providing the target RNA sequence, components of an RNA-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. An RNA-targeting guide sequence, and hence an RNA-targeting guide RNA may be selected to target any target RNA sequence. The target sequence is any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non coding RNA (ncRNA), long non-coding RNA (lncRNA), and small cytoplasmic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, an RNA-targeting guide RNA is selected to reduce the degree secondary structure within the RNA-targeting guide RNA. In some embodiments, about or less than about 75%, 50%, 40%, 30%, 25%, 20%, 15%, 10%, 5%, 1%, or fewer of the nucleotides of the RNA-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A.R. Gruber et al., 2008, Cell 106 (1): 23-24; and PA Carr and GM Church, 2009, Nature Biotechnology 27 (12): 1151-62).

In particular embodiments, the RNA-targeting guide RNA as taught herein comprises a small RNA-targeting CRISPR/Cas system associated sequence ("sca") and an RNA-targeting trans-activating CRISPR/Cas system sequence ("RNA-targeting tracr").

The "scaRNA" sequence includes any polynucleotide sequence that has sufficient complementarity with an RNA-targeting tracrRNA sequence to hybridize. The "tracrRNA" sequence includes any polynucleotide sequence that has sufficient complementarity with an RNA-targeting scaRNA sequence to hybridize. In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher. To enable heterologous expression of the Cas9 protein and associated small RNAs (tracrRNA, scaRNA, and crRNA) from *Francisella Novicida*, Applicants introduce these elements into the *E. coli* genome via "clonetegration" (St-Pierre, F. et al. ACS Synth Biol 2, 537-541 (2013).), a one step technique for cloning and recombinase-mediated integration. Applicants also clonetegrate the DNA for the endogenous RNA target of the FnCas9 protein in *F. Novicida*, FTN_1103. For verification of proper expression of both the Cas9 protein and small RNA, Applicants detect the presence of RNA via qPCR and expression of protein with western blot.

Applicants assay for activity of the FnCas9 on FTN_1103 in the heterologous system by measuring the difference in expression of FTN_1103 with and without a functioning FnCas9 system. Applicants create a non-functioning system by omission of FnCas9, scaRNA, or tracrRNA. By comparing FTN_1103 expression, with qPCR, between functioning and non-functioning heterologous systems, Applicants quantify the level of knockdown due to FnCas9.

Applicants also perform a challenge experiment to verify the DNA targeting and cleaving capability of FnCas9. This experiment closely parallels similar work in *E. coli* for the heterologous expression of StCas9 (Sapranauskas, R. et al. Nucleic Acids Res 39, 9275-9282 (2011)). Applicants introduce a plasmid containing both a PAM and a resistance gene into the heterologous *E. coli*, and then plate on the corresponding antibiotic. If there is DNA cleavage of the plasmid, Applicants observe no viable colonies.

In some embodiments, the degree of complementarity between the RNA-targeting tracr sequence and RNA-targeting sca sequence along the length of the shorter of the two when optimally aligned is about or more than about 25%, 30%, 40%, 50%, 60%, 70%, 80%, 90%, 95%, 97.5%, 99%, or higher. In some embodiments, the RNA-targeting tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the RNA-targeting tracr sequence and RNA-targeting sca sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. Further non-limiting examples of single polynucleotides comprising an RNA-targeting guide RNA, an RNA-targeting sca sequence, and an RNA-targeting tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactct-caagatttaGAAAtaaatcttgcagaagctacaaagataa ggctt-catgccgaaatcaacaccctgtcattttatggcagggtgttttcgttatttaa TTTTTT (SEQ ID NO: 1); (2) NNNNNNNNNNNNNNNNNNNNgttttgtactctcaGAAA tgcagaagctacaaagataaggcttcatgccg aaatcaacaccctgtcattt-tatggcagggtgttttcgttatttaaTTTTTT (SEQ ID NO: 2); (3) NNNNNNNNNNNNNNNNNNNNgttttgtactctcaGAA Atgcagaagctacaaagataaggcttcatgccg aaatcaacaccctgtcattt-tatggcagggtgtTTTTTT (SEQ ID NO: 3); (4) NNNNNNNNNNNNNNNNNNNNgttt-tagagctaGAAAtagcaagttaaaataaggctagtccgttatcaactt gaaaaagtggcaccgagtcggtgcTTTTTT (SEQ ID NO: 4); (5) NNNNNNNNNNNNNNNNNNNNgttt-tagagctaGAAATAGcaagttaaaataaggctagtccgttatcaac ttgaaaaagtgTTTTTTT (SEQ ID NO: 5); and (6) NNNNNNNNNNNNNNNNNNNNgttt-tagagctagAAATAGcaagttaaaataaggctagtccgttatca TT TTTTTT (SEQ ID NO: 6). Advantageously, the Cas9 isolated from *Francisella novicida* (FnCas9) is contemplated for the present invention.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the RNA-targeting sca RNA and RNA-targeting tracrRNA.

For minimization of toxicity and off-target effect, it will be important to control the concentration of RNA-targeting guide RNA delivered. Optimal concentrations of RNA-targetingguide RNA can be determined by testing different concentrations in a cellular or non-human eukaryote animal model and using deep sequencing the analyze the extent of modification at potential off-target genomic loci. The concentration that gives the highest level of on-target modification while minimizing the level of off-target modification should be chosen for in vivo delivery. The RNA-targeting system is derived advantageously from a type II CRISPR system. In some embodiments, one or more elements of an RNA-targeting system is derived from a particular organism comprising an endogenous RNA-targeting system, such as from *Francisella novicida*. In preferred embodiments of the invention, the RNA-targeting system is a type II CRISPR system and the Cas enzyme is Cas9. In particular embodiments, the Type II RNA-targeting Cas enzyme is a Type II RNA-targeting Cas9 isolated from or derived from *Francisella novicida*. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Cse1, Cse2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In embodiments, the *Francisella novicida* Cas9 (FnCas9) protein as referred to herein also encompasses a homologue or an orthologue of FnCas9. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April;22 (4): 359-66. doi: 10.1002/pro.2225.). See also Shmakov et al. (2015) for application in the field of CRISPR-Cas loci. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. In particular embodiments, the homologue or orthologue of FnCas9 as referred to herein has a sequence homology or identity of at least 80%, more preferably at least 85%, even more preferably at least 90%, such as for instance at least 95% with FnCas9. In further embodiments, the homologue or orthologue of FnCas9 as referred to herein has a sequence identity of at least 80%, more preferably at least 85%, even more preferably at least 90%, such as for instance at least 95% with the wild type FnCas9. Where the FnCas9 has one or more mutations (mutated), the homo-logue or orthologue of said FnCas9 as referred to herein has a sequence identity of at least 80%, more preferably at least 85%, even more preferably at least 90%, such as for instance at least 95% with the mutated FnCas9.

In an embodiment, the Type II RNA-targeting Cas protein may be a FnCas9 ortholog of a genus which includes but is not limited to *Corynebacterium, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*.

Methods of identifying orthologs of FnCas9 may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

In embodiments, the *Francisella novicida* Cas9 (FnCas9) protein as referred to herein also encompasses a functional variant of FnCas9 or a homologue or an orthologue thereof. A "functional variant" of a protein as used herein refers to a variant of such protein which retains at least partially the activity of that protein. Functional variants may include mutants (which may be insertion, deletion, or replacement mutants), including polymorphs, etc. Also included within functional variants are fusion products of such protein with another, usually unrelated, nucleic acid, protein, polypeptide or peptide. Functional variants may be naturally occurring or may be man-made.

In an embodiment, the Type II RNA-targeting Cas protein, in particular FnCas9 or an ortholog or homolog thereof, may be codon-optimized for expression in an eukaryotic cell. In an embodiment, the Type II RNA-targeting Cas protein, in particular FnCas9 or an ortholog or homolog thereof, may comprise one or more mutations, for example two or more mutations, for example three or more mutations. The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains.

In embodiments, the *Francisella novicida* Cas9 (FnCas9) protein as referred to herein also encompasses a functional variant of FnCas9 or a homologue or an orthologue thereof. A "functional variant" of a protein as used herein refers to a variant of such protein which retains at least partially the activity of that protein. Functional variants may include mutants (which may be insertion, deletion, or replacement mutants), including polymorphs, etc. Also included within functional variants are fusion products of such protein with another, usually unrelated, nucleic acid, protein, polypeptide or peptide. Functional variants may be naturally occurring or may be man-made.

In an embodiment, the Type II RNA-targeting Cas protein, in particular FnCas9 or an ortholog or homolog thereof, may be codon-optimized for expression in an eukaryotic cell. In an embodiment, the Type II RNA-targeting Cas protein, in particular FnCas9 or an ortholog or homolog thereof, may comprise one or more mutations, for example two or more mutations, for example three or more mutations. The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains.

In an embodiment, the Type II RNA-targeting Cas protein, in particular FnCas9 or an ortholog or homolog thereof, may be used as a generic RNA binding protein with fusion to or being operably linked to a functional domain. Exemplary functional domains may include but are not limited to translational initiator, translational activator, translational repressor, nucleases, in particular ribonucleases, a spliceosome, beads, a light inducible/controllable domain or a chemically inducible/controllable domain.

In some embodiments, the unmodified RNA-targeting Cas protein may have cleavage activity. In some embodiments, the RNA-targeting Cas protein may direct cleavage of one or both RNA strands at the location of a target sequence, such as within the target sequence and/or within the complement of the target sequence. In some embodiments, the RNA-targeting Cas protein may direct cleavage of one or both RNA strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes an RNA-targeting Cas protein that may be mutated with respect to a corresponding wild-type enzyme such that the mutated RNA-targeting Cas protein lacks the ability to cleave one or both RNA strands of a target polynucleotide containing a target sequence. As a further example, two or more catalytic domains of Cas9 (RuvC I, RuvC II, and RuvC III or the HNH domain) may be mutated to produce a mutated Cas9 substantially lacking all RNA cleavage activity. In some embodiments, an RNA-targeting Cas protein may be considered to substantially lack all RNA cleavage activity when the RNA cleavage activity of the mutated enzyme is about no more than 25%, 10%, 5%, 1%, 0.1%, 0.01%, or less of the RNA cleavage activity of the non-mutated form of the enzyme; an example can be when the RNA cleavage activity of the mutated form is nil or negligible as compared with the non-mutated form. A Cas enzyme may be identified Cas9 as this can refer to the general class of enzymes that share homology to the biggest nuclease with multiple nuclease domains from the type II CRISPR system. Most preferably, the Cas9 enzyme is from *Francisella novicida* (FnCas9 or FinCas9), or is derived from FinCas9. By derived, Applicants mean that the derived enzyme is largely based, in the sense of having a high degree of sequence homology with, a wildtype enzyme, but that it has been mutated (modified) in some way as known in the art or as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Francisella novicida*. However, it will be appreciated that this invention includes many more Cas9s from other species of microbes. In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic RNA binding protein.

Typically, in the context of an endogenous RNA-targeting system, formation of an RNA-targeting complex (comprising an RNA-targeting guide RNA hybridized to a target sequence and complexed with one or more RNA-targeting Cas proteins) results in cleavage of one or both RNA strands in or near (e.g., within 1, 2, 3, 4, 5, 6, 7, 8, 9, 10, 20, 50, or more base pairs from) the target sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding an RNA-targeting Cas protein is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding an RNA-targeting Cas proteincorrespond to the most frequently used codon for a particular amino acid.

In some embodiments, a vector encodes an RNA-targeting Cas protein comprising one or more nuclear localization sequences (NLSs), such as about or more than about 1, 2, 3, 4, 5, 6, 7, 8, 9, 10, or more NLSs. In some embodiments, the RNA-targeting Cas protein comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 7); the NLS from nucleoplasmin (e.g., the nucleoplasmin bipartite NLS with the sequence KRPAATKKAGQAKKKK (SEQ ID NO: 8)); the c-myc NLS having the amino acid sequence PAAKRVKLD (SEQ ID NO: 9) or RQRRNELKRSP (SEQ ID NO: 10); the hRNPA1 M9 NLS having the sequence NQSSNFGPMKGGNFGGRSSGPYGGGGQYFAKPRNQGGY (SEQ ID NO: 11); the sequence RMRIZFKNKGKDTAELRRRRVEVSVELRKAKKDEQILKRRNV (SEQ ID NO: 12) of the IBB domain from importin-alpha; the sequences VSRKRPRP (SEQ ID NO: 13) and PPKKARED (SEQ ID NO: 14) of the myoma T protein; the sequence PQPKKKPL (SEQ ID NO: 15) of human p53; the sequence SALIKKKKKMAP (SEQ ID NO: 16) of mouse c-abl IV; the sequences DRLRR (SEQ ID NO: 17) and PKQKKRK (SEQ ID NO: 18) of the influenza virus NS1; the sequence RKLKKKIKKL (SEQ ID NO: 19) of the Hepatitis virus delta antigen; the sequence REKKKFLKRR (SEQ ID NO: 20) of the mouse Mx1 protein; the sequence KRKGDEVDGVDEVAKKKSKK (SEQ ID NO: 21) of the human poly (ADP-ribose) polymerase; and the sequence RKCLQAGMNLEARKTKK (SEQ ID NO: 22) of the steroid hormone receptors (human) glucocorticoid. In general, the one or more NLSs are of sufficient strength to drive accumulation of the RNA-targeting Cas protein in a detectable amount in the nucleus of a eukaryotic cell. In general, strength of nuclear localization activity may derive from the number of NLSs in the RNA-targeting Cas protein, the particular NLS(s) used, or a combination of these factors. Detection of accumulation in the nucleus may be performed by any suitable technique. For example, a detectable marker may be fused to the RNA-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of RNA-targeting complex formation (e.g., assay for RNA cleavage or mutation at the target sequence, or assay for altered gene expression activity affected by RNA-targeting complex formation and/or RNA-targeting Cas protein activity), as compared to a control not exposed to the RNA-targeting Cas protein or RNA-targeting complex, or exposed to an RNA-targeting Cas protein lacking the one or more NLSs.

In some embodiments, one or more vectors driving expression of one or more elements of an RNA-targeting system are introduced into a host cell such that expression of the elements of the RNA-targeting system direct formation of an RNA-targeting complex at one or more target sites. For example, an RNA-targeting Cas enzyme and an RNA-targeting guide RNA could each be operably linked to separate regulatory elements on separate vectors. Or, RNA(s) of the RNA-targeting system can be delivered to a transgenic RNA-targeting Cas9 animal or mammal, e.g., an animal or mammal that constitutively or inducibly or conditionally expresses RNA-targeting Cas9; or an animal or mammal that is otherwise expressing RNA-targeting Cas9 or has cells containing RNA-targeting Cas9, such as by way of prior administration thereto of a vector or vectors that code for and express in vivo RNA-targeting Cas9. Alternatively, two or more of the elements expressed from the same or different regulatory elements, may be combined in a single vector, with one or more additional vectors providing any components of the RNA-targeting system not included in the first vector. RNA-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding an RNA-targeting Cas protein and the RNA-targeting guide RNA, embedded within one or more intron sequences (e.g., each in a different intron, two or more in at least one intron, or all in a single intron). In some embodiments, the RNA-targeting Cas protein and the RNA-targeting guide RNA may be operably linked to and expressed from the same promoter. Delivery vehicles, vectors, particles, nanoparticles, formulations and components thereof for expression of one or more elements of an RNA-targeting system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of an RNA-targeting complex to a target sequence in a eukaryotic cell. In some embodiments, a vector comprises two or more insertion sites, so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target RNA-targeting activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding an RNA-targeting Cas protein. RNA-targeting Cas protein or RNA-targeting guide RNA or RNA(s) can be delivered separately; and advantageously at least one of these is delivered via a nanoparticle complex. RNA-targeting Cas protein mRNA can be delivered prior to the RNA-targeting guide RNA to give time for RNA-targeting Cas protein to be expressed. RNA-targeting Cas protein mRNA might be administered 1-12 hours (preferably around 2-6 hours) prior to the administration of RNA-targeting guide RNA. Alternatively, RNA-targeting Cas protein mRNA and RNA-targeting guide RNA can be administered together. Advantageously, a second booster dose of RNA-targeting guide RNA can be administered 1-12 hours (preferably around 2-6 hours) after the initial administration of RNA-targeting Cas protein mRNA+RNA-targeting guide RNA. Additional administrations of RNA-targeting Cas protein mRNA and/or RNA-targeting guide RNA might be useful to achieve the most efficient levels of genome modification.

In one aspect, the invention provides methods for using one or more elements of an RNA-targeting system. The RNA-targeting complex of the invention provides an effective means for modifying a target RNA. The RNA-targeting complex of the invention has a wide variety of utility including modifying (e.g., deleting, inserting, translocating, inactivating, activating) a target RNA in a multiplicity of cell types. As such the RNA-targeting complex of the invention has a broad spectrum of applications in, e.g., gene therapy, drug screening, disease diagnosis, and prognosis. An exemplary RNA-targeting complex comprises an RNA-targeting Cas protein complexed with an RNA-targeting guide RNA hybridized to a target sequence within the target RNA. In one embodiment, this invention provides a method of cleaving a target RNA. The method may comprise modifying a target RNA using an RNA-targeting complex that binds to the target RNA and effect cleavage of said target RNA. In an embodiment, the RNA-targeting complex of the invention, when introduced into a cell, may create a break (e.g., a single or a double strand break) in the RNA sequence. For example, the method can be used to cleave a disease RNA in a cell. For example, an exogenous RNA template comprising a sequence to be integrated flanked by an upstream sequence and a downstream sequence may be introduced into a cell. The upstream and downstream sequences share sequence similarity with either side of the site of integration in the RNA. Where desired, a donor RNA can be mRNA. The exogenous RNA template comprises a sequence to be integrated (e.g., a mutated RNA). The sequence for integration may be a sequence endogenous or exogenous to the cell. Examples of a sequence to be integrated include RNA encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous RNA template are selected to promote recombination between the RNA sequence of interest and the donor RNA. The upstream sequence is an RNA sequence that shares sequence similarity with the RNA sequence upstream of the targeted site for integration. Similarly, the downstream sequence is an RNA sequence that shares sequence similarity with the RNA sequence downstream of the targeted site of integration. The upstream and downstream sequences in the exogenous RNA template can have 75%, 80%, 85%, 90%, 95%, or 100% sequence identity with the targeted RNA sequence. Preferably, the upstream and downstream sequences in the exogenous RNA template have about 95%, 96%, 97%, 98%, 99%, or 100% sequence identity with the targeted RNA sequence. In some methods, the upstream and downstream sequences in the exogenous RNA template have about 99% or 100% sequence identity with the targeted RNA sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous RNA template may further comprise a marker. Such a marker may make it easy to screen for targeted integrations. Examples of suitable markers include restriction sites, fluorescent proteins, or selectable markers. The exogenous RNA template of the invention can be constructed using recombinant techniques (see, for example, Sambrook et al., 2001 and Ausubel et al., 1996). In a method for modifying a target RNA by integrating an exogenous RNA template, a break (e.g., double stranded break in dsRNA) is introduced into the RNA sequence by the RNA-targeting complex, the break is repaired via homologous recombination with an exogenous RNA template such that the template is integrated into the RNA target. The presence of a double-stranded break facilitates integration of the template. In other embodiments, this invention provides a method of modifying expression of an RNA in a eukaryotic cell. The method comprises increasing or decreasing expression of a target polynucleotide by using an RNA-targeting complex that binds to the RNA (e.g., mRNA or pre-mRNA). In some methods, a target RNA can be inactivated to effect the modification of the expression in a cell. For example, upon the binding of an RNA-targeting complex to a target sequence in a cell, the target RNA is inactivated such that the sequence is not translated, the coded protein is not produced, or the sequence does not function as the wild-type sequence does. For example, a protein or microRNA coding sequence may be inactivated such that the protein or microRNA or pre-microRNA transcript is not produced. The target RNA of an RNA-targeting complex can be any RNA endogenous or exogenous to the eukaryotic cell. For example, the target RNA can be an RNA residing in the nucleus of the eukaryotic cell. The target RNA can be a sequence (e.g., mRNA or pre-mRNA) coding a gene product (e.g., a protein) or a non-coding sequence (e.g., ncRNA, lncRNA, tRNA, or rRNA). Examples of target RNA include a sequence associated with a signaling biochemical pathway, e.g., a signaling biochemical pathway-associated RNA. Examples of target RNA include a disease associated RNA. A "disease-associated" RNA refers to any RNA which is yielding translation products at an abnormal level or in an abnormal form in cells derived from a disease-affected tissues compared with tissues or cells of a non disease control. It may be an RNA transcribed from a gene that becomes expressed at an abnormally high level; it may be an RNA transcribed from a gene that becomes expressed at an abnormally low level, where the altered expression correlates with the occurrence and/or progression of the disease. A disease-associated RNA also refers to an RNA transcribed from a gene possessing mutation(s) or genetic variation that is directly responsible or is in linkage disequilibrium with a gene(s) that is responsible for the etiology of a disease. The translated products may be known or unknown, and may be at a normal or abnormal level. The target RNA of an RNA-targeting complex can be any RNA endogenous or exogenous to the eukaryotic cell. For example, the target RNA can be an RNA residing in the nucleus of the eukaryotic cell. The target RNA can be a sequence (e.g., mRNA or premRNA) coding a gene product (e.g., a protein) or a non-coding sequence (e.g., ncRNA, lncRNA, tRNA, or rRNA).

In some embodiments, the method may comprise allowing an RNA-targeting complex to bind to the target RNA to effect cleavage of said target RNA thereby modifying the target RNA, wherein the RNA-targeting complex comprises an RNA-targeting Cas protein complexed with an RNA-targeting guide RNA hybridized to a target sequence within said target RNA. In one aspect, the invention provides a method of modifying expression of an RNA in a eukaryotic cell. In some embodiments, the method comprises allowing an RNA-targeting complex to bind to the RNA such that said binding results in increased or decreased expression of said RNA; wherein the RNA-targeting complex comprises an RNA-targeting Cas protein complexed with an RNA-targeting guide RNA. Similar considerations and conditions apply as above for methods of modifying a target RNA. In fact, these sampling, culturing and re-introduction options apply across the aspects of the present invention. In one aspect, the invention provides for methods of modifying a target RNA in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the RNA-targeting complex may comprise an RNA-targeting Cas protein complexed with an RNA-targeting guide RNA hybridized to a target sequence.

The invention relates to the engineering and optimization of systems, methods and compositions used for the control of gene expression involving RNA sequence targeting, that relate to the RNA-targeting system and components thereof. In advantageous embodiments, the Cas enzyme is Cas9. In preferred embodiments, the Cas enzyme is FnCas9. An advantage of the present methods is that the CRISPR system minimizes or avoids off-target binding and its resulting side effects. This is achieved using systems arranged to have a high degree of sequence specificity for the target RNA.

In relation to an RNA-targeting complex or system preferably, the RNA-targeting tracr sequence has one or more hairpins and is 30 or more nucleotides in length, 40 or more nucleotides in length, or 50 or more nucleotides in length; the RNA-targeting sca sequence is between 10 to 30 nucleotides in length, the RNA-targeting Cas protein is a Type II Cas9 enzyme.

The use of two different aptamers (distinct RNA-targeting guide RNAs) allows an activator-adaptor protein fusion and a repressor-adaptor protein fusion to be used, with different RNA-targeting guide RNAs, to activate expression of one RNA, whilst repressing another. They, along with their different RNA-targeting guide RNAs can be administered together, or substantially together, in a multiplexed approach. A large number of such modified RNA-targeting guide RNAs can be used all at the same time, for example 10 or 20 or 30 and so forth, whilst only one (or at least a minimal number) of Cas9s to be delivered, as a comparatively small number of Cas9s can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the Gly-Ser linker.

It is also envisaged that the RNA-targeting Cas protein-guide RNA complex as a whole may be associated with two or more functional domains. For example, there may be two or more functional domains associated with the RNA-targeting Cas protein, or there may be two or more functional domains associated with the RNA-targeting guide RNA (via one or more adaptor proteins), or there may be one or more functional domains associated with the RNA-targeting Cas protein and one or more functional domains associated with the RNA-targeting guide RNA (via one or more adaptor proteins).

The fusion between the adaptor protein and the activator or repressor may include a linker. For example, Gly-Ser linkers GGGS (SEQ ID NO: 23) can be used. They can be used in repeats of 3 ((GGGGS)$_3$ (SEQ ID NO: 24)) or 6 (SEQ ID NO: 25), 9 (SEQ ID NO: 26) or even 12 (SEQ ID NO: 27) or more, to provide suitable lengths, as required. Linkers can be used between the RNA-targeting guide RNAs and the functional domain (activator or repressor), or between the RNA-targeting Cas protein (Cas9) and the functional domain (activator or repressor). The linkers the user to engineer appropriate amounts of "mechanical flexibility".

The invention comprehends an RNA-targeting complex comprising an RNA-targeting Cas protein and an RNA-targeting guide RNA, wherein the RNA-targeting Cas protein comprises at least one mutation, such that the RNA-targeting Cas protein has no more than 5% of the activity of the RNA-targeting Cas protein not having the at least one mutation and, optional, at least one or more nuclear localization sequences; the RNA-targeting guide RNA comprises a guide sequence capable of hybridizing to a target sequence in an RNA of interest in a cell; and wherein: the RNA-targeting Cas protein is associated with two or more functional domains; or at least one loop of the RNA-targeting guide RNA is modified by the insertion of distinct RNA sequence(s) that bind to one or more adaptor proteins, and wherein the adaptor protein is associated with two or more functional domains; or the RNA-targeting Cas protein is associated with one or more functional domains and at least one loop of the RNA-targeting guide RNA is modified by the insertion of distinct RNA sequence(s) that bind to one or more adaptor proteins, and wherein the adaptor protein is associated with one or more functional domains.

Delivery Generally

Vector delivery, e.g., plasmid, viral delivery: The RNA-targeting guide RNA, for instance a FnCas9, and/or an RNA-targeting guide RNA, can be delivered using any suitable vector, e.g., plasmid or viral vectors, such as adeno associated virus (AAV), lentivirus, adenovirus or other viral vector types, or combinations thereof. RNA-targeting Cas9 and one or more RNA-targeting guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^0$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding an RNA-targeting Cas protein, operably linked to said promoter; (iii) a selectable marker; (iv) an origin of replication; and (v) a transcription terminator downstream of and operably linked to (ii). The plasmid can also encode the RNA-targeting guide RNA, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20g and from mice experiments one can scale up to a 70 kg individual.

In some embodiments the RNA-targeting guide RNAs are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9:210-216; Sorensen et al., J. Mol. Biol. 2003, 327: 761-766; Lewis et al., Nat. Gen. 2002, 32:107-108 and Simeoni et al., NAR 2003, 31, 11:2717-2724) and may be applied to the present invention.

Indeed, RNA delivery is a useful method of in vivo delivery. It is possible to deliver RNA-targeting Cas protein and RNA-targeting guide RNA into cells using liposomes or nanoparticles. Thus delivery of the RNA-targeting Cas protein, such as a Cas9 and/or delivery of the RNA-targeting guide RNAs of the invention may be in RNA form and via microvesicles, liposomes or nanoparticles. For example, Cas9 mRNA and RNA-targeting guide RNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19:3112-3118, 2010) or exosomes (Schroeder, A., Levins, C., Cortez, C., Langer, R., and Anderson, D., Lipid-based nanotherapeutics for siRNA delivery, Journal of Internal Medicine, 267:9-21, 2010, PMID: 20059641). Indeed, exosomes have been shown to be particularly useful in delivery siRNA, a system with some parallels to the RNA-targeting system. For instance, El-Andaloussi S, et al. ("Exosome-mediated delivery of siRNA in vitro and in vivo." Nat Protoc. 2012 December;7 (12): 2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (a-tocopherol) may be conjugated with RNA-targeting Cas protein and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of RNA-targeting Cas protein conjugated to α-tocopherol and co-administered with HDL targeted to the brain may be contemplated for humans in the present invention, for example, about 3 nmol to about 3 μmol of RNA-targeting Cas protein targeted to the brain may be contemplated. Zou et al. (HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of $1 \times 10^9$ transducing units (TU)/ml by an intrathecal catheter. A similar dosage of RNA-targeting Cas protein expressed in a lentiviral vector targeted to the brain may be contemplated for humans in the present invention, for example, about 10-50 ml of RNA-targeting Cas protein targeted to the brain in a lentivirus having a titer of $1 \times 10^9$ transducing units (TU)/ml may be contemplated.

In terms of local delivery to the brain, this can be achieved in various ways. For instance, material can be delivered intrastriatally e.g., by injection. Injection can be performed stereotactically via a craniotomy.

Packaging and Promoters Generally

Ways to package RNA-targeting Cas protein (such as FnCas9) coding nucleic acid molecules, e.g., DNA, into vectors, e.g., viral vectors, to mediate genome modification in vivo include:

Single virus vector:
  Vector containing two or more expression cassettes:
   Promoter-RNA-targeting Cas protein coding nucleic acid molecule-terminator
   Promoter-RNA-targeting guide RNA1-terminator
   Promoter-RNA-targeting guide RNA (N)-terminator (up to size limit of vector)
Double virus vector:
  Vector 1 containing one expression cassette for driving the expression of RNA-targeting Cas protein (such as FnCas9)
   Promoter-RNA-targeting Cas protein coding nucleic acid molecule-terminator
  Vector 2 containing one more expression cassettes for driving the expression of one or more RNA-targeting guideRNAs
   Promoter-RNA-targeting guide RNA1-terminator
   Promoter-RNA-targeting guide RNA1 (N)-terminator (up to size limit of vector) To mediate homology-directed repair.

In addition to the single and double virus vector approaches described above, an additional vector is used to deliver a homology-direct repair template.

The promoter used to drive RNA-targeting Cas protein (such as FnCas9) coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of RNA-targeting Cas protein (such as FnCas9).

For ubiquitous expression, can use promoters: CMV, CAG, CBh, PGK, SV40, Ferritin heavy or light chains, etc.

For brain or other CNS expression, can use promoters: Synapsin I for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can use OG-2.

The promoter used to drive RNA-targeting guide RNA can include:
Pol III promoters such as U6 or H1
Use of Pol II promoter and intronic cassettes to express RNA-targeting guide RNA Adeno Associated Virus (AAV)

RNA-targeting Cas protein (such as FnCas9) and one or more RNA-targeting guide RNA can be delivered using adeno associated virus (AAV), lentivirus, adenovirus or other plasmid or viral vector types, in particular, using formulations and doses from, for example, U.S. Pat. Nos. 8,454,972 (formulations, doses for adenovirus), 8,404,658 (formulations, doses for AAV) and 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of RNA-targeting Cas protein (such as FnCas9) can be driven by a cell-type specific promoter. For example, liver-specific expression might use the Albumin promoter and neuron-specific expression (e.g., for targeting CNS disorders) might use the Synapsin I promoter.

In terms of in vivo delivery, AAV is advantageous over other viral vectors for a couple of reasons:

Low toxicity (this may be due to the purification method not requiring ultracentrifugation of cell particles that can activate the immune response) and
  Low probability of causing insertional mutagenesis because it doesn't integrate into the host genome.

AAV has a packaging limit of 4.5 or 4.75 Kb. This means that RNA-targeting Cas protein (such as FnCas9) as well as a promoter and transcription terminator have to be all fit into the same viral vector. Therefore embodiments of the invention include utilizing homologs of RNA-targeting Cas protein (such as FnCas9) that are shorter.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82:5887-5911 (2008)) is as follows:

Cells were transfected with 10 μg of lentiviral transfer plasmid (pCas-ES10) and the following packaging plasmids: 5 μg of pMD2.G (VSV-g pseudotype), and 7.5 μg of psPAX2 (gag/pol/rev/tat). Transfection was done in 4 mL Opti-MEM with a cationic lipid delivery agent (50 μL Lipofectamine 2000 and 100 μl Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 μm low protein binding (PVDF) filter. They were then spun in a ultracentrifuge for 2 hours at 24,000 rpm. Viral pellets were resuspended in 50 μl of DMEM overnight at 4C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8:275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the RNA-targeting system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2: 36ra43) may be used and/or adapted to the RNA-targeting system of the present inven-

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCas ES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to Opti-MEM (serum-free) media and transfection was done 4 hours later.

tion. A minimum of $2.5 \times 10^6$ CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-$cm^2$ tissue culture flasks coated with fibronectin (25 mg/$cm^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571, US20040013648, US20070025970, US20090111106 and US Patent No. U.S. Pat. No. 7,259,015.
RNA Delivery RNA delivery: The RNA-targeting Cas protein, for instance a FnCas9, and/or RNA-targeting guide RNA, can also be delivered in the form of RNA. RNA-targeting Cas protein (such as FnCas9) mRNA can be generated using in vitro transcription. For example, RNA-targeting Cas protein (such as FnCas9) mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. RNA-targeting guide RNAs can also be transcribed using in vitro transcription from a cassette containing T7_promoter-GG-RNA-targeting guide RNA sequence.

To enhance expression and reduce possible toxicity, the RNA-targeting Cas protein-coding sequence and/or the RNA-targeting guide RNA can be modified to include one or more modified nucleoside e.g., using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.
Nanoparticles RNA-targeting Cas protein (such as FnCas9) mRNA and RNA-targeting guide RNA may be delivered simultaneously using nanoparticles or lipid envelopes.

For example, Su X, Fricke J, Kavanagh DG, Irvine DJ ("In vitro and in vivo mRNA delivery using lipid-enveloped pH-responsive polymer nanoparticles" Mol Pharm. 2011 Jun. 6;8 (3): 774-87. doi: 10.1021/mp100390w. Epub 2011 Apr. 1) describes biodegradable core-shell structured nanoparticles with a poly (β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACS Nano, 2013. 7 (2): 1016-1026; Siew, A., et al. Mol Pharm, 2012. 9 (1): 14-28; Lalatsa, A., et al. J Contr Rel, 2012. 161 (2): 523-36; Lalatsa, A., et al., Mol Pharm, 2012. 9 (6): 1665-80; Lalatsa, A., et al. Mol Pharm, 2012. 9 (6): 1764-74; Garrett, N. L., et al. J Biophotonics, 2012. 5 (5-6): 458-68; Garrett, N. L., et al. J Raman Spect, 2012. 43 (5): 681-688; Ahmad, S., et al. J Royal Soc Interface 2010. 7: S423-33; Uchegbu, I.F. Expert Opin Drug Deliv, 2006. 3 (5): 629-40; Qu, X.,et al. Biomacromolecules, 2006. 7 (12): 3452-9 and Uchegbu, I. F., et al. Int J Pharm, 2001. 224:185-199). Doses of about 5 mg/kg are contemplated, with single or multiple doses, depending on the target tissue.

In one embodiment, nanoparticles that can deliver RNA to a cancer cell to stop tumor growth developed by Dan Anderson's lab at MIT may be used and/or adapted to the RNA-targeting system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6;110 (32): 12881-6; Zhang et al., Adv Mater. 2013 Sep. 6;25 (33): 4641-5; Jiang et al., Nano Lett. 2013 Mar. 13;13 (3): 1059-64; Karagiannis et al., ACS Nano. 2012 Oct. 23;6 (10): 8484-7; Whitehead et al., ACS Nano. 2012 Aug. 28;6 (8): 6922-9 and Lee et al., Nat Nanotechnol. 2012 Jun. 3;7 (6): 389-93.

U.S. patent application No. 20110293703 relates to lipidoid compounds are also particularly useful in the administration of polynucleotides, which may be applied to deliver the RNA-targeting system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly (beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the RNA-targeting system of the present invention.

In another embodiment, lipid nanoparticles (LNPs) are contemplated. An anti-transthyretin small interfering RNA has been encapsulated in lipid nanoparticles and delivered to humans (see, e.g., Coelho et al., N Engl J Med 2013; 369:819-29), and such a system may be adapted and applied to the RNA-targeting system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding RNA-targeting Cas proteinto the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-220 Dec. 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethyl-ammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-220 Dec. 2011). A dosage of 1 µg/ml of LNP or RNA-targeting RNA in or associated with the LNP may be contemplated, especially for a formulation containing DLinKC2-DMA.

Preparation of LNPs and encapsulation may be used and/or adapted from Rosin et al, Molecular Therapy, vol. 19, no. 12, pages 1286-220 Dec. 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethyl-aminoethyl)-[1,3]-dioxolane (DLinKC2-DMA), (3-0-[2"-(methoxypolyethyleneglycol) 2000) succinoyl]-1,2-dimyristoyl-sn-glycol (PEG-S-DMG), and R-3-[(ω-methoxy-poly (ethylene glycol) 2000) carbamoyl]-1,2-dimyristyloxypropyl-3-amine (PEG-C-DOMG) may be provided by Tekmira Pharmaceuticals (Vancouver, Canada) or synthesized. Cholesterol may be purchased from Sigma (St Louis, MO). The specific RNA-targeting complex RNA may be encapsulated in LNPs containing DLinDAP, DLinDMA, DLinK-DMA, and DLinKC2-DMA (cationic lipid: DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid: DSPC: cholesterol: PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of an RNA-targeting system or components thereof.

Preparation of large LNPs may be used and/or adapted from Rosin et al, Molecular Therapy, vol. 19, no. 12, pages 1286-220 Dec. 2011. A lipid premix solution (20.4 mg/ml total lipid concentration) may be prepared in ethanol containing DLinKC2-DMA, DSPC, and cholesterol at 50:10: 38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt: wt), followed by incubation for 30 minutes at 37° C. to form loaded LNPs. The mixture may be subsequently dialyzed overnight in PBS and filtered with a 0.45-μm syringe filter.

Spherical Nucleic Acid (SNA™) constructs and other nanoparticles (particularly gold nanoparticles) are also contemplated as a means to delivery RNA-targeting system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638, Zhang et al., J. Am. Chem. Soc. 2012 134:16488-1691, Weintraub, Nature 2013 495: S14-S16, Choi et al., Proc. Natl. Acad. Sci. USA. 2013 110 (19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGFR2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of RNA-targeting complex RNA is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7, 10-tetraacetic acid mono (N-hydroxysuccinimide ester) (DOTA-NHSester) was ordered from Macrocyclics (Dallas, TX). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, CA) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts an RNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles comprise, consist essentially of, or consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the RNA-targeting system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g., diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of RNA-targeting system e.g., RNA-targeting Cas protein or mRNA, or RNA-targeting guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi: 10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Nanoparticles

In terms of this invention, it is preferred to have one or more components of RNA-targeting complex, e.g., RNA-targeting Cas protein or mRNA, or RNA-targeting guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm.

Nanoparticles encompassed in the present invention may be provided in different forms, e.g., as solid nanoparticles (e.g., metal such as silver, gold, iron, titanium), non-metal, lipid-based solids, polymers, suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm$^3$ with a mean diameter of between 5 µm and 30 µm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable nanoparticles having a biodegradable solid core containing a biologically active material and poly (alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can be envisioned that such conjugated lipomers can be used in the context of the RNA-targeting system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). C71 was synthesized by reacting C15 epoxide-terminated lipids with PEI600 at a 14:1 molar ratio, and was formulated with C14 PEG2000 to produce nanoparticles (diameter between 35 and 60 nm) that were stable in PBS solution for at least 40 days.

An epoxide-modified lipid-polymer may be utilized to deliver the RNA-targeting system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29:341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 µg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 µF resulted in the greatest retention of RNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, $P<0.05$, versus 62%, $P<0.01$) in both siRNA-RVG-9R-treated and siRNA-RVG exosome-treated mice was observed, resulting from a significant decrease in BACE1 mRNA levels (66% [+ or −] 15%, $P<0.001$ and 61% [+ or −] 13% respectively, $P<0.01$). Moreover, Applicants demonstrated a significant decrease (55%, $P<0.05$) in the total [beta]-amyloid 1-42 levels, a main component of the amyloid plaques in Alzheimer's pathology, in the RVG-exosome-treated animals. The decrease observed was greater than the B-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the RNA-targeting system of the present invention to therapeutic targets, especially neurodegenerative diseases. A dosage of about 100 to 1000 mg of RNA-targeting system encapsulated in about 100 to 1000 mg of RVG exosomes may be contemplated for the present invention.

El-Andaloussi et al. (Nature Protocols 7,2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Qiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of RNA-targeting systeminto exosomes may be conducted similarly to siRNA. The exosomes may be co-cultured with monocytes and lymphocytes isolated from the peripheral blood of healthy donors. Therefore, it may be contemplated that exosomes containing RNA-targeting system may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi: 10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi: 10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi: 10.1155/2011/469679 for review).

A liposome formulation may be mainly comprised of natural phospholipids and lipids such as 1,2-distearoyl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi: 10.1155/2011/469679 for review).

In a particularly advantageous embodiment, Trojan Horse liposomes (also known as Molecular Trojan Horses) are desirable and protocols may be found at accessible at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the RNA-targeting system or complex to the brain via an intravascular injection, which would allow whole brain transgenic animals without the need for embryonic manipulation. About 1-5 g of DNA or RNA may be contemplated for in vivo administration in liposomes.

In another embodiment, the RNA-targetingsystem may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific RNA-targeting system targeted in a SNALP are contemplated. The daily treatment may be over about three days and then weekly for about five weeks. In another embodiment, a specific RNA-targeting system encapsulated (SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(@-methoxypoly (ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(@-methoxy poly(ethylene glycol) 2000) carbamoyl]-1,2-dimyristyloxypropylamine, and cationic 11,2-dilinoleyloxy-3-N,N-dimethylaminopropane (see, e.g., Geisbert et al., Lancet 2010; 375:1896-905). A dosage of about 2 mg/kg total RNA-targeting system per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-CDMA, and 1,2-dilinoleyloxy-3-(N,N-dimethyl) aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)-both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at>0.4 mg/kg; all responded to slowing of the infusion rate and all continued on study. Minimal and transient elevations of serum cytokines IL-6, IP-10 and IL-Ira were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the RNA-targeting system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate RNA-targeting system or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis (octadecyloxy) propyl-1-(methoxy poly(ethylene glycol) 2000) propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11+0.04 (n=56), the particles may be extruded up to three times through 80 nm membranes prior to adding the RNA-targeting guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume: 29, Pages: 154-157 (2011)) describes the use of lipid envelopes to deliver RNA. Use of lipid envelopes is also preferred in the present invention.

In another embodiment, lipids may be formulated with the RNA-targeting system of the present invention or component(s) thereof or nucleic acid molecule(s) coding therefor to form lipid nanoparticles (LNPs). Lipids include, but are not limited to, DLin-KC2-DMA4, C12-200 and colipids distearoylphosphatidyl choline, cholesterol, and PEG-DMG may be formulated with RNA-targeting system instead of siRNA (see, e.g., Novobrantseva, Molecular Therapy-Nucleic Acids (2012) 1, e4; doi: 10.1038/mtna.2011.3) using a spontaneous vesicle formation procedure. The component molar ratio may be about 50/10/38.5/1.5 (DLin-KC2-DMA or C12-200/distearoylphosphatidyl choline/cholesterol/PEG-DMG). The final lipid: siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915, 399; 8,236,943 and 7,838,658 and European Pat. Nos 1766035; 1519714; 1781593 and 1664316), all of which may be used and/or adapted to the present invention.

The RNA-targetingsystem or components thereof or nucleic acid molecule(s) coding therefor may be delivered encapsulated in PLGA Microspheres such as that further described in US published applications Ser. No. 20/130, 252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid: fusogenic lipid: cholesterol: PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application No. 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26;7 (2): 1016-26; Uchegbu and Siew, 2013, J Pharm Sci. 102 (2): 305-10 and Lalatsa et al., 2012, J Control Release. 2012 Jul. 20; 161 (2): 523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropyleneimine dendrimers start from a diaminobutane core to which is added twice the number of amino groups by a double Michael addition of acrylonitrile to the primary amines followed by the hydrogenation of the nitriles. This results in a doubling of the amino groups. Polypropyleneimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine and phosphorous containing compounds with a mixture of amine/amide or N--P($O_2$)S as the conjugating units respectively with no work being reported on the use of the lower generation polypropyleneimine dendrimers for gene delivery. Polypropyleneimine dendrimers have also been studied as pH sensitive controlled release systems for drug delivery and for their encapsulation of guest molecules when chemically modified by peripheral amino acid groups. The cytotoxicity and interaction of polypropyleneimine dendrimers with DNA as well as the transfection efficacy of DAB 64 has also been studied.

US Patent Publication No. 20050019923 is based upon the observation that, contrary to earlier reports, cationic dendrimers, such as polypropyleneimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application No. 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of RNA-targetingsystem(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of RNA-targetingsystem(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified+36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and RNA should be performed to optimize the procedure for specific cell lines.

(1) One day before treatment, plate $1\times10^5$ cells per well in a 48-well plate.

(2) On the day of treatment, dilute purified+36 GFP protein in serumfree media to a final concentration 200 nM. Add RNA to a final concentration of 50 nM. Vortex to mix and incubate at room temperature for 10 min.

(3) During incubation, aspirate media from cells and wash once with PBS.

(4) Following incubation of +36 GFP and RNA, add the protein-RNA complexes to cells.

(5) Incubate cells with complexes at 37° C. for 4 h.

(6) Following incubation, aspirate the media and wash three times with 20 U/mL heparin PBS. Incubate cells with serum-containing media for a further 48 h or longer depending upon the assay for activity.

(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more+36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1\times10^5$ per well in a 48-well plate.

(2) On the day of treatment, dilute purified p36 GFP protein in serumfree media to a final concentration 2 mM. Add 1 mg of plasmid DNA. Vortex to mix and incubate at room temperature for 10 min.

(3) During incubation, aspirate media from cells and wash once with PBS.

(4) Following incubation of p36 GFP and plasmid DNA, gently add the protein-DNA complexes to cells.

(5) Incubate cells with complexes at 37° C. for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the RNA-targeting system of the present invention. These systems of Dr. Lui and documents herein in conjunction with herein teachings can be employed in the delivery of RNA-targeting system(s) or component(s) thereof or nucleic acid molecule(s) coding therefor.

Implantable Devices

In another embodiment, implantable devices are also contemplated for delivery of the RNA-targeting system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used and/or adapted to the RNA-targeting system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m3 to 1000 mm$^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and/or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear--auditory system, labyrinth of the inner ear, vestibular system; 11. Intra tracheal; 12. Intracardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises an RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the RNA-targeting system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the RNA-targeting system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the RNA-targeting system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the RNA-targeting system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Patient-Specific Screening Methods

An RNA-targeting system that targets RNA, e.g., trinucleotide repeats can be used to screen patients or patent samples for the presence of such repeats. The repeats can be the target of the RNA of the RNA-targeting system, and if there is binding thereto by the RNA-targeting system, that binding can be detected, to thereby indicate that such a repeat is present. Thus, an RNA-targeting system can be used to screen patients or patient samples for the presence of the repeat. The patient can then be administered suitable compound(s) to address the condition; or, can be administed an RNA-targeting system to bind to and cause insertion, deletion or mutation and alleviate the condition.

Nucleic Acids, Amino Acids and Proteins, Regulatory Sequences, Vectors, Etc

Nucleic acids, amino acids and proteins: The invention uses nucleic acids to bind target RNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the invention the term "RNA-targeting guide RNA", refers to the polynucleotide sequence comprising the RNA-targeting tracr sequence and the RNA-targeting sca sequence.

As used herein the term "wild type" is a term of the art understood by skilled persons and means the typical form of an organism, strain, gene or characteristic as it occurs in nature as distinguished from mutant or variant forms. A "wild type" can be a base line.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point (Tm). The Tm is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the Tm. In order to require at least about 70% nucleotide complementarity of hybridized sequences, moderately-stringent washing conditions are selected to be about 15 to 30° C. lower than the Tm. Highly permissive (very low stringency) washing conditions may be as low as 50° C. below the Tm, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as IRNA genes or tRNA genes, the product is functional RNA. The process of gene expression is used by all known life-eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A.; Devereux et al., 1984, Nucleic Acids Research 12:387). Examples of other software than may perform sequence comparisons include, but are not limited to, the BLAST package (see Ausubel et al., 1999 ibid-Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible-reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4th Ed.-Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177 (1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins DG & Sharp PM (1988), Gene 73 (1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C.D. and Barton G.J. (1993) "Protein sequence alignments: a strategy for the hierarchical analysis of residue conservation" ('omput. Appl. Biosci. 9:745-756) (Taylor W.R. (1986) "The classification of amino acid conservation" J. Theor. Biol. 119; 205-218). Conservative substitutions may be made, for example according to the table below which describes a generally accepted Venn diagram grouping of amino acids.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M.J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), p pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or B-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell DC, Trends Biotechnol. (1995) 13(4), 132-134.

For purpose of this invention, amplification means any method employing a primer and a polymerase capable of replicating a target sequence with reasonable fidelity. Amplification may be carried out by natural or recombinant DNA polymerases such as AmpliTaq Gold™, T7 DNA polymerase, Klenow fragment of *E. coli* DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for RNA-targeting Cas protein (such as FinCas9) and RNA-targeting guide RNA. Bicistronic expression vectors for RNA-targeting Cas protein (such as FinCas9) and RNA-targeting guide RNA are preferred. In general and particularly in this embodiment RNA-targeting Cas protein (such as InCas9) is preferably driven by the CBh promoter. The RNA-targeting guide RNA may preferably be driven by a Pol III promoter, such as a U6 promoter. Ideally the two are combined. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U 5" segment in LTR of HTLV-I (Mol. Cell. Biol., Vol. 8 (1), p. 466-472, 1988); SV40 enhancer; and the intron sequence between exons 2 and 3 of rabbit B-globin (Proc. Natl. Acad. Sci. USA., Vol. 78 (3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g., nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccha-* romyces cerevisiae include pYepSecl (Baldari, et al., 1987. EMBO J. 6:229-234), pMFa (Kuijan and Herskowitz, 1982. (el/30:933-943), pJRY88 (Schultz et al., 1987. Gene 54:113-123), pYES2 (Invitrogen Corporation, San Diego, Calif.), and picZ (In Vitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3:2156-2165) and the pVL series (Luckow and Summers, 1989. Virology 170:31-39).

In some embodiments, a vector is capable of driving expression of one or more sequences in mammalian cells using a mammalian expression vector. Examples of mammalian expression vectors include pCDM8 (Seed, 1987. Nature 329:840) and pMT2PC (Kaufman, et al., 1987. EMBO) J. 6:187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1:268-277), lymphoid-specific promoters (Calame and Eaton, 1988. Adv. Immunol. 43:235-275), in particular promoters of T cell receptors (Winoto and Baltimore, 1989. EMBO) J. 8:729-733) and immunoglobulins (Baneiji, et al., 1983. Cell 33:729-740; Queen and Baltimore, 1983. (el/33:741-748), neuron-specific promoters (e.g., the neurofilament promoter; Byrne and Ruddle, 1989. Proc. Natl. Acad. Sci. USA 86:5473-5477), pancreas-specific promoters (Edlund, et al., 1985. Science 230:912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249:374-379) and the α-fetoprotein promoter (Campes and Tilghman, 1989. Genes Dev. 3:537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Inte.g. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "RNA-targeting system" as used in the present application refers collectively to transcripts and other elements involved in the expression of or directing the activity of RNA-targeting CRISPR-associated ("Cas") genes, including sequences encoding an RNA-targeting Cas protein and an RNA-targeting guide RNA (comprising an RNA-targeting small CRISPR/Cas system associated RNA (scaRNA) sequence and an RNA-targeting trans-activating CRISPR/Cas system RNA (tracrRNA) sequence), or other sequences and transcripts from an RNA-targeting CRISPR locus. In some embodiments, one or more elements of an RNA-targeting system are derived from a type I, type II, or type III RNA-targeting CRISPR system. In some embodiments, one or more elements of an RNA-targeting system is derived from a particular organism comprising an endogenous RNA-targeting CRISPR system, such as *Francisella novicida*. In general, an RNA-targeting system is characterized by elements that promote the formation of an RNA-targeting complex at the site of a target sequence. In the context of formation of an RNA-targeting complex, "target sequence" refers to a sequence to which a guide sequence is designed to have complementarity, where hybridization between a target sequence and an RNA-targeting guide RNA promotes the formation of an RNA-targeting complex. Full complementarity is not necessarily required, provided there is sufficient complementarity to cause hybridization and promote formation of an RNA-targeting complex. A target sequence may comprise RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing RNA" or "editing sequence". In aspects of the invention, an exogenous template RNA may be referred to as an editing template. In an aspect of the invention the recombination is homologous recombination.

Typically, in the context of an endogenous RNA-targeting system, formation of an RNA-targeting complex (comprising an RNA-targeting guide RNA hybridized to a target sequence and complexed with one or more RNA-targeting Cas proteins) results in cleavage of one or both RNA strands in or near (e.g. within 1, 2, 3, 4, 5, 6, 7, 8, 9, 10, 20, 50, or more base pairs from) the target sequence. In some embodiments, one or more vectors driving expression of one or more elements of an RNA-targeting system are introduced into a host cell such that expression of the elements of the RNA-targeting system direct formation of an RNA-targeting complex at one or more target sites. For example, an RNA-targeting Cas enzyme and an RNA-targeting guide RNA could each be operably linked to separate regulatory elements on separate vectors. Alternatively, two or more of the elements expressed from the same or different regulatory elements, may be combined in a single vector, with one or more additional vectors providing any components of the RNA-targeting system not included in the first vector. RNA-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding an RNA-targeting Cas protein and an RNA-targeting guide RNA embedded within one or more intron sequences (e.g. each in a different intron, two or more in at least one intron, or all in a single intron). In some embodiments, the RNA-targeting Cas protein and RNA-targeting guide RNA are operably linked to and expressed from the same promoter.

In general, a guide sequence is any polynucleotide sequence having sufficient complementarity with a target polynucleotide sequence to hybridize with the target sequence and direct sequence-specific binding of an RNA-targeting complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAST, Novoalign (Novocraft Technologies), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of an RNA-targeting complex to a target sequence may be assessed by any suitable assay. For example, the components of an RNA-targetingsystem sufficient to form an RNA-targeting complex, including the guide sequence to be tested, may be provided to a host cell having the corresponding target sequence, such as by transfection with vectors encoding the components of the RNA-targeting CRISPR sequence, followed by an assessment of preferential cleavage within the target sequence, such as by Surveyor assay as described herein. Similarly, cleavage of a target polynucleotide sequence may be evaluated in a test tube by providing the target sequence, components of an RNA-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a gene transcript or mRNA.

In some embodiments, the target sequence is a sequence within a genome of a cell.

In I some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A.R. Gruber et al., 2008, Cell 106 (1): 23-24; and PA Carr and GM Church, 2009, Nature Biotechnology 27 (12): 1151-62). Further algorithms may be found in U.S. application Ser. No. TBA; Broad Reference BI-2013/004A); incorporated herein by reference.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by an RNA-targeting Cas protein as a part of an RNA-targeting complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, the RNA-targeting Cas protein is part of a fusion protein comprising one or more heterologous protein domains (e.g., about or more than about 1, 2, 3, 4, 5, 6, 7, 8, 9, 10, or more domains in addition to the RNA-targeting Cas protein). An RNA-targeting Cas protein fusion protein may comprise any additional protein sequence, and optionally a linker sequence between any two domains. Examples of protein domains that may be fused to an RNA-targeting Cas protein include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). An RNA-targeting Cas protein may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising an RNA-targeting Cas protein are described in US20110059502, incorporated herein by reference. In some embodiments, a tagged RNA-targeting Cas protein is used to identify the location of a target sequence.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, an RNA-targeting Cas protein in combination with (and optionally complexed with) an RNA-targeting guide RNA is delivered to a cell. Conventional viral and non-viral based gene transfer methods can be used to introduce nucleic acids in mammalian cells or target tissues. Such methods can be used to administer nucleic acids encoding components of an RNA-targeting system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6 (10): 1149-1154 (1988); Vigne, Restorative Neurology and Neuroscience 8:35-36 (1995); Kremer & Perricaudet, British Medical Bulletin 51 (1): 31-44 (1995); Haddada et al., in Current Topics in Microbiology and Immunology, Doerfler and Böhm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid: nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human Immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994)). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and w2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CIR, Rat6, CVI, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr-/-, COR-L23, COR-L23/ CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of an RNA-targeting system as described herein (such as by transient transfection of one or more vectors, or transfection with RNA), and modified through the activity of an RNA-targeting complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In one aspect, the invention provides for methods of modifying a target polynucleotide in a eukaryotic cell. In some embodiments, the method comprises allowing an RNA-targeting complex to bind to the target polynucleotide to effect cleavage of said target polynucleotide thereby modifying the target polynucleotide, wherein the RNA-targeting complex comprises an RNA-targeting Cas protein complexed with an RNA-targeting guide RNA hybridized to a target sequence within said target polynucleotide.

In one aspect, the invention provides a method of modifying expression of a polynucleotide in a eukaryotic cell. In some embodiments, the method comprises allowing an RNA-targeting complex to bind to the polynucleotide such that said binding results in increased or decreased expression of said polynucleotide; wherein the RNA-targeting complex comprises an RNA-targeting Cas protein complexed with an RNA-targeting guide RNA hybridized to a target sequence within said polynucleotide.

With recent advances in crop genomics, the ability to use RNA-targeting systems to perform efficient and cost effective gene editing and manipulation will allow the rapid selection and comparison of single and multiplexed genetic manipulations to transform such genomes for improved production and enhanced traits. In this regard reference is made to US patents and publications: U.S. Pat. No. 6,603, 061-*Agrobacterium*-Mediated Plant Transformation Method; U.S. Pat. No. 7,868,149-Plant Genome Sequences and Uses Thereof and US 2009/0100536-Transgenic Plants with Enhanced Agronomic Traits, all the contents and disclosure of each of which are herein incorporated by reference in their entirety. In the practice of the invention, the contents and disclosure of Morrell et al "Crop genomics: advances and applications" Nat Rev Genet. 2011 Dec. 29;13 (2): 85-96 are also herein incorporated by reference in their entirety. In an advantageous embodiment of the invention, the RNA-targeting system is used to engineer microalgae (Example 15). Accordingly, reference herein to animal cells may also apply, mutatis mutandis, to plant cells unless otherwise apparent.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M.J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Modifying a Target

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant. For re-introduced cells it is particularly preferred that the cells are stem cells.

In some embodiments, the method comprises allowing an RNA-targeting complex to bind to the target polynucleotide to effect cleavage of said target polynucleotide thereby modifying the target polynucleotide, wherein the RNA-targeting complex comprises an RNA-targeting Cas protein complexed with an RNA-targeting guide RNA hybridized or hybridizable to a target sequence within said target polynucleotide.

In one aspect, the invention provides a method of modifying expression of a polynucleotide in a eukaryotic cell. In some embodiments, the method comprises allowing an RNA-targeting complex to bind to the polynucleotide such that said binding results in increased or decreased expression of said polynucleotide; wherein the RNA-targeting complex comprises an RNA-targeting Cas protein complexed with an RNA-targeting guide RNA hybridized or hybridizable to a target sequence within said polynucleotide. Similar considerations and conditions apply as above for methods of modifying a target polynucleotide. In fact, these sampling, culturing and re-introduction options apply across the aspects of the present invention.

Indeed, in any aspect of the invention, the RNA-targeting complex may comprise an RNA-targeting Cas protein complexed with an RNA-targeting guide RNA hybridized or hybridizable to a target sequence. Similar considerations and conditions apply as above for methods of modifying a target polynucleotide.

As described herein elsewhere, it will be apparent that in certain embodiments "modified", "altered", "manipulated" or like terms corresponds to alterations of target loci such as the activation or repression of the transcription of a gene, methylation or demethylation of CpG sites and the like, which may not require point mutations, deletions, substitutions, or insertions of one or more nucleotides at target loci. Furthermore as described herein elsewhere, it will also be apparent that reference to a CRISPR-Cas enzyme, including an RNA-targeting Cas protein, as "altering" or "modifying" or "manipulating" one or more target polynucleotide loci encompasses direct alteration or modification, e.g. via the catalytic activity of the enzyme itself but also indirect alteration or modification, e.g. via a catalytic activity associated with the CRISPR-Cas enzyme or an RNA-targeting Cas protein, such as via a heterologous functional domain, e.g. a transcriptional activation domain or e.g. via a catalytic activity of one or more heterologous functional domains associated with the guide RNA via a protein-binding aptamer, e.g. a transcriptional activation domain. In addition, as it will be appreciated it is intended that the one or more target polynucleotide loci which are "altered" or "modified" by the action of the CRISPR-Cas enzyme or RNA-targeting Cas protein may be comprised in or adjacent the polynucleotide sequence complementary to the guide sequence portion of a guide RNA, e.g. in embodiments wherein the alteration or modification is effected by the catalytic activity of the CRISPR-Cas enzyme or RNA-targeting Cas protein itself, e.g. cleavage of DNA by the nuclease activity of the CRISPR-Cas enzyme or Cas protein. However, also encompassed are embodiments wherein one or more target loci to be "altered" or "modified" are at a location distinct from the sequence complementary to the guide sequence portion of the guide RNA, e.g. in embodiments wherein the alteration or modification is effected via a heterologous functional domain associated with the CRISPR-Cas enzyme or Cas protein and/or guide RNA, e.g. activation or repression of the transcription of a gene. As such, "alteration" or "modification" (or analogous terms) of a target locus means via direct or indirect action of the CRISPR-Cas enzyme or Cas protein, and furthermore the "target locus" to be altered or modified and the "target sequence" which is complementary to the guide sequence portion of the guide RNA may or may not be the same.

In plants, pathogens are often host-specific. For example, *Fusarium oxysporum* f. sp. *lycopersici* causes tomato wilt but attacks only tomato, and *F. oxysporum* f. *dianthi Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

Kits

In one aspect, the invention provides kits containing any one or more of the elements disclosed in the above methods and compositions. In some embodiments, the kit comprises a vector system as taught herein and instructions for using the kit. Elements may be provide individually or in combinations, and may be provided in any suitable container, such as a vial, a bottle, or a tube. In some embodiments, the kit includes instructions in one or more languages, for example in more than one language. The instructions may be specific to the applications and methods described herein.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g., in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allows to provide all elements of the systems of the invention.

In one aspect, the invention provides methods for using one or more elements of an RNA-targeting system. The RNA-targeting complex of the invention provides an effective means for modifying a target polynucleotide. The RNA-targeting complex of the invention has a wide variety of utility including modifying (e.g., deleting, inserting, translocating, inactivating, activating) a target polynucleotide in a multiplicity of cell types. As such the RNA-targeting complex of the invention has a broad spectrum of applications in, e.g., gene therapy, drug screening, disease diagnosis, and prognosis.

The crystals of the RNA-targeting complex such as the RNA-targeting FnCas9 complex can be obtained by techniques of protein crystallography, including batch, liquid bridge, dialysis, vapor diffusion and hanging drop methods. Generally, the crystals of the invention are grown by dissolving substantially pure RNA-targeting complex and a nucleic acid molecule to which it binds in an aqueous buffer containing a precipitant at a concentration just below that necessary to precipitate. Water is removed by controlled evaporation to produce precipitating conditions, which are maintained until crystal growth ceases. The crystal structure information is described in U.S. provisional applications 61/915,251 filed Dec. 12, 2013, 61/930,214 filed on Jan. 22, 2014, 61/980,012 filed Apr. 15, 2014; and Nishimasu et al, "Crystal Structure of Cas9 in Complex with Guide RNA and Target DNA," Cell 156 (5): 935-949, DOI: accessible at dx.doi.org/10.1016/j.cell.2014.02.001 (2014), each and all of which are incorporated herein by reference.

Uses of the Crystals, Crystal Structure and Atomic Structure Co-Ordinates: The crystals of the RNA-targeting complex such as the RNA-targeting FnCas9 complex, and particularly the atomic structure co-ordinates obtained therefrom, have a wide variety of uses. The crystals and structure co-ordinates are particularly useful for identifying compounds (nucleic acid molecules) that bind to RNA-targeting complexes such as the RNA-targeting FnCas9 complex, and RNA-targeting complexes that can bind to particular compounds (nucleic acid molecules). Thus, the structure co-ordinates described herein can be used as phasing models in determining the crystal structures of additional synthetic or mutated RNA-targeting complexes such as the RNA-targeting FnCas9 complex, FnCas9, nickases, binding domains. The provision of the crystal structure of RNA-targeting complexes such as the RNA-targeting FnCas9 complex complexed with a nucleic acid molecule as applied in conjunction with the herein teachings provides the skilled artisan with a detailed insight into the mechanisms of action of RNA-targeting complexes such as the RNA-targeting FnCas9 complex. This insight provides a means to design modified RNA-targeting complexes, such as by attaching thereto a functional group, such as a repressor or activator. While one can attach a functional group such as a repressor or activator to the N or C terminal of RNA-targeting complexes, the crystal structure demonstrates that the N terminal seems obscured or hidden, whereas the C terminal is more available for a functional group such as repressor or activator. Attachment can be via a linker, e.g., a flexible glycine-serine (GlyGlyGlySer (SEQ ID NO: 23)) or (GGGS) 3 (SEQ ID NO: 28) or a rigid alpha-helical linker such as (Ala (GluAlaAlaAlaLys) Ala) (SEQ ID NO: 29). In addition to the flexible loop there is also a nuclease or H3 region, an H2 region and a helical region. By "helix" or "helical", is meant a helix as known in the art, including, but not limited to an alpha-helix. Additionally, the term helix or helical may also be used to indicate a c-terminal helical element with an N-terminal turn.

The provision of the crystal structure of RNA-targeting complex such as RNA-targeting F'nCas9 complex complexed with a nucleic acid molecule allows a novel approach for drug or compound discovery, identification, and design for compounds that can bind to RNA-targeting complexes and thus the invention provides tools useful in diagnosis, treatment, or prevention of conditions or diseases of multicellular organisms, e.g., algae, plants, invertebrates, fish, amphibians, reptiles, avians, mammals; for example domesticated plants, animals (e.g., production animals such as swine, bovine, chicken; companion animal such as felines, canines, rodents (rabbit, gerbil, hamster); laboratory animals such as mouse, rat), and humans.

In any event, the determination of the three-dimensional structure of RNA-targeting complexes such as FnCas9 complex provides a basis for the design of new and specific nucleic acid molecules that bind to CRISPR-Cas 9 (e.g., FnCas9), as well as the design of new RNA-targeting CRISPR-Cas9 systems, such as by way of modification of the RNA-targeting CRISPR-Cas9 system to bind to various nucleic acid molecules, by way of modification of the RNA-targeting CRISPR-Cas9 system to have linked thereto to any one or more of various functional groups that may interact with each other, with the RNA-targeting CRISPR-Cas9 (e.g., an inducible system that provides for self-activation and/or self-termination of function), with the nucleic acid molecule nucleic acid molecules (e.g., the functional group may be a regulatory or functional domain which may be selected from the group comprising, consisting essentially of, or consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase; and, in some aspects, the functional domain is an epigenetic regulator; see, e.g., Zhang et al., U.S. Pat. No. 8,507,272, and it is again mentioned that it and all documents cited herein and all appln. cited documents are hereby incorporated herein by reference), by way of modification of Cas9, by way of novel nickases. Indeed, the RNA-targeting CRISPR-Cas9 (FnCas9) crystal structure has a multitude of uses. For example, from knowing the three-dimensional structure of RNA-targeting CRISPR-Cas9 (FnCas9) crystal structure, computer modelling programs may be used to design or identify different molecules expected to interact with possible or confirmed sites such as binding sites or other structural or functional features of the RNA-targeting CRISPR-Cas9 system (e.g., FnCas9). Compound that potentially bind ("binder") can be examined through the use of computer modeling using a docking program. Docking programs are known; for example GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders ascertain how well the shape and the chemical structure of the potential binder will bind to an RNA-targeting CRISPR-Cas9 system (e.g., FnCas9). Computer-assisted, manual examination of the active site or binding site of an RNA-targeting CRISPR-Cas9 system (e.g., FnCas9) may be performed. Programs such as GRID (P. Goodford, J. Med. Chem, 1985, 28, 849-57)-a program that determines probable interaction sites between molecules with various functional groups—may also be used to analyze the active site or binding site to predict partial structures of binding compounds. Computer programs can be employed to estimate the attraction, repulsion or steric hindrance of the two binding partners, e.g., RNA-targeting CRISPR-Cas9 system (e.g., FnCas9) and a candidate nucleic acid molecule or a nucleic acid molecule and a candidate RNA-targeting CRISPR-Cas9 system (e.g., FnCas9); and the RNA-targeting CRISPR-Cas9 crystal structure (FnCas9) enables such methods. Generally, the tighter the fit, the fewer the steric hindrances, and the greater the attractive forces, the more potent the potential binder, since these properties are consistent with a tighter binding constant. Furthermore, the more specificity in the design of a candidate RNA-targeting CRISPR-Cas9 system (e.g., FnCas9), the more likely it is that it will not interact with off-target molecules as well. Also, "wet" methods are enabled by the instant invention. For example, in an aspect, the invention provides for a method for determining the structure of a binder (e.g., target nucleic acid molecule) of a candidate CRISPR-Cas9 system (e.g., FnCas9) bound to the candidate RNA-targeting CRISPR-Cas9 system (e.g., FnCas9), said method comprising, (a) providing a first crystal of a candidate RNA-targeting CRISPR-Cas9 system (FnCas9) according to the invention or a second crystal of a candidate RNA-targeting CRISPR-Cas9 system (e.g., FnCas9), (b) contacting the first crystal or second crystal with said binder under conditions whereby a complex may form; and (c) determining the structure of said candidate (e.g., CRISPR-Cas9 system (e.g., FnCas9) or CRISPR-Cas9 system (FnCas9) complex. The second crystal may have essentially the same coordinates discussed herein, however due to minor alterations in RNA-targeting CRISPR-Cas9 system (e.g., from the Cas9 of such a system being e.g., FnCas9 versus being FnCas9), wherein "e.g., FnCas9" indicates that the Cas9 is a Cas9 and can be of or derived from *Francisella novicida* or an ortholog thereof), the crystal may form in a different space group.

The invention further involves, in place of or in addition to "in silico" methods, other "wet" methods, including high throughput screening of a binder (e.g., target nucleic acid molecule) and a candidate RNA-targeting CRISPR-Cas9 system (e.g., FnCas9), or a candidate binder (e.g., target nucleic acid molecule) and an RNA-targeting CRISPR-Cas9 system (e.g., FnCas9), or a candidate binder (e.g., target nucleic acid molecule) and a candidate RNA-targeting CRISPR-Cas9 system (e.g., FnCas9) (the foregoing CRISPR-Cas9 system(s) with or without one or more functional group(s)), to select compounds with binding activity. Those pairs of binder and RNA-targeting CRISPR-Cas9 system which show binding activity may be selected and further crystallized with the RNA-targeting CRISPR-Cas9 crystal having a structure herein, e.g., by co-crystallization or by soaking, for X-ray analysis. The resulting X-ray structure may be compared with that of the Cas9 Crystal Structure for a variety of purposes, e.g., for areas of overlap. Having designed, identified, or selected possible pairs of binder and RNA-targeting CRISPR-Cas9 system by determining those which have favorable fitting properties, e.g., predicted strong attraction based on the pairs of binder and RNA-targeting CRISPR-Cas9 crystal structure data herein, these possible pairs can then be screened by "wet" methods for activity. Consequently, in an aspect the invention can involve: obtaining or synthesizing the possible pairs; and contacting a binder (e.g., target nucleic acid molecule) and a candidate RNA-targeting CRISPR-Cas9 system (e.g., FnCas9), or a candidate binder (e.g., target nucleic acid molecule) and an RNA-targeting CRISPR-Cas9 system (e.g., FnCas9), or a candidate binder (e.g., target nucleic acid molecule) and a candidate RNA-targeting CRISPR-Cas9 system (e.g., FnCas9) (the foregoing CRISPR-Cas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex(es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate RNA-targeting CRISPR-Cas9 system or components thereof. These steps may be repeated and re-repeated as necessary. Alternatively or additionally, potential RNA-targeting CRISPR-Cas9 systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom.

The invention further involves a method of determining three dimensional structures of RNA-targeting systems or complex(es) of unknown structure by using the structural co-ordinates of the Cas9 Crystal Structure. For example, if X-ray crystallographic or NMR spectroscopic data are provided for an RNA-targeting system or complex of unknown crystal structure, the structure of an RNA-targeting complex may be used to interpret that data to provide a likely structure for the unknown system or complex by such techniques as by phase modeling in the case of X-ray crystallography. Thus, an inventive method can comprise: aligning a representation of the RNA-targeting system or complex having an unknown crystal structure with an analogous representation of the RNA-targeting CRISPR-cas (9) system and complex of the crystal structure herein to match homologous or analogous regions (e.g., homologous or analogous sequences); modeling the structure of the matched homologous or analogous regions (e.g., sequences) of the RNA-targeting system or complex of unknown crystal structure based on the structure of the Cas9 Crystal Structure of the corresponding regions (e.g., sequences); and, determining a conformation (e.g., taking into consideration favorable interactions should be formed so that a low energy conformation is formed) for the unknown crystal structure which substantially preserves the structure of said matched homologous regions. "Homologous regions" describes, for example as to amino acids, amino acid residues in two sequences that are identical or have similar, e.g., aliphatic, aromatic, polar, negatively charged, or positively charged, side-chain chemical groups. Homologous regions as or nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art. Homology modeling is a technique that is well known to those skilled in the art (see, e.g., Greer, Science vol. 228 (1985) 1055, and Blundell et al. Eur J Biochem vol 172 (1988), 513). The computer representation of the conserved regions of the RNA-targeting CRISPR-Cas9 crystal structure and those of an RNA-targeting system of unknown crystal structure aid in the prediction and determination of the crystal structure of the RNA-targeting system of unknown crystal structure.

Further still, the aspects of the invention which employ the CRISPR-Cas9 crystal structure in silico may be equally applied to new RNA-targeting crystal structures divined by using the herein-referenced CRISPR-Cas9 crystal structure. In this fashion, a library of RNA-targeting complex crystal structures can be obtained. Rational RNA-targeting system design is thus provided by the instant invention. For instance, having determined a conformation or crystal structure of an RNA-targeting system or complex, by the methods described herein, such a conformation may be used in a computer-based method herein for determining the conformation or crystal structure of other RNA-targeting systems or complexes whose crystal structures are yet unkown. Data from all of these crystal structures can be in a database, and the herein methods can be more robust by having herein comparisons involving the herein crystal structure or portions thereof be with respect to one or more crystal structures in the library. The invention further provides systems, such as computer systems, intended to generate structures and/or perform rational design of an RNA-targeting system or complex. The system can contain: atomic co-ordinate data according to the herein-referenced Crystal Structure or be derived therefrom e.g., by modeling, said data defining the three-dimensional structure of an RNA-targeting system or complex or at least one domain or sub-domain thereof, or structure factor data therefor, said structure factor data being derivable from the atomic co-ordinate data of the herein-referenced Crystal Structure. The invention also involves computer readable media with: atomic co-ordinate data according to the herein-referenced Crystal Structure or derived therefrom e.g., by homology modeling, said data defining the three-dimensional structure of an RNA-targeting system or complex or at least one domain or sub-domain thereof, or structure factor data therefor, said structure factor data being derivable from the atomic co-ordinate data of the herein-referenced Crystal Structure. "Computer readable media" refers to any media which can be read and accessed directly by a computer, and includes, but is not limited to: magnetic storage media; optical storage media; electrical storage media; cloud storage and hybrids of these categories. By providing such computer readable media, the atomic co-ordinate data can be routinely accessed for modeling or other "in silico" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of RNA-targeting systems or complexes; advantageously, the three-dimensional structure being as defined by the atomic co-ordinate data according to the herein-referenced Crystal Structure. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The herein-referenced Crystal Structure gives atomic co-ordinate data for a CRISPR-Cas9 (S. pyogenes), and lists each atom by a unique number; the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms2) which accounts for movement of the atom around its atomic center, and atomic number.

In particular embodiments of the invention, the conformational variations in the crystal structures of the CRISPR-Cas9 system or of components of the CRISPR-Cas9 system provide important and critical information about the flexibility or movement of protein structure regions relative to nucleotide (RNA or DNA) structure regions that may be important for RNA-targeting system function. The structural information provided for Cas9 (e.g., F. novicida Cas9) as the CRISPR enzyme in the present application may be used to further engineer and optimize the RNA-targeting system and this may be extrapolated to interrogate structure-function relationships in other CRISPR enzyme systems as well. In particular embodiments of the invention, the crystal structure provides a critical step towards understanding the molecular mechanism of RNA-guided DNA targeting by Cas9. The structural and functional analyses herein provide a useful scaffold for rational engineering of Cas9-based genome modulating technologies and may provide guidance as to Cas9-mediated recognition of PAM sequences on the target DNA or mismatch tolerance between the sgRNA:DNA duplex. Aspects of the invention also relate to truncation mutants, e.g., an FnCas9 truncation mutant may facilitate packaging of Cas9 into size-constrained viral vectors for in vivo and therapeutic applications. Similarly, engineering of the PAM Interacting (PI) domain may allow programing of PAM specificity, improve target site recognition fidelity, and increase the versatility of the Cas9 genome engineering platform. Cas9 proteins may be engineered to alter their PAM specificity, for example as described in Kleinstiver BP et al. Engineered CRISPR-Cas9 nucleases with altered PAM specificities. Nature. 2015 Jul. 23;523 (7561): 481-5. doi: 10.1038/nature14592.

The structural information provided herein allows for interrogation of RNA-targeting guide RNA interaction with the target DNA and the RNA-targeting Cas protein (e.g., Cas9) permitting engineering or alteration of RNA-targeting guide RNA structure to optimize functionality of the entire RNA-targeting CRISPR-Cas system. For example, loops of the RNA-targeting guide RNA may be extended, without colliding with the RNA-targeting Cas protein by the insertion of distinct RNA loop(s) or disctinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: QB, F2, GA, fr, JP501, M12, R17, BZ13, JP34, JP500, KUI, M11, MX1, TW18, VK, SP, FI, ID2, NL95, TW19, AP205, 6Cb5, φCbSr, φCb12r, φCb23r, 7s and PRR1. These adaptor proteins or orthogonal RNA binding proteins can further recruit effector proteins or fusions which comprise one or more functional domains. In some embodiments, the functional domain may be selected from the group comprising, consisting essentially of, or consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (e.g. SID4X). In some embodiments, the functional domain is an epigenetic modifying domain, such that an epigenetic modifying enzyme is provided. In some embodiments, the functional domain is an activation domain, which may be the P65 activation domain.

In one aspect surveyor analysis is used for identification of indel activity/nuclease activity. In general survey analysis includes extraction of genomic DNA, PCR amplification of the genomic region flanking the CRISPR target site, purification of products, re-annealing to enable heteroduplex formation. After re-annealing, products are treated with SURVEYOR nuclease and SURVEYOR enhancer S (Transgenomics) following the manufacturer's recommended protocol. Analysis may be performed with polyacrylamide gels according to known methods. Quantification may be based on relative band intensities.

Crystallization of CRISPR-Cas9 and Characterization of Crystal Structure

The crystals of the Cas9 can be obtained by techniques of protein crystallography, including batch, liquid bridge, dialysis, vapor diffusion and hanging drop methods. Generally, the crystals of the invention are grown by dissolving substantially pure CRISPR-Cas9 and a nucleic acid molecule to which it binds in an aqueous buffer containing a precipitant at a concentration just below that necessary to precipitate. Water is removed by controlled evaporation to produce precipitating conditions, which are maintained until crystal growth ceases. The crystal structure information is described in U.S. provisional applications 61/915,251 filed Dec. 12, 2013, 61/930,214 filed on Jan. 22, 2014, 61/980, 012 filed Apr. 15, 2014; and Nishimasu et al, "Crystal Structure of Cas9 in Complex with Guide RNA and Target DNA," Cell 156 (5): 935-949, DOI: accessible at dx.doi.org/10.1016/j.cell.2014.02.001 (2014), and PCT/US14/70175; and Nishimasu H et al, Crystal Structure of *Staphylococcus aureus* Cas9. Cell. 2015 Aug. 27;162 (5): 1113-26. doi: 10.1016/j.cell.2015.08.007; each and all of which are incorporated herein by reference, and together are "herein cited materials" concerning the Cas9 crystal structure. Uses of the Crystals, Crystal Structure and Atomic Structure Co-Ordinates of the herein cited materials: The crystals of the Cas9, and particularly the atomic structure co-ordinates obtained therefrom, have a wide variety of uses. The crystals and structure co-ordinates are particularly useful for identifying compounds (nucleic acid molecules) that bind to CRISPR-Cas9, and CRISPR-Cas9s that can bind to particular compounds (nucleic acid molecules). Thus, the structure co-ordinates described herein can be used as phasing models in determining the crystal structures of additional synthetic or mutated CRISPR-Cas9s, Cas9s, nickases, binding domains. The provision of the crystal structure of CRISPR-Cas9 complexed with a nucleic acid molecule as applied in conjunction with the herein teachings provides the skilled artisan with a detailed insight into the mechanisms of action of CRISPR-Cas9. This insight provides a means to design modified CRISPR-Cas9s, such as by attaching thereto a functional group, such as a repressor or activator. While one can attach a functional group such as a repressor or activator to the N or C terminal of CRISPR-Cas9, the crystal structure demonstrates that the N terminal seems obscured or hidden, whereas the C terminal is more available for a functional group such as repressor or activator. Moreover, the crystal structure demonstrates that there is a flexible loop between approximately CRISPR-Cas9 (*S. pyogenes*) residues 534-676 which is suitable for attachment of a functional group such as an activator or repressor. Attachment can be via a linker, e.g., a flexible glycine-serine (GlyGlyGlySer (SEQ ID NO: 23)) or (GGGS) 3 (SEQ ID NO: 28) or a rigid alpha-helical linker such as (Ala (GluAlaAlaAlaLys) Ala) (SEQ ID NO: 29). In addition to the flexible loop there is also a nuclease or H3 region, an H2 region and a helical region. By "helix" or "helical", is meant a helix as known in the art, including, but not limited to an alpha-helix. Additionally, the term helix or helical may also be used to indicate a c-terminal helical element with an N-terminal turn. The provision of the crystal structure of CRISPR-Cas9 complexed with a nucleic acid molecule allows a novel approach for drug or compound discovery, identification, and design for compounds that can bind to CRISPR-Cas9 and thus the invention provides tools useful in diagnosis, treatment, or prevention of conditions or diseases of multicellular organisms, e.g., algae, plants, invertebrates, fish, amphibians, reptiles, avians, mammals; for example domesticated plants, animals (e.g., production animals such as swine, bovine, chicken; companion animal such as felines, canines, rodents (rabbit, gerbil, hamster); laboratory animals such as mouse, rat), and humans. The invention further involves, in place of or in addition to "in silico" methods, other "wet" methods, including high throughput screening of a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)), to select compounds with binding activity. Those pairs of binder and CRISPR-Cas9 system which show binding activity may be selected and further crystallized with the CRISPR-Cas9 crystal having a structure herein, e.g., by co-crystallization or by soaking, for X-ray analysis. The resulting X-ray structure may be compared with that of the Cas9 Crystal Structure for a variety of purposes, e.g., for areas of overlap. Having designed, identified, or selected possible pairs of binder and CRISPR-Cas9 system by determining those which have favorable fitting properties, e.g., predicted strong attraction based on the pairs of binder and CRISPR-Cas9 crystal structure data herein, these possible pairs can then be screened by "wet" methods for activity. Consequently, in an aspect the invention can involve: obtaining or synthesizing the possible pairs; and contacting a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex(es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate CRISPR-Cas9 system or components thereof. These steps may be repeated and re-repeated as necessary. Alternatively or additionally, potential CRISPR-Cas9 systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom. If X-ray crystallographic or NMR spectroscopic data are provided for a CRISPR-cas system or complex of unknown crystal structure, the structure of a CRISPR-Cas9 complex as defined of the herein cited materials may be used to interpret that data to provide a likely structure for the unknown system or complex by such techniques as by phase modeling in the case of X-ray crystallography. Thus, from this disclosure and the knowledge in the art one can perform a method comprising: aligning a representation of the CRISPR-cas system or complex having an unknown crystal structure with an analogous representation of the CRISPR-cas(9) system and complex of the crystal structure herein to match homologous or analogous regions (e.g., homologous or analogous sequences); modeling the structure of the matched homologous or analogous regions (e.g., sequences) of the CRISPR-cas system or complex of unknown crystal structure based on the structure of the Cas9 Crystal Structure of the corresponding regions (e.g., sequences); and, determining a conformation (e.g. taking into consideration favorable interactions should be formed so that a low energy conformation is formed) for the unknown crystal structure which substantially preserves the structure of said matched homologous regions. "Homologous regions" describes, for example as to amino acids, amino acid residues in two sequences that are identical or have similar, e.g., aliphatic, aromatic, polar, negatively charged, or positively charged, side-chain chemical groups. Homologous regions as ot nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art. Homology modeling is a technique that is well known to those skilled in the art (see, e.g., Greer, Science vol. 228 (1985) 1055, and Blundell et al. Eur J Biochem vol 172 (1988), 513). The computer representation of the conserved regions of the CRISPR-Cas9 crystral structure and those of a CRISPR-Cas system of unknown crystal structure aid in the prediction and determination of the crystal structure of the CRISPR-cas system of unknown crystal structure. The CRISPR-Cas9 crystal structure in silico may be equally applied to new CRISPR-cas crystal structures divined by using the teachings herein and the herein cited materials concerning the CRISPR-Cas9 crystal structure. In this fashion, a library of CRISPR-Cas crystal structures can be obtained. Rational CRISPR-Cas system design is thus provided by the instant invention. For instance, having obtained a CRISPR-Cas system or complex using teachings herein and determining a conformation or crystal structure of a CRISPR-Cas system or complex, such a conformation may be used in a computer-based methods herein for determining the conformation or crystal structure of other CRISPR-Cas systems or complexes whose crystal structures are yet unkown. Data from all of these crystal structures can be in a database, and the herein methods can be more robust by having herein comparisons involving the herein crystal structure or portions thereof be with respect to one or more crystal structures in the library. Thus, there is the provision of systems, such as computer systems, intended to generate structures and/or perform rational design of a CRISPR-Cas system or complex. The system can contain: atomic co-ordinate data according to the herein cited materials concerning the Cas9 Crystal Structure or be derived therefrom e.g., by modeling, said data defining the three-dimensional structure of a CRISPR-Cas system or complex or at least one domain or sub-domain thereof, or structure factor data therefor, said structure factor data being derivable from the atomic co-ordinate data of the herein-referenced Crystal Structure. The invention also involves computer readable media with: atomic co-ordinate data according to the teachings herein e.g., by or from homology modeling, said data defining the three-dimensional structure of a CRISPR-Cas system or complex or at least one domain or sub-domain thereof, or structure factor data therefor, said structure factor data being derivable from the atomic co-ordinate data of the herein-referenced Crystal Structure. "Computer readable media" refers to any media which can be read and accessed directly by a computer, and includes, but is not limited to: magnetic storage media; optical storage media; electrical storage media; cloud storage and hybrids of these categories.

By providing such computer readable media, the atomic co-ordinate data can be routinely accessed for modeling or other "in silico" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of CRISPR-Cas systems or complexes; advantageously, the three-dimensional structure being as defined by the atomic co-ordinate data according to the herein-referenced Crystal Structure. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The herein cited materials concerning the Crystal Structure gives atomic co-ordinate data for a CRISPR-Cas9 (*S. pyogenes*), and lists each atom by a unique number; the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms$^2$) which accounts for movement of the atom around its atomic center, and atomic number. The conformational variations in the crystal structures of the CRISPR-Cas9 system or of components of the CRISPR-Cas9 may provide important and critical information about the flexibility or movement of protein structure regions relative to nucleotide (RNA or DNA) structure regions that may be important for CRISPR-Cas system function. The structural information provided for Cas9 (e.g. *S. pyogenes* Cas9) as the CRISPR enzyme in the present application may be used to further engineer and optimize the CRISPR-Cas system and this may be extrapolated to interrogate structure-function relationships in other CRISPR enzyme systems as well. The herein cited materials relate to the crystal structure of *S. pyogenes* Cas9 in complex with sgRNA and its target DNA at 2.4 Å resolution. The structure revealed a bilobed architecture composed of target recognition and nuclease lobes, accommodating a sgRNA: DNA duplex in a positively-charged groove at their interface. The recognition lobe is essential for sgRNA and DNA binding and the nuclease lobe contains the HNH and RuvC nuclease domains, which are properly positioned for the cleavage of complementary and non-complementary strands of the target DNA, respectively. This high-resolution structure and the functional analyses provided herein elucidate the molecular mechanism of RNA-guided DNA targeting by Cas9, and provides an abundance of information for generating optimized CRISPR-Cas systems and components thereof. The crystal structure in conjunction with herein teachings may provide steps towards understanding the molecular mechanism of RNA-guided DNA targeting by Cas9. The structural and functional analyses of herein teachings and herein cited materials provide a useful scaffold for rational engineering of Cas9-based genome modulating technologies and may provide guidance as to Cas9-mediated recognition of PAM sequences on the target DNA or mismatch tolerance between the sgRNA: DNA duplex. Aspects of the invention may also relate to truncation mutants, e.g. an *S. pyogenes* Cas9 truncation mutant may facilitate packaging of Cas9 into size-constrained viral vectors for in vivo and therapeutic applications. Similarly, engineering of the PAM Interacting (PI) domain may allow programing of PAM specificity, improve target site recognition fidelity, and increase the versatility of the Cas9 genome engineering platform. Cas9 proteins may be engineered to alter their PAM specificity, for example as described in Kleinstiver BP et al. Engineered CRISPR-Cas9 nucleases with altered PAM specificities. Nature. 2015 Jul. 23;523 (7561): 481-5. doi: 10.1038/nature14592.

The invention comprehends optimized functional CRISPR-Cas enzyme systems. In particular the CRISPR enzyme comprises one or more mutations that converts it to a DNA binding protein to which ligase domains may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence.

The teachings herein and structural information of herein cited materials provided herein allows for interrogation of sgRNA (or chimeric RNA) interaction with the target DNA and the CRISPR enzyme (e.g. Cas9) permitting engineering or alteration of sgRNA structure to optimize functionality of the entire CRISPR-Cas system. For example, loops of the sgRNA may be extended, without colliding with the Cas9 protein by the insertion of distinct RNA loop(s) or disctinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: QB, F2, GA, fr, JP501, M12, R17, BZ13, JP34, JP500, KUI, M11, MX1, TW18, VK, SP, FI, ID2, NL95, TW19, AP205, 6Cb5, φCb8r, φCb12r, φCb23r, 7s and PRR1. These adaptor proteins or orthogonal RNA binding proteins can further recruit effector proteins or fusions which comprise one or more ligase domains.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publication US 2015-0031134 (U.S. application Ser. No. 14/497,627), which is allowed; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414, European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089486 (PCT/US2014/070175), 2015/089465 (PCT/US2014/070135), PCT/US2015/051691, PCT/US2015/051830. Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to US provisional patent application 61/836,123, filed on Jun. 17, 2013. Reference is additionally made to U.S. provisional patent applications 61/835,931, 61/835,936, 61/835,973, 61/836,080, 61/836,101, and 61/836,127, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT/US2014/62558 filed Oct. 28, 2014, and U.S. Provisional Patent Applications Ser. Nos. 61/915,148, 61/915,150, 61/915,153, 61/915,203, 61/915,251, 61/915,301, 61/915,267, 61/915,260, and 61/915,397, each filed Dec. 12, 2013; 61/757,972 and 61/768,959, filed on Jan. 29, 2013 and Feb. 25, 2013; 62/010,888 and 62/010,879, both filed Jun. 11, 2014; 62/010,329, 62/010,439 and 62/010,441, each filed Jun. 10, 2014; 61/939,228 and 61/939,242, each filed Feb. 12, 2014; 61/980,012, filed Apr. 15,2014; 62/038,358, filed Aug. 17, 2014; 62/055,484, 62/055,460 and 62/055,487, each filed Sep. 25, 2014; and 62/069,243, filed Oct. 27, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to PCT application designating, inter alia, the United States, application No. PCT/US14/41806, filed Jun. 10, 2014.

Mention is also made of US application 62/180,709, 17-Jun-15, PROTECTED GUIDE RNAS (PGRNAS); U.S. application 62/091,455, filed, 12-Dec-14, PROTECTED GUIDE RNAS (PGRNAS); U.S. application 62/096,708, 24-Dec-14, PROTECTED GUIDE RNAS (PGRNAS); U.S. applications 62/091,462, 12-Dec-14, 62/096,324, 23-Dec-14, 62/180,681, 17 Jun. 2015, and 62/237,496, 5 Oct. 2015, DEAD GUIDES FOR CRISPR TRANSCRIPTION FACTORS; U.S. application 62/091,456, 12-Dec-14 and 62/180,692, 17 Jun. 2015, ESCORTED AND FUNCTIONALIZED GUIDES FOR CRISPR-CAS SYSTEMS; U.S. application 62/091,461, 12-Dec-14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19-Dec-14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24-Dec-14, ENGINEERING OF SYSTEMS, METHODS AND OPTIMIZED ENZYME AND GUIDE SCAFFOLDS FOR SEQUENCE MANIPULATION; U.S. application 62/098,059, 30-Dec-14, 62/181,641, 18 Jun. 2015, and 62/181,667, 18 Jun. 2015, RNA-TARGETING SYSTEM; U.S. application 62/096,656, 24-Dec-14 and 62/181,151, 17 Jun. 2015, CRISPR HAVING OR ASSOCIATED WITH DESTABILIZATION DOMAINS; U.S. application 62/096,697, 24-Dec-14, CRISPR HAVING OR ASSOCIATED WITH AAV; US application 62/098,158, 30-Dec-14, ENGINEERED CRISPR COMPLEX INSERTIONAL TARGETING SYSTEMS; U.S. application 62/151,052, 22-Apr-15, CELLULAR TARGETING FOR EXTRACELLULAR EXOSOMAL REPORTING; U.S. application 62/054,490, 24-Sep-14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12-FEB-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25-Sep-14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4-Dec-14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24-Sep-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23-Oct-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24-Sep-14 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24-Sep-14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25-Sep-14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25-Sep-14, MULTIFUNCTIONAL-CRISPR COMPLEXES AND/OR OPTIMIZED ENZYME LINKED FUNCTIONAL-CRISPR COMPLEXES; U.S. application 62/087,475, 4-Dec-14 and 62/181,690, 18 Jun. 2015, FUNCTIONAL SCREENING WITH OPTIMIZED FUNCTIONAL CRISPR-CAS SYSTEMS; U.S. application 62/055,487, 25-Sep-14, FUNCTIONAL SCREENING WITH OPTIMIZED FUNCTIONAL CRISPR-CAS SYSTEMS; U.S. application 62/087,546, 4-Dec-14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30-Dec-14, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, and, filed 22 Oct. 2015, NOVEL CRISPR ENZYMES AND SYSTEMS, U.S. application 62/232,067, 24 Sep. 2015, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln. cited documents") and all documents cited or referenced in the appln. cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln. cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR Cas systems. Cong, L., Ran, F.A., Cox, D., Lin, S., Barretto, R., Habib, N., Hsu, P.D., Wu, X., Jiang, W., Marraffini, L.A., & Zhang, F. Science February 15;339 (6121): 819-23 (2013);

RNA-guided editing of bacterial genomes using CRISPR-Cas systems. Jiang W., Bikard D., Cox D., Zhang F, Marraffini LA. Nat Biotechnol Mar;31 (3): 233-9 (2013);

One-Step Generation of Mice Carrying Mutations in Multiple Genes by CRISPR Cas-Mediated Genome Engineering. Wang H., Yang H., Shivalila CS., Dawlaty MM., Cheng AW., Zhang F., Jaenisch R. Cell May 9;153 (4): 910-8 (2013);

Optical control of mammalian endogenous transcription and epigenetic states. Konermann S, Brigham MD, Trevino AE, Hsu PD, Heidenreich M, Cong L, Platt RJ, Scott DA, Church GM, Zhang F. Nature. 2013 Aug. 22;500 (7463): 472-6. doi: 10.1038/Nature12466. Epub 2013 Aug. 23;

Double Nicking by RNA-Guided CRISPR Cas9 for Enhanced Genome Editing Specificity. Ran, FA., Hsu, PD., Lin, CY., Gootenberg, JS., Konermann, S., Trevino, AE., Scott, DA., Inoue, A., Matoba, S., Zhang, Y., & Zhang, F. ('e//August 28. pii: S0092-8674 (13) 01015-5. (2013);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi: 10.1038/nbt.2647 (2013);

Genome engineering using the CRISPR-Cas9 system. Ran, FA., Hsu, PD., Wright, J., Agarwala, V., Scott, DA., Zhang, F. Nature Protocols Nov;8 (11): 2281-308. (2013);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013). [Epub ahead of print];

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27. (2014). 156 (5): 935-49;

Genome-wide binding of the CRISPR endonuclease Cas9 in mammalian cells. Wu X., Scott DA., Kriz AJ., Chiu AC., Hsu PD., Dadon DB., Cheng AW., Trevino AE., Konermann S., Chen S., Jaenisch R., Zhang F., Sharp PA. Nat Biotechnol. (2014) April 20. doi: 10.1038/nbt.2889, CRISPR-Cas9 Knockin Mice for Genome Editing and Cancer Modeling, Platt et al., Cell 159 (2): 440-455 (2014) DOI: 10.1016/j.cell.2014.09.014, Development and Applications of CRISPR-Cas9 for Genome Engineering, Hsu et al, Cell 157, 1262-1278 (Jun. 5, 2014) (Hsu 2014), Genetic screens in human cells using the CRISPR Cas9 system, Wang et al., Science. 2014 Jan. 3; 343 (6166): 80-84. doi: 10.1126/science.1246981, Rational design of highly active sgRNAs for CRISPR-Cas9-mediated gene inactivation, Doench et al., Nature Biotechnology published online 3 Sep. 2014; doi: 10.1038/nbt.3026, and In vivo interrogation of gene function in the mammalian brain using CRISPR-Cas9, Swiech et al, Nature Biotechnology; published online 19 Oct. 2014; doi: 10.1038/nbt.3055.

Genome-scale transcriptional activation by an engineered CRISPR-Cas9 complex, Konermann S, Brigham MD, Trevino AE, Joung J, Abudayyeh OO, Barcena C, Hsu PD, Habib N, Gootenberg JS, Nishimasu H, Nureki O, Zhang F., Nature. January 29;517 (7536): 583-8 (2015).

A split-Cas9 architecture for inducible genome editing and transcription modulation, Zetsche B, Volz SE, Zhang F., (published online 2 Feb. 2015) Nat Biotechnol. Feb;33 (2): 139-42 (2015);

Genome-wide CRISPR Screen in a Mouse Model of Tumor Growth and Metastasis, Chen S, Sanjana NE, Zheng K, Shalem O, Lee K, Shi X, Scott DA, Song J, Pan JQ, Weissleder R, Lee H, Zhang F, Sharp PA. Cell 160, 1246-1260 Mar. 12, 2015 (multiplex screen in mouse), and In vivo genome editing using *Staphylococcus aureus* Cas9, Ran FA, Cong L, Yan WX, Scott DA, Gootenberg JS, Kriz AJ, Zetsche B, Shalem O, Wu X, Makarova KS, Koonin EV, Sharp PA, Zhang F., (published online 1 Apr. 2015), Nature. April 9;520 (7546): 186-91 (2015).

High-throughput functional genomics using CRISPR-Cas9, Shalem et al., Nature Reviews Genetics 16, 299-311 (May 2015).

Sequence determinants of improved CRISPR sgRNA design, Xu et al., Genome Research 25, 1147-1157 (August 2015).

A Genome-wide CRISPR Screen in Primary Immune Cells to Dissect Regulatory Networks, Parnas et al., Cell 162, 675-686 (Jul. 30, 2015).

CRISPR Cas9 cleavage of viral DNA efficiently suppresses hepatitis B virus, Ramanan et al., Scientific Reports 5:10833. doi: 10.1038/srep10833 (Jun. 2, 2015).

Crystal Structure of *Staphylococcus aureus* Cas9, Nishimasu et al., Cell 162, 1113-1126 (Aug. 27, 2015).

BCL11A enhancer dissection by Cas9-mediated in situ saturating mutagenesis, Canver et al., Nature 527 (7577): 192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60 (3), 385-397 doi: 10.1016/j.molcel.2015.10.008 Epub Oct. 22, 2015.

Rationally engineered Cas9 nucleases with improved specificity, Slaymaker et al., Science 2015 Dec. 1. pii: aad5227. [Epub ahead of print]

each of which is incorporated herein by reference, and discussed briefly below:

Cong et al. engineered type II CRISPR/Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA: Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293 FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA: DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* (112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2cl and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2015) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Mention is also made of Tsai et al, "Dimeric CRISPR RNA-guided FokI nucleases for highly specific genome editing." Nature Biotechnology 32 (6): 569-77 (2014) which is not believed to be prior art to the instant invention or application, but which may be considered in the practice of the instant invention. Mention is also made of Konermann et al., "Genome-scale transcription activation by an engineered CRISPR-Cas9 complex," doi: 10.1038/nature 14136, incorporated herein by reference.

The present invention will be further illustrated in the following Examples which are given for illustration purposes only and are not intended to limit the invention in any way.

EXAMPLES

Example 1: Binding of In Vitro Transcribed sgRNA

The inventors assessed the ability of *Francisella novicida* Cas9 (FnCas9) to bind both native and chimeric RNAs in vitro. It was found that purified FnCas9 successfully bound in vitro transcribed scaRNA and tracrRNA, as well as fusion RNA. FnCas9's binding to native mRNA, with and without small RNAs, was also tested, and found that it successfully bound the native FTN 1103 mRNA (FIG. 1).

Example 2: Characterization of Endogenous scaRNA/tracrRNA Transcripts

Figure 2A:
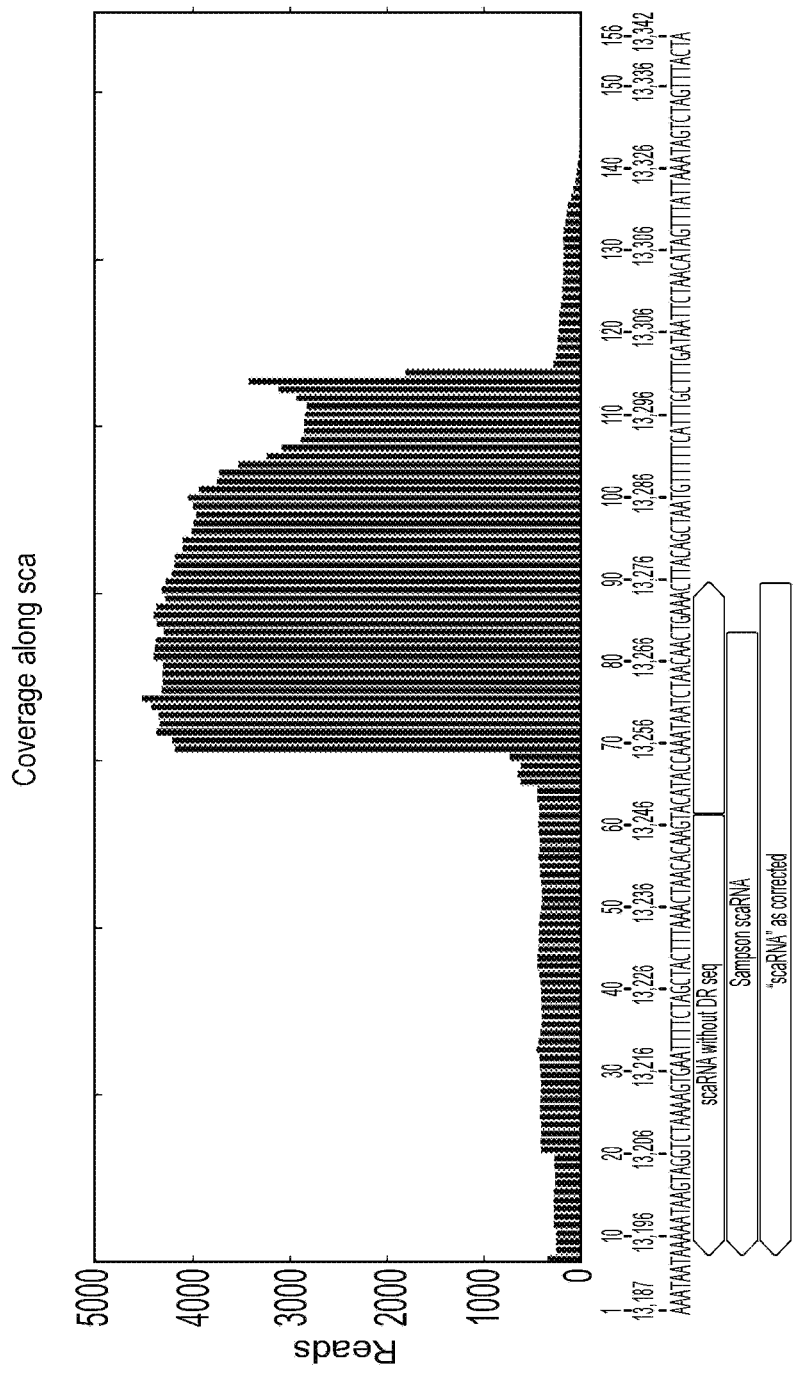
FIG. 2A-2B provides a graph representing the processing states of scaRNA as determined by RNA sequencing (SEQ ID NO: 35).
Figure 2B:
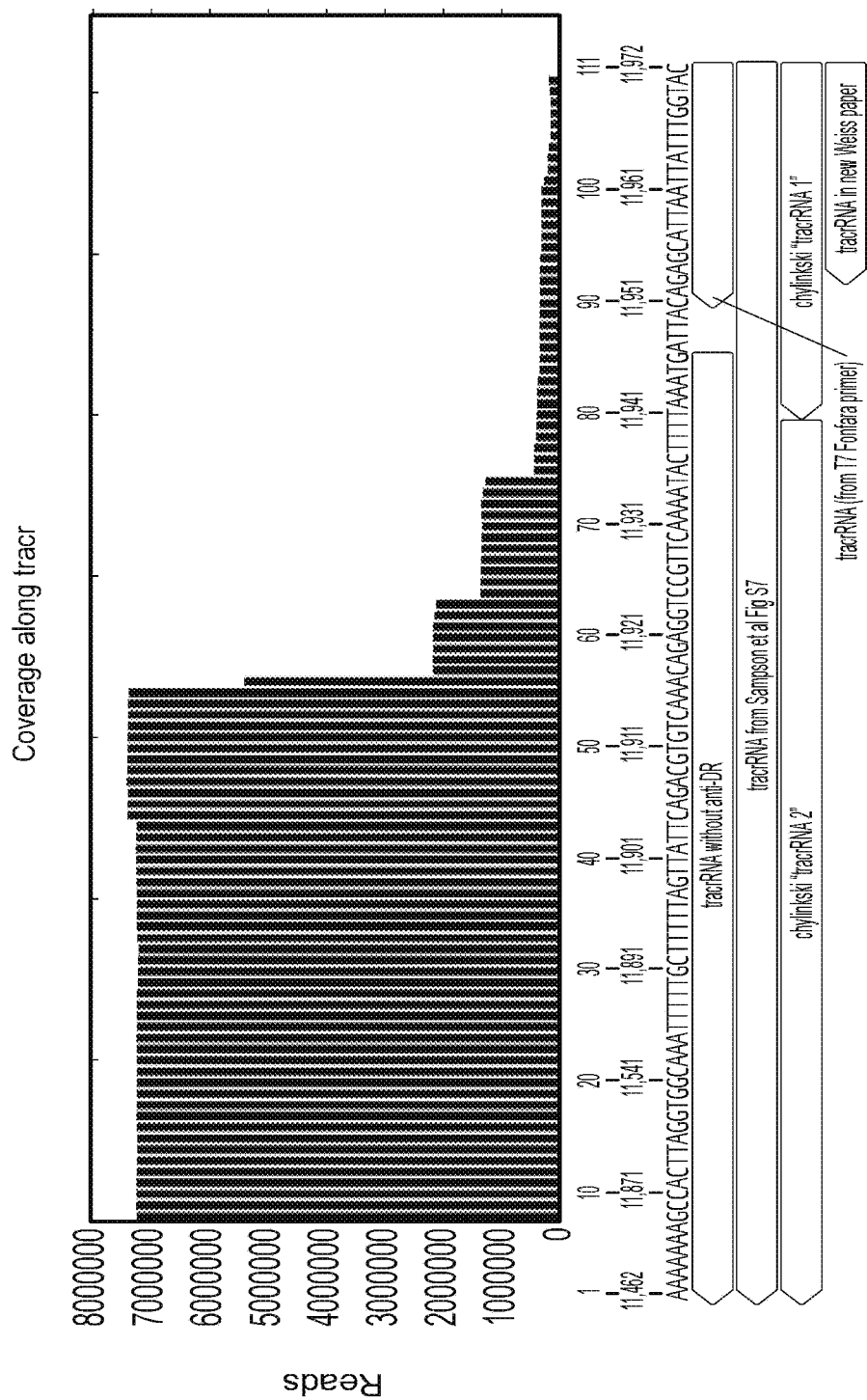

The CRISPR locus from *F. novicida* was expressed in *E. coli* and total RNA-seq was performed to characterize the endogenous scaRNA and tracrRNA transcripts. The scaRNA and tracrRNA were present and underwent several states of processing (FIG. 2). FIG. 2A provides a graph representing the processing states of scaRNA as determined by RNA sequencing (RNA seq). FIG. 2B provides a graph representing the processing states of tracrRNA as determined by RNA sequencing.

Example 3: Analysis of Expression of Exogenous FnCas9 in *E. coli*

Figure 3:
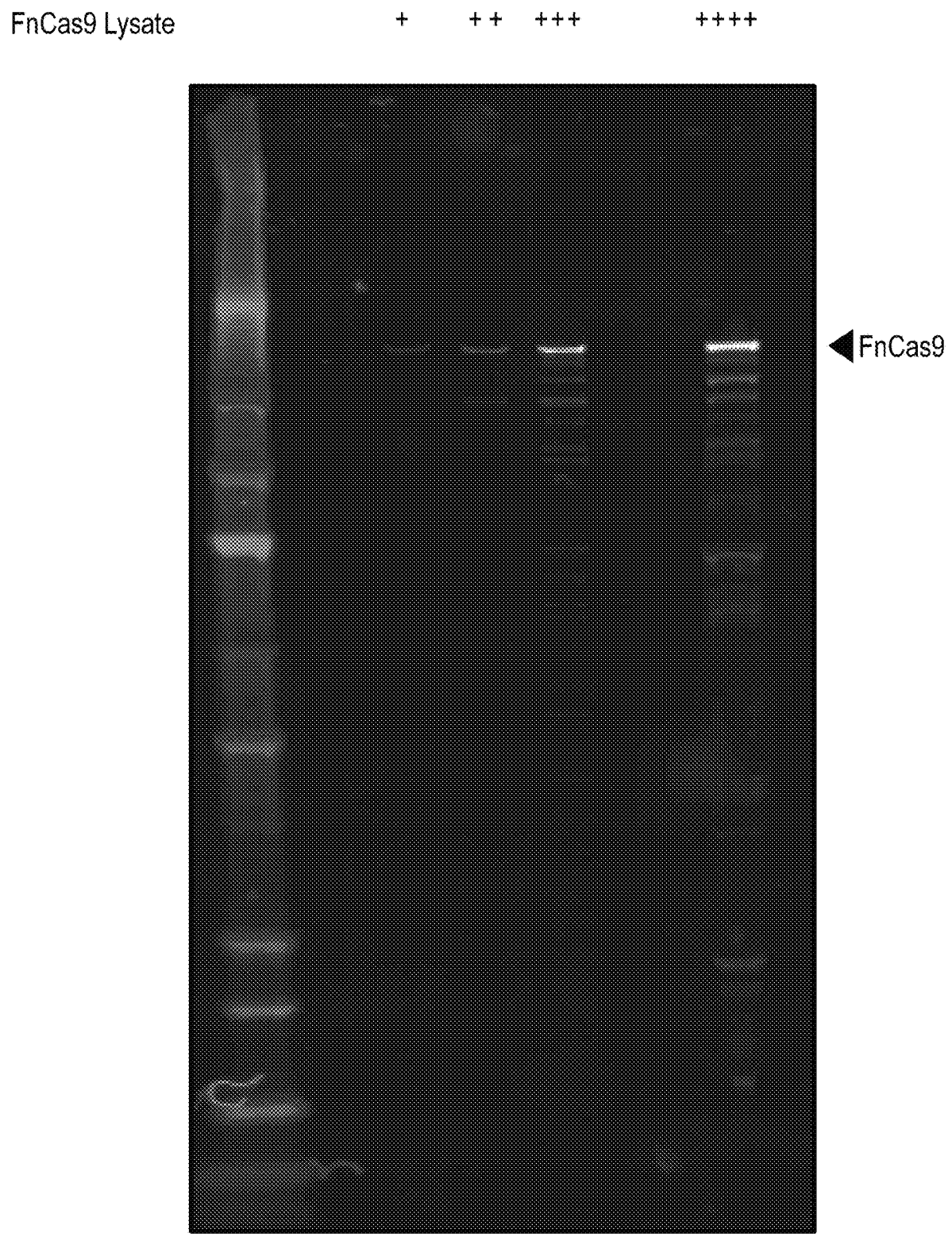
FIG. 3 provides a photograph of a Western blot showing FnCas9 expression in *E. coli*.

In order to test FnCas9's binding and cleavage in vivo, it was determined that the FnCas9 in the *Francisella novicida* CRISPR could be expressed from its native promoter in *E. coli*. Via Western blot, it was verified that full-length FnCas9 was expressed successfully (FIG. 3).

Example 4: Reconstitution of FnCas9 mRNA Cleavage in *E. coli*

Figure 4:
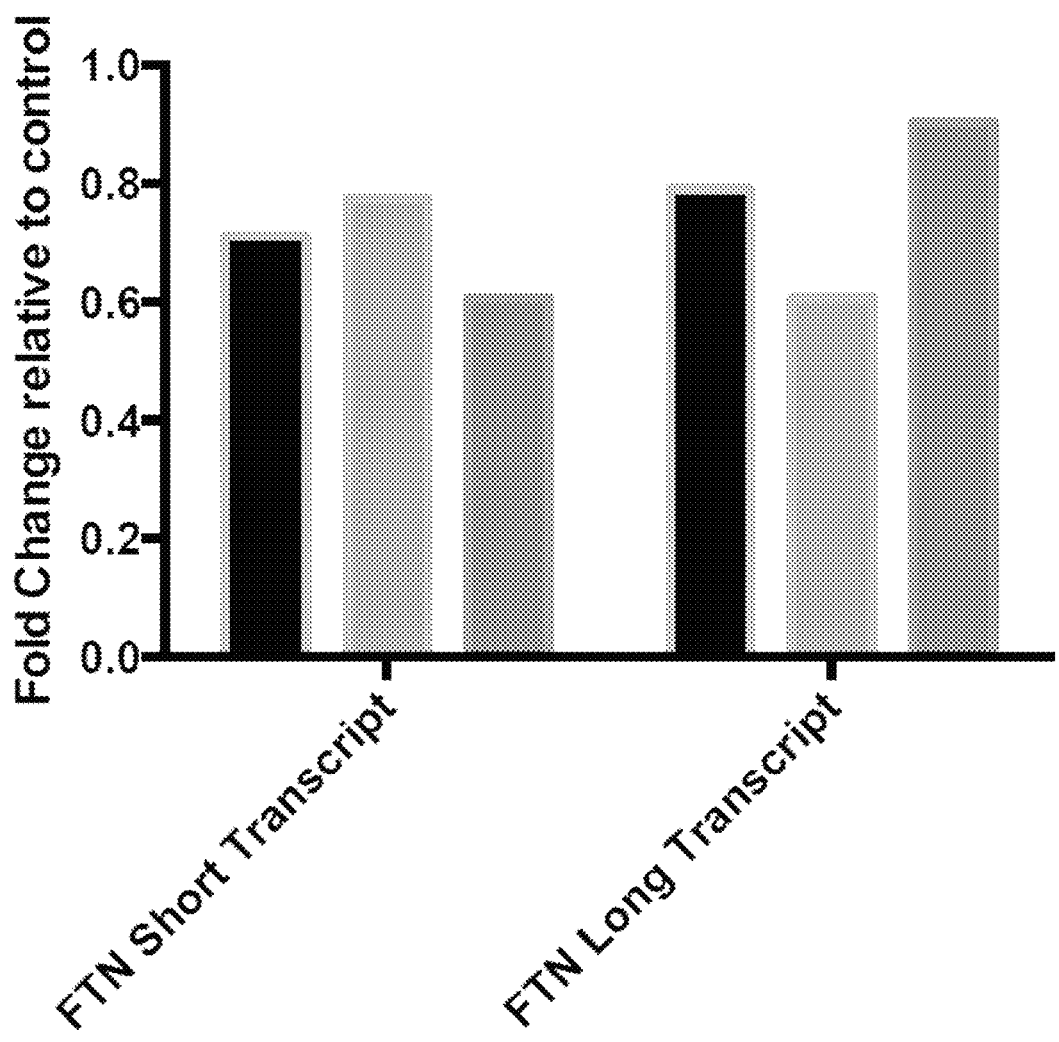
FIG. 4 provides a graph representing the expression of the bacterial lipoprotein FTN_1103 in *E. coli* cells transformed with plasmids comprising the *F. novicida* CRISPR/Cas locus along with the FTN_1103 gene relative to control (*E. coli* comprising no FnCas9 and no *F. novicida* CRISPR/Cas locus); Black: 1:10 dilution; light grey: 1:100 dilution; dark grey: 1:1000 dilution.

After determining that the components of the *Francisella novicida* RNA-targeting CRISPR system were successfully expressed in *E. coli*, it was assessed that they could cleave the endogenous target, FTN_1103. Exogenous FTN_1103 was introduced into RNA-targeting CRISPR-expressing *E. coli* strains. Two different variants of FTN_1103, denoted FTN short transcript and FTN long transcript, based on the length of the locus, were introduced into RNA-targeting CRISPR-expressing *E. coli* strains. The amount of cleavage was determined via qPCR. As shown in FIG. 4, the FnCas9 cells have reduced expression of FTN_1103 relative to control (*E. coli* comprising no FnCas 9 and no *F. novicida* RNA-targeting CRISPR/Cas locus) indicating knockdown in this system. Next, rather than introducing these genes on plasmids, the genes are integrated into the *E. coli* genome in order to obtain more substantial knockdown consistent with the natural *F. novicida* system.

Example 5: Further Characterization of CRISPR/Cas RNA Targeting System

Characterizing Endogenous scaRNA traerRNA Transcripts

Figure 5:
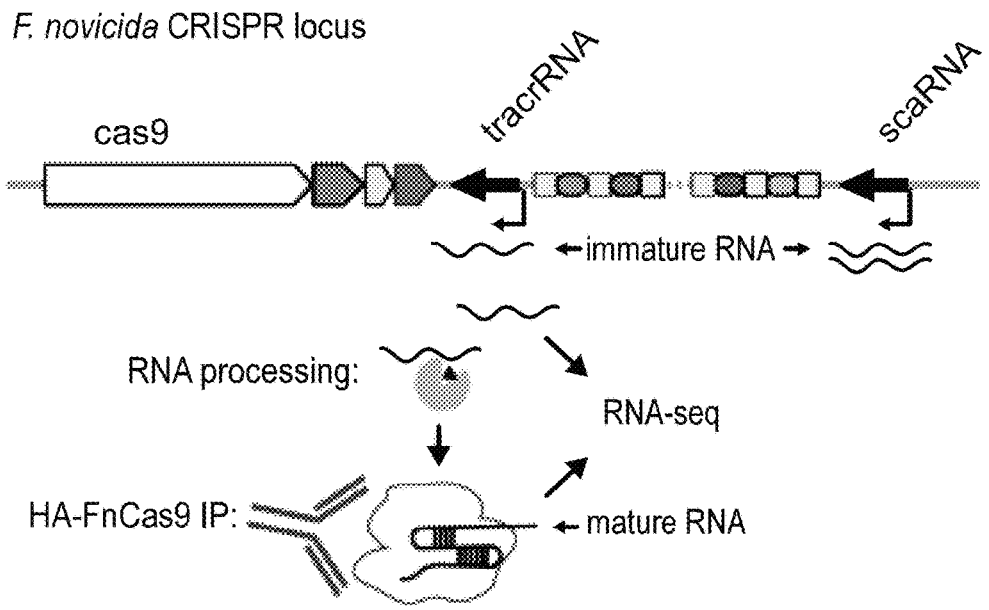
FIG. 5 provides a schematic representation of a method for characterizing potential enzymatic maturation of scaRNA and tracrRNA.

Since CRISPR RNAs often undergo enzymatic maturation, further immunoprecipitation and sequencing (IP-seq) of an epitope-tagged FnCas9 is performed to reveal the processing state of Fn RNAs in their bound and unbound states (FIG. 5).

Additional Biochemical Characterization

The identified mature Fn RNA sequences are in vitro transcribed and tested with affinity purified FnCas9 protein in gel shift assays, in order to characterize their biochemical interaction with the endogenous lipoprotein (blp) mRNA target. Different regions of the scaRNA, tracrRNA, and mRNA are mutated to facilitate localization of the guide sequence actually involved in hybridizing with the target lipoprotein mRNA. To gain additional structural insight, FnCas9 in complex with its guide and target RNAs is crystallized and characterized.

Recognition Rules of FinCas9 to a Target mRNA

Figure 6:
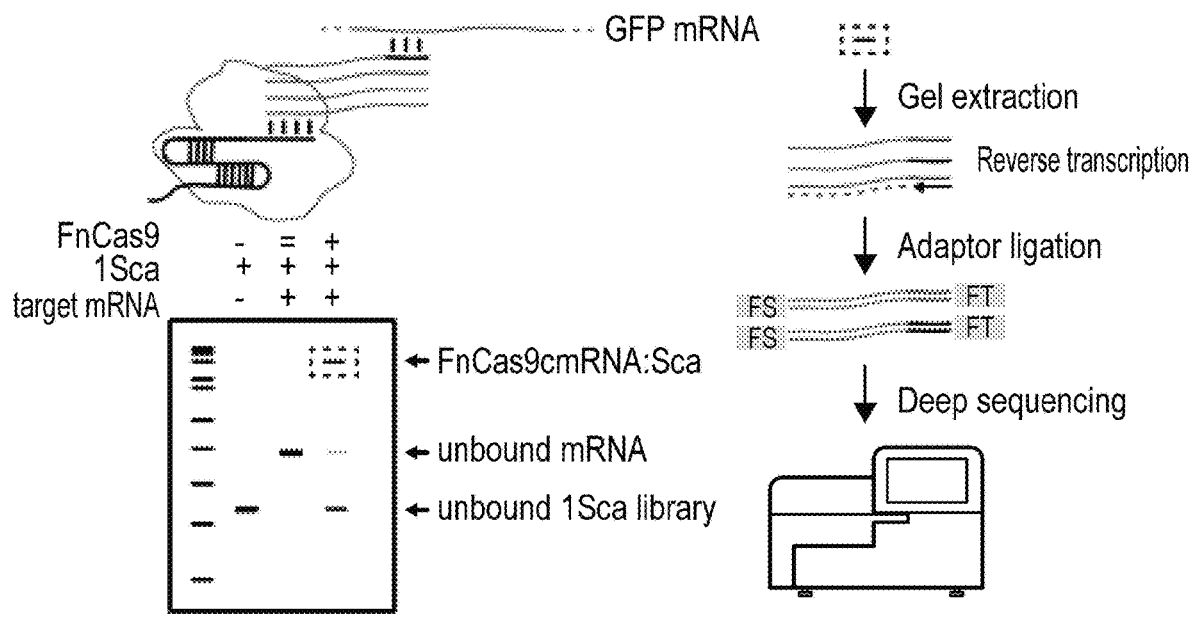
FIG. 6 provides a schematic representation of a method for screening for retargeted fSca guide sequences.

FnCas9 recognition of a target mRNA is putatively due to the hybridization between the scaRNA: tracrRNA hybrid (i.e., fSca) and the target mRNA, but the recognition pattern is not as straightforward as perfect complementarity. To better understand the binding rules of fSca to desired mRNAs, the thermodynamic interaction of candidate guide sequences with target RNAs is computationally modeled to design optimal, retargeted fSca transcripts. In order to understand and refine the rules underlying the RNA-targeting FnCas9 complex, a library of scaRNA/tracrRNA sequences retargeted to eGFP is synthesized. The battery of guide RNAs is then screened via EMSA, with the fraction bound to FnCas9 and target RNA undergoing reverse transcription, Illumina adapter ligation, and deep sequencing (FIG. 6). This high-throughput approach can reveal the base-pairing rules between the fSca and target mRNA.

Developing a Heterologous RNA Targeting Technology in Human Cells

To test if FnCas9 and fSca can target specific RNAs in mammalian cells, different combinations of the Fn RNA-targeting system are heterologously expressed in HEK293T cells stably expressing eGFP. By immunoprecipitating HA-tagged FnCas9 with fSca combinations targeting eGFP transcripts and performing RNA-seq on the RNAs that are pulled down, binding of the desired target mRNA as well as potential off-target interactions are simultaneously tested. qRT-PCR is performed to reveal if target eGFP transcripts are degraded, while effects on protein levels are determined via FACS analysis.

In order to identify any additional protein components of the RNA-targeting FnCas9 regulatory complex, epitope-tagged FnCas9 from *F. novicida* is immunoprecipitated followed by tandem mass spectrometry (co-IP). The candidate RNases are co-transfected with FnCas9 in HEK 293T cells and tested for ability to knock down eGFP. If efficient eGFP degradation is achieved, off-target cleavage and promiscuous RNase activity is monitored via whole transcriptome RNA-seq. In case eGFP knockdown fails with the *F. novicida*-derived RNase, instead a series of FnCas9 fusions to ribonucleases derived from the metagenomic spectrum is generated. This approach can also be used in the event of high off-target RNA degradation by FnCas9.

Figure 7:
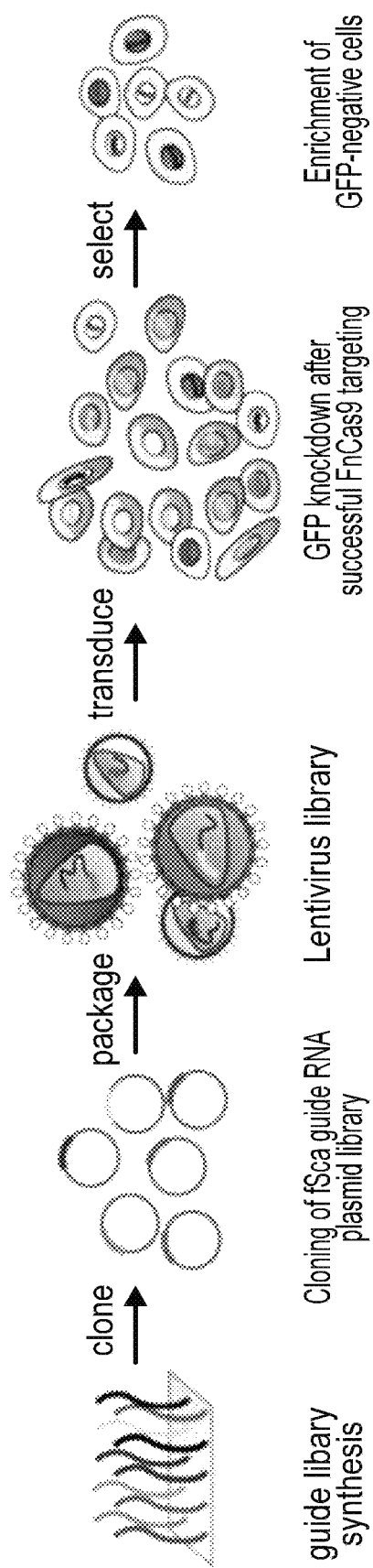
FIG. 7 provides a schematic representation of a method for studying the specificity and efficiency of fSca guide sequences.

To systematically characterize how the fSca guide sequence dictates FnCas9 specificity and efficiency, a lentiviral-based pooled screen in HEK 293T-GFP cells is developed with two libraries of fSca guide sequences: one on-target library tiling the eGFP locus and one off-target library containing only guides with mismatches to the target eGFP (FIG. 7). FACS-based isolation of eGFP-negative cells followed by deep sequencing is performed to compare the relative enrichment of guide sequences before and after sorting. More efficient guides or those tolerating mismatches are expected to be present in higher abundance in the sorted fraction. This allows investigating the contributions of base position and identity for both mismatched and complementary nucleotides on FnCas9 targeting.

Computational Analysis of Cas9 Orthologs for Multiple Putative traerRNA scaRNA

Figure 8:
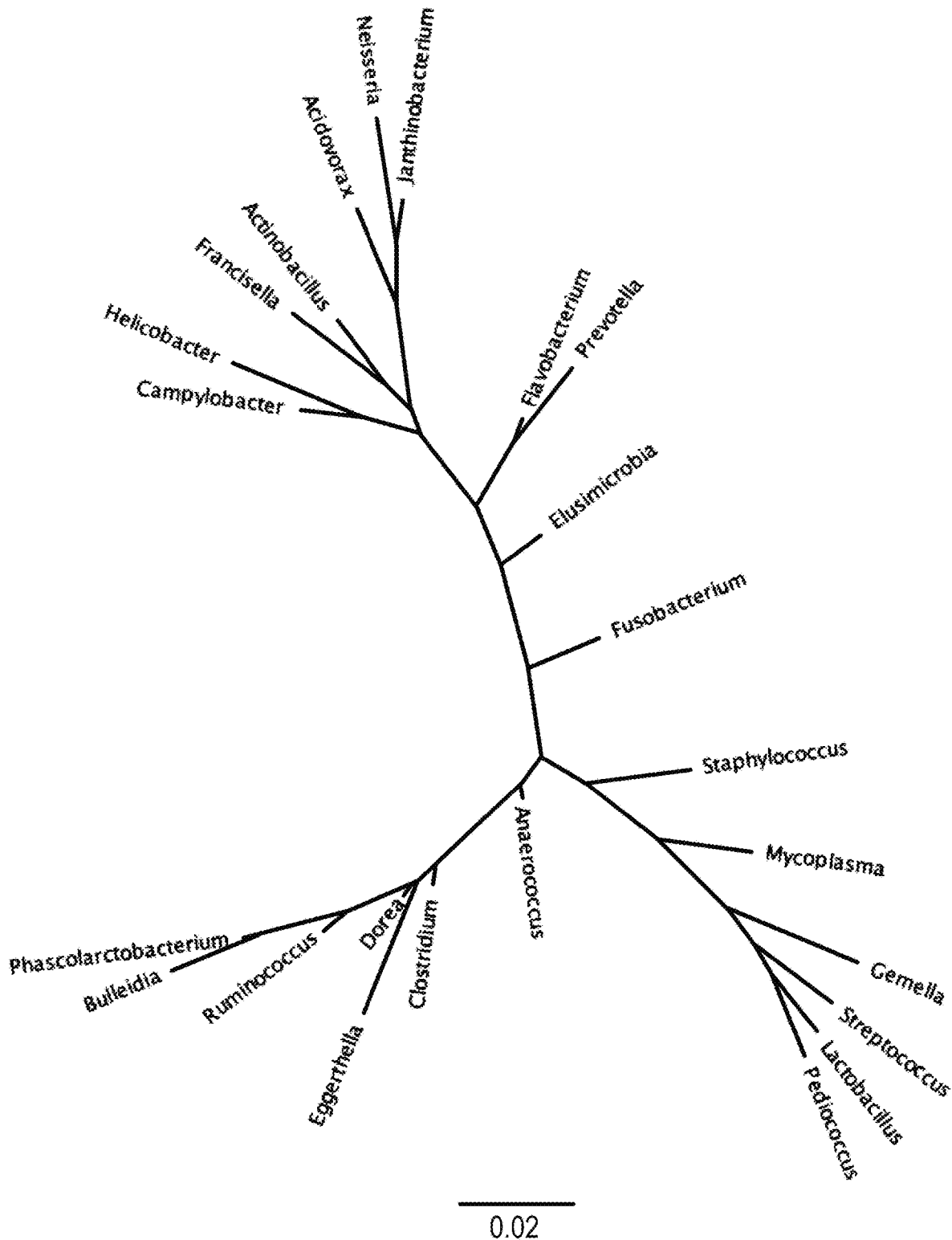
FIG. 8 provides a phylogenetic tree with plots of species with more than 1 putative tracrRNA/scaRNA.

Applicants perform an analysis on the Cas9 orthologs from Makarova et al. (Biol. Direct 1, 7 (2006)) to identify multiple putative tracrRNA, implying a system involving a scaRNA, analogous to FnCas9. The Cas9 orthologs of interest (attached) are checked for being within 15 kb of a potential CRISPR locus, as determined by the CRISPR recognition tool (Bland, C. et al. BMC Bioinformatics 8, 209 (2007)). All potential CRISPR loci meeting this criterion are analyzed for sequences within 1 kb of the CRISPR locus with 75% complementarity to the direct repeats. Detected sequences above this threshold of complementarity are classified as putative tracrRNA/scaRNA. Species with more than 1 putative tracrRNA/scaRNA are plotted in a phylogenetic tree (FIG. 8). A list of mined cas9 includes but is not limited to: *Campylobacter jejuni* subsp. doylei 269.97, *Campylobacter jejuni* subsp. *jejuni* 81116, *Campylobacter jejuni* subsp. *jejuni* NCTC 11168=ATCC 700819, Kingella kingae ATCC 23330, *Gluconacetobacter diazotrophicus* PAI 5, *Helicobacter canadensis* MIT 98-5491, *Clostridium cellulolyticum* H10, *Helicobacter cinaedi* CCUG 18818, *Helicobacter mustelae* 12198, gamma proteobacterium HdN1, Alicycliphilus *denitrificans* BC, Alicycliphilus *denitrificans* K601, uncultured Termite group 1 bacterium phylotype Rs-D17, uncultured Termite group 1 bacterium phylotype Rs-D17, Candidatus Puniceispirillum *marinum* IMCC1322, Parvibaculum lavamentivorans DS-1, *Nitrosomonas* sp. AL212, Acidovorax *avenae* subsp. *avenae* ATCC 19860, *Gluconacetobacter diazotrophicus* PAI 5, Aminomonas *paucivorans* DSM 12260, *Haemophilus parainfluenzae* T3T1, *Staphylococcus aureus* subsp. *aureus, Actinobacillus pleuropneumoniae* serovar 10 str. D13039, *Staphylococcus lugdunensis* M23590, *Pasteurella multocida* subsp. *multocida* str. Pm70, *Actinobacillus minor* NM305, Wolinella *succinogenes* DSM 1740, *Actinobacillus succinogenes* 130Z, Ralstonia *syzygii* R24, Rhodopseudomonas *palustris* BisB5, Bradyrhizobium sp. BTAil, *Clostridium perfringens* D str. JGS1721, Simonsiella *muelleri* ATCC 29453, Rhodopseudomonas *palustris* BisB18, Verminephrobacter *eiseniae* EF01-2, *Bacillus cereus* Rock1-15, *Neisseria bacilliformis* ATCC BAA-1200, Dinoroseobacter shibae DFL 12, *Methylocystis* sp. ATCC 49242, *Neisseria flavescens* SK114, *Neisseria meningitidis* 053442, *Neisseria meningitidis* Z2491, *Neisseria meningitidis* alpha14, *Neisseria cinerea* ATCC 14685, *Methylosinus trichosporium* OB3b, *Neisseria* lactamica Corynebacterium diphtheriae NCTC 13129, Phascolarctobacterium succinatutens YIT 12067, Corynebacterium matruchotii ATCC 14266, Sphingomonas sp. S17, Mobiluncus mulieris 28-1, Ilyobacter polytropus DSM 2926, Eubacterium dolichum DSM 3991, Corynebacterium accolens ATCC 49726, Akkermansia muciniphila ATCC BAA-835, Actinomyces coleocanis DSM 15436, Eubacterium ventriosum ATCC 27560, Staphylococcus simulans ACS-120-V-Sch1, Eubacterium rectale ATCC 33656, Clostridium spiroforme DSM 1552, Lactobacillus coryniformis subsp. torquens KCTC 3535, Streptococcus thermophilus LMD-9, Streptococcus thermophilus LMG 18311, Streptococcus suis 89/1591, Streptococcus suis ST3, Mobiluncus curtisii subsp. holmesii ATCC 35242, Lactobacillus farciminis KCTC 3681, Streptococcus thermophilus CNRZ1066, Streptococcus vestibularis ATCC 49124, Streptococcus infantarius subsp. infantarius ATCC BAA-102, Streptococcus gallolyticus UCN34, Streptococcus pasteurianus ATCC 43144, Streptococcus macedonicus ACA-DC 198, Acidovorax ebreus TPSY, Nitratifractor salsuginis DSM 16511, Streptococcus mitis ATCC 6249, Streptococcus gordonii str. Challis substr. CHI, Acidothermus cellulolyticus 11B, Bifidobacterium dentium Bd1, Roseburia intestinalis L1-82, Enterococcus faecalis TX0012, Roseburia inulinivorans DSM 16841, Ruminococcus albus 8, Nitrobacter hamburgensis X14, Azospirillum sp. B510, Rhodospirillum rubrum ATCC 11170, Scardovia inopinata F0304, Sphaerochaeta globus str. Buddy, Gardnerella vaginalis 5-1, Bifidobacterium longum DJO10A, Elusimicrobium minutum Pei191, Prevotella ruminicola 23, Prevotella buccalis ATCC 35310, Prevotella timonensis CRIS 5C-B1, Bacteroides cellulosilyticus DSM 14838, Mycoplasma canis PG 14, Prevotella tannerae ATCC 51259, Mycoplasma mobile 163K, Lactobacillus buchneri ATCC 11577, Mycoplasma ovipneumoniae SC01, Mycoplasma gallisepticum str. F, Mycoplasma gallisepticum str. R (low), Mycoplasma synoviae 53, Streptococcus pseudoporcinus SPIN 20026, Solobacterium moorei F0204, Enterococcus italicus DSM 15952, Lactobacillus sanfranciscensis TMW 1.1304, Listeria innocua Clip11262, Listeria monocytogenes str. 1/2a F6854, Staphylococcus pseudintermedius ED99, Coprococcus catus GD/7, Streptococcus macacae NCTC 11558, Dorea longicatena DSM 13814, Enterococcus faecium 1,231,408, Ruminococcus lactaris ATCC 29176, Peptoniphilus sp. oral taxon 386 str. F0131, Streptococcus mutans UA159, Streptococcus mutans NN2025, Streptococcus anginosus F0211, Finegoldia magna ATCC 29328, Streptococcus equi subsp. zooepidemicus MGCS10565, Megasphaera sp. UPII 135-E, Flavobacterium psychrophilum JIP02/86, Prevotella melaninogenica D18, Acidaminococcus sp. D21, Acidaminococcus intestini RyC-MR95, Lactobacillus casei BL23, Anaerococcus tetradius ATCC 35098, Lactobacillus casei str. Zhang, Lactobacillus paracasei subsp. paracasei 8700:2, Lactobacillus rhamnosus GG, Pediococcus acidilactici DSM 20284, Peptoniphilus duerdenii ATCC BAA-1640, Filifactor alocis ATCC 35896, Streptococcus pyogenes MI GAS, Streptococcus pyogenes MGAS315, Streptococcus pyogenes SSI-1, Streptococcus pyogenes MGAS6180, Streptococcus pyogenes MGAS5005, Streptococcus pyogenes MGAS9429, Streptococcus pyogenes MGAS10270, Streptococcus pyogenes MGAS2096, Streptococcus pyogenes NZ131, Lactobacillus iners LactinV 11V1-d, Streptococcus agalactiae 2603V/R, Streptococcus agalactiae A909, Streptococcus gallolyticus subsp. gallolyticus ATCC BAA-2069, Streptococcus pyogenes MGAS10750, Streptococcus dysgalactiae subsp. equisimilis GGS_124, Streptococcus gallolyticus UCN34, Gordonibacter pamelaeae 7-10-1-b, Lactobacillus buchneri NRRL B-30929, Legionella pneumophila str. Paris, Streptococcus bovis ATCC 700338, Fusobacterium nucleatum subsp. vincentii ATCC 49256, Lactobacillus ruminis ATCC 25644, Lactobacillus johnsonii DPC 6026, Streptococcus agalactiae NEM316, Lactobacillus brevis subsp. gravesensis ATCC 27305, Streptococcus equinus ATCC 9812, Eggerthella sp. YY7918, Lactobacillus fermentum ATCC 14931, Coriobacterium glomerans PW2, Gemella morbillorum M424, Streptococcus thermophilus LMD-9, Zunongwangia profunda SM-A87, Oenococcus kitaharae DSM 17330, Kordia algicida OT-1, Lactobacillus jensenii 269-3, Lactobacillus gasseri JV-V03, Prevotella oralis ATCC 33269, Gemella haemolysans ATCC 10379, Treponema denticola ATCC 35405, gamma proteobacterium HTCC5015, Veillonella parvula ATCC 17745, Veillonella atypica ACS-134-V-Col7a, Olsenella uli DSM 7084, Wolinella succinogenes DSM 1740, Bifidobacterium bifidum S17, Sutterella wadsworthensis 3_1_45B, Parabacteroides sp. D13, Prevotella micans F0438, Capnocytophaga sputigena Capno, Capnocytophaga ochracea DSM 7271, Sphingobacterium spiritivorum ATCC 33861, Burkholderiales bacterium 1_1_47, Parasutterella excrementihominis YIT 11859, Capnocytophaga canimorsus Cc5, Bacteroidetes oral taxon 274 str. F0058, Bacteroides fragilis NCTC 9343, Capnocytophaga gingivalis ATCC 33624, Weeksella virosa DSM 16922, Parabacteroides johnsonii DSM 18315, Prevotella buccae ATCC 33574, Fluviicola taffensis DSM 16823, Flavobacterium columnare ATCC 49512, Flavobacterium branchiophilum FL-15, Mucilaginibacter paludis DSM 18603, Prevotella bivia JCVIHMP010, Prevotella veroralis F0319, Bacteroides dorei DSM 17855, Bacteroides coprophilus DSM 18228, Fibrobacter succinogenes subsp. succinogenes S85, Bacteroides sp. 20_3, Flavobacterium columnare ATCC 49512, and Francisella novicida U112.

In the event that FnCas9 expresses or functions poorly in eukaryotic cells, metagenomic discovery is performed to mine alternative Cas9s that could interact with RNA. Several CRISPR systems have been implicated in gene regulatory functions at the RNA level, and computational analysis reveals many type II CRISPR loci that possess multiple putative transcripts possessing anti-direct repeat sequences. The subset of these (50% or less) that do not serve as canonical tracrRNAs for crRNA targeting may be prokaryotic small RNAs involved in post-transcriptional regulation. A combination of RNA-seq and Cas9 cross-linking immunoprecipitation sequencing (CLIP-Seq) in these prokaryotes facilitates further functional characterization.

Example 6: scaRNA

Figure 9A:
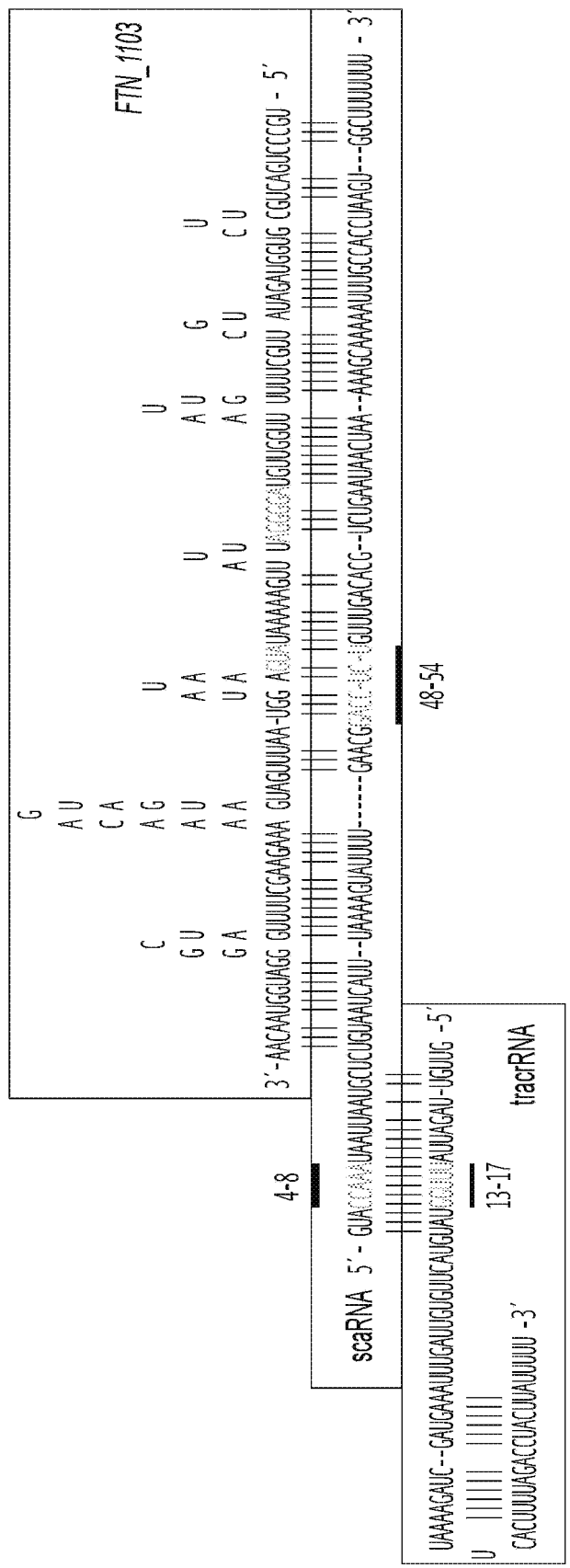

FIG. 9A provides the sequence of scaRNA from Sampson et al. (2013, Nature 497:254-258).

Figure 9C:
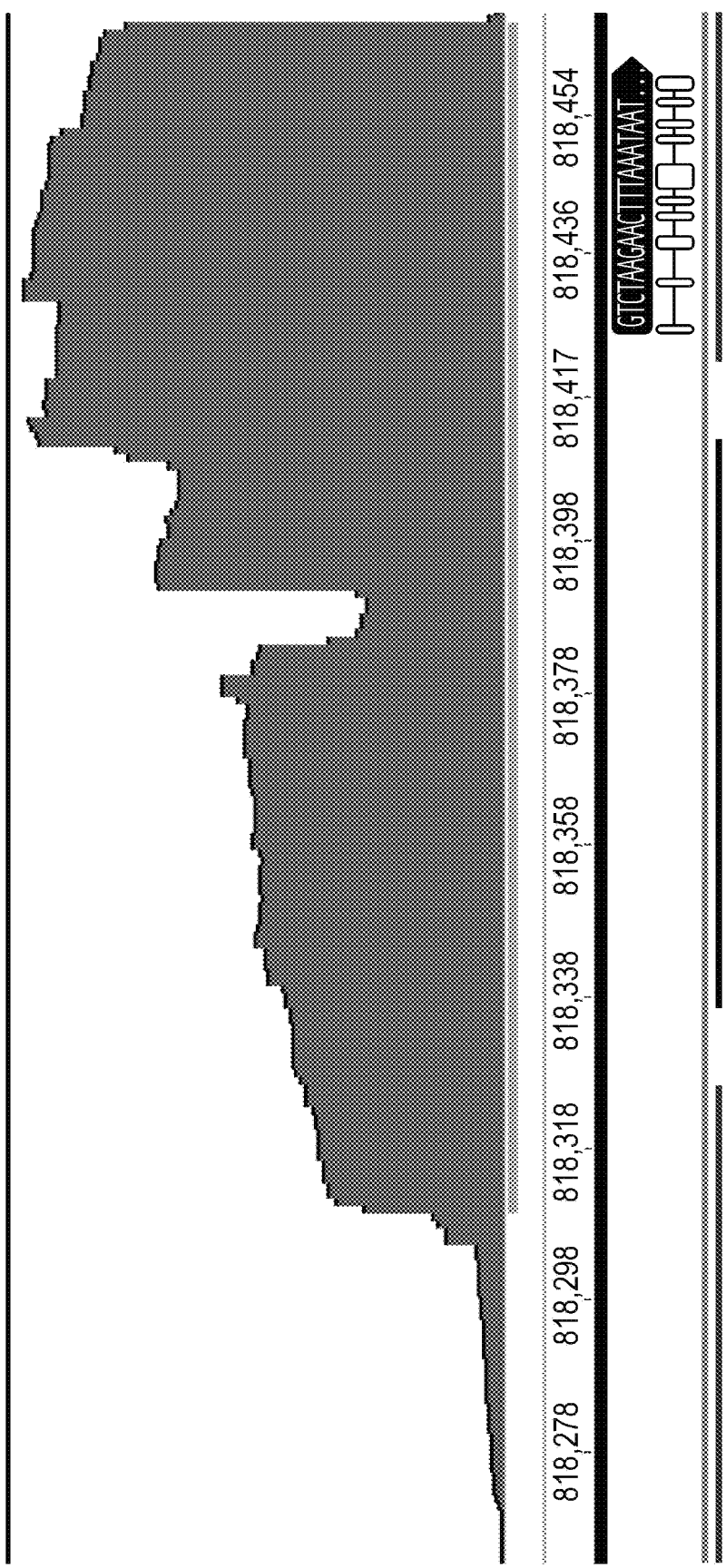

FIG. 9B provides the sequence of Applicants' scaRNA from RNA sequencing and FIG. 9C provides RNA Seq reads on ScaRNA.

The invention is further described by the following numbered paragraphs:

1. A non-naturally occurring or engineered vector system comprising one or more vectors comprising:
   a) a first regulatory element operably linked to a polynucleotide sequence encoding an RNA-targeting guide RNA (Rt-gRNA), wherein said RNA-targeting guide RNA is capable of hybridizing with a target RNA, wherein said RNA-targeting guide RNA comprises:
      (i) a small CRISPR/Cas system associated RNA (scaRNA) sequence, and (ii) a trans-activating CRISPR/Cas system RNA (tracrRNA) sequence, wherein said scaRNA and said tracrRNA are capable of at least partially hybridizing, and b) a second regulatory element operably linked to a polynucleotide sequence encoding an RNA-targeting Cas protein, wherein components (a) and (b) are located on the same or different vectors of the system.

2. The vector system according to numbered paragraph 1, wherein said RNA-targeting guide RNA and said RNA-targeting Cas protein do not naturally occur together.

3. The vector system according to numbered paragraph 1 or 2, wherein said RNA-targeting Cas protein is a type II Cas protein.

4. The vector system according to numbered paragraph 3, wherein said RNA-targeting Cas protein is a Cas9 protein.

5. The vector system according to claim 3, wherein said RNA-targeting Cas protein is from *Francisella novicida*.

6. The vector system according to numbered paragraph 3, wherein said RNA-targeting Cas protein is the Cas9 protein from *Francisella novicida* (FnCas9).

7. The vector system according to numbered paragraph 3, wherein said RNA-targeting Cas protein is an FnCas9 homolog showing at least 80% sequence homology with wild type FnCas9.

8. The vector system according to numbered paragraph 3, wherein said RNA-targeting Cas protein is an FnCas9 ortholog.

9. The vector system according to numbered paragraph 1, wherein said scaRNA sequence is fused to said tracrRNA sequence.

10. The vector system according to numbered paragraph 1, wherein said RNA-targeting Cas protein is codon optimized for expression in a eukaryotic cell.

11. The vector system according to numbered paragraph 1, wherein said one or more vectors are viral vectors.

12. The vector system according to numbered paragraph 1, wherein said one or more viral vectors are selected from the group consisting of retroviral, lentiviral, adenoviral, adeno-associated and herpes simplex viral vectors.

13. The vector system according to numbered paragraph 1, wherein said RNA-targeting guide RNA is capable of directing said RNA-targeting Cas protein to said target RNA.

14. A vector comprising a regulatory element operably linked to a polynucleotide sequence encoding an RNA-targeting Cas protein, preferably FnCas9 or an FnCas9 homolog or ortholog.

15. A vector comprising a regulatory element operably linked to a polynucleotide sequence encoding an RNA-targeting guide RNA, wherein said RNA-targeting guide RNA is capable of hybridizing with a target RNA, wherein said RNA-targeting guide RNA comprises:
   (i) a small CRISPR/Cas system associated RNA (scaRNA) sequence, and
   (ii) a trans-activating CRISPR/Cas system RNA (tracrRNA) sequence, wherein said scaRNA and said tracrRNA are capable of at least partially hybridizing.

16. A composition comprising a vector system according to numbered paragraph 1 or a vector according to numbered paragraph 14 or 15.

17. A non-naturally occurring or engineered RNA-targeting system comprising an RNA-targeting Cas protein and at least one RNA-targeting guide RNA, wherein said RNA-targeting guide RNA is capable of binding to a target RNA in an eukaryotic cell, wherein said RNA-targeting guide RNA comprises:
   (i) a small CRISPR/Cas system associated RNA (scaRNA) sequence, and
   (ii) a trans-activating CRISPR/Cas system RNA (tracrRNA) sequence, wherein said scaRNA and said tracrRNA are capable of at least partially hybridizing.

18. The system according to numbered paragraph 17, wherein said RNA-targeting Cas protein is FnCas9 or an FnCas9 homolog or ortholog.

19. A method for modulating synthesis of a protein comprising introducing into a cell containing an RNA molecule encoding said protein, a vector system comprising one or more vectors comprising:
   a) a first regulatory element operably linked to a polynucleotide sequence encoding an RNA-targeting guide RNA, wherein said RNA-targeting guide RNA is capable of hybridizing with said target RNA, wherein said RNA-targeting guide RNA comprises:
      (i) a small CRISPR/Cas system associated RNA (scaRNA) sequence, and
      (ii) a trans-activating CRISPR/Cas system RNA (tracrRNA) sequence, wherein said scaRNA and said tracrRNA are capable of at least partially hybridizing, and
   b) a second regulatory element operably linked to a polynucleotide sequence encoding an RNA-targeting Cas protein,
   wherein components (a) and (b) are located on the same or different vectors of the system,
   whereby synthesis of said protein is modulated.

20. The method according to numbered paragraph 19, wherein the synthesis of said protein is suppressed.

21. The method according to numbered paragraph 20, wherein the synthesis of said protein is suppressed by knock-down of said RNA molecule encoding said protein.

22. The method according to numbered paragraph 19, wherein the synthesis of said protein is modulated by editing of said RNA molecule encoding said protein.

23. The method according to numbered paragraph 15, wherein the synthesis of said protein is modulated by splicing of said RNA molecule encoding said protein.

24. A method for targeting RNA comprising introducing into a cell containing a target RNA a non-naturally occurring or engineered vector system comprising one or more vectors comprising:
   a) a first regulatory element operably linked to a polynucleotide sequence encoding an RNA-targeting guide RNA, wherein said RNA-targeting guide RNA is capable of hybridizing with said target RNA, wherein said RNA-targeting guide RNA comprises:
      (i) a small CRISPR/Cas system associated RNA (scaRNA) sequence, and
      (ii) a trans-activating CRISPR/Cas system RNA (tracrRNA) sequence, wherein said scaRNA and said tracrRNA are capable of at least partially hybridizing, and
   b) a second regulatory element operably linked to a polynucleotide sequence encoding an RNA-targeting Cas protein,
   wherein components (a) and (b) are located on the same or different vectors of the system,
   whereby said RNA-targeting guide RNA directs said RNA-targeting Cas protein to said target RNA.

25. The method according to numbered paragraph 19 or 24, wherein said RNA-targeting Cas protein is a type II Cas protein.

26. The method according to numbered paragraph 25 wherein said RNA-targeting Cas protein is a Cas9 protein.

27. The method according to numbered paragraph 25, wherein said RNA-targeting Cas protein is from *Francisella novicida*.

28. The method according to numbered paragraph 25, wherein said RNA-targeting Cas protein is an FnCas9 homolog showing at least 80% sequence homology with wild type FnCas9.

29. The method according to numbered paragraph 25, wherein said RNA-targeting Cas protein is an FnCas9 ortholog.

30. The method according to numbered paragraph 19 or 24, wherein said RNA-targeting Cas protein is codon optimized for expression in a eukaryotic cell.

31. The method according to numbered paragraph 19 or 24, wherein said one or more vectors are viral vectors.

32. The method according to numbered paragraph 19 or 24, wherein said one or more viral vectors are selected from the group consisting of retroviral, lentiviral, adenoviral, adeno-associated and herpes simplex viral vectors.

33. The method according to numbered paragraph 19 or 24, wherein the cell is a eukaryotic cell.

34. The method according to numbered paragraph 30, wherein the eukaryotic cell is a mammalian or human cell.

35. The vector system, vector, composition or method according to any one of the preceding numbered paragraphs, wherein one or more amino acid residues of the RNA-targeting Cas protein are modified.

36. The vector system, vector, composition or method according to numbered paragraph 35, wherein the modification comprises mutation of one or more, or two or more, or three or more amino acid residues of the RNA-targeting Cas protein.

37. The vector system, vector, composition or method according to numbered paragraph 35 or 36, wherein the one or more, or two or more, or three or more mutations are in one or more catalytically active domains of the RNA-targeting Cas protein.

38. The vector system, vector, composition or method according to numbered paragraph 37, wherein the RNA-targeting Cas protein has reduced or abolished nuclease activity compared with an RNA-targeting Cas protein lacking said mutation(s).

39. The vector system, vector, composition or method according to numbered paragraph 38, wherein the one or more, or two or more mutations are in a catalytically active domain of the RNA-targeting Cas protein comprising a RuvCI, RuvCII or RuvCIII domain.

40. The vector system, vector, composition or method according to any one of numbered paragraphs 35 to 39, wherein the RNA-targeting Cas protein comprises one or more heterologous functional domains.

41. The vector system, vector, composition or method according to numbered paragraph 40, wherein the one or more heterologous functional domains comprises one or more nuclear localization signal (NLS) domains.

42. The vector system, vector, composition or method according to numbered paragraph 41, wherein the one or more heterologous functional domains comprises at least two or more NLS domains.

43. The vector system, vector, composition or method according to numbered paragraph 40, wherein the one or more heterologous functional domains comprises one or more transcriptional activation domains.

44. The vector system, vector, composition or method according to numbered paragraph 43, wherein the transcriptional activation domain comprises VP64.

45. The vector system, vector, composition or method according to numbered paragraph 40, wherein the one or more heterologous functional domains comprises one or more transcriptional repression domains.

46. The vector system, vector, composition or method according to numbered paragraph 45, wherein the transcriptional repression domain comprises a KRAB domain or a SID domain.

47. The vector system, vector, composition or method according to numbered paragraph 40, wherein the one or more heterologous functional domains comprises one or more nuclease domains.

48. The vector system, vector, composition or method according to numbered paragraph 47, wherein a nuclease domain comprises Fok1.

49. The vector system, vector, composition or method according to numbered paragraph 40, wherein the one or more heterologous functional domains have one or more of the following activities: methylase activity, demethylase activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity and nucleic acid binding activity.

50. The vector system, vector, composition or method according to any one of numbered paragraphs 40 to 49, wherein at least one or more heterologous functional domains is at or near the amino-terminus of the RNA-targeting Cas protein and/or wherein at least one or more heterologous functional domains is at or near the carboxy-terminus of the RNA-targeting Cas protein.

51. The vector system, vector, composition or method according to any one of numbered paragraphs 40 to 50, wherein said one or more heterologous functional domains are fused to the RNA-targeting Cas protein.

52. The vector system, vector, composition or method according to any one of numbered paragraphs 40 to 50, wherein said one or more heterologous functional domains are tethered to the RNA-targeting Cas protein.

53. The vector system, vector, composition or method according to any one of numbered paragraphs 40 to 50, wherein said one or more heterologous functional domains are linked to the RNA-targeting Cas protein by a linker moiety.

54. The vector system, vector, composition or method according to any one of the preceding numbered paragraphs, wherein the RNA-targeting Cas protein comprises an RNA-targeting Cas protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium* or *Corynebacterium*.

55. The vector system, vector, composition or method according to any one of the preceding numbered paragraphs, wherein the RNA-targeting Cas protein comprises a chimeric RNA-targeting Cas protein comprising a first fragment from a first RNA-targeting Cas protein ortholog and a second fragment from a second RNA-targeting Cas protein ortholog, and wherein the first and second RNA-targeting Cas protein orthologs are different, wherein at least one of the first and second orthologs is *Francisella novicida*.

56. The vector system, vector, composition or method according to numbered paragraph 55, wherein at least one of the first and second RNA-targeting Cas protein orthologs comprises an RNA-targeting Cas protein from an organism comprising *Streptococcus, Campylobacter, Nitratifractor, Staphylococcus, Parvibaculum, Roseburia, Neisseria, Gluconacetobacter*, Azospirillum, Sphaerochaeta, *Lactobacillus, Eubacterium* or *Corynebacterium*.

57. The vector system, vector, composition or method according to any one of the preceding numbered paragraphs, wherein the tracrRNA comprises one or more protein-binding RNA aptamers.

58. The vector system, vector, composition or method according to any one of the preceding numbered paragraphs, wherein the scaRNA comprises one or more protein-binding RNA aptamers.

59. The vector system, vector, composition or method according to numbered paragraph 57 or numbered paragraph 58, wherein the one or more aptamers is capable of binding a bacteriophage coat protein.

60. The vector system, vector, composition or method according to numbered paragraph 59, wherein the bacteriophage coat protein is selected from the group comprising QB, F2, GA, fr, JP501, MS2, M12, R17, BZ13, JP34, JP500, KUI, M11, MX1, TW18, VK, SP, FI, ID2, NL95, TW19, AP205, ¢Cb5, ¢Cb8r, ¢Cb12r, ¢Cb23r, 7s and PRR1.

61. The vector system, vector, composition or method according to numbered paragraph 60, wherein the bacteriophage coat protein is MS2.

62. The vector system, vector, composition or method according to any one of the preceding numbered paragraphs, wherein the tracrRNA is 30 or more, 40 or more or 50 or more nucleotides in length.

63. The vector system, vector, composition or method according to any one of the preceding numbered paragraphs, wherein the RNA-targeting Cas protein is further modified to comprise PAM sequence specificity which is different to the PAM sequence specificity of the RNA-targeting Cas protein without said further modification.

64. The vector system, vector, composition or method according to numbered paragraph 63, wherein said further modification comprises the introduction of one or more amino acid mutations into the RNA-targeting Cas protein, or by truncation of the RNA-targeting Cas protein, or by deletion and/or insertion of specific amino acids or amino acid sequences into the RNA-targeting Cas protein.

65. The vector system, vector, composition or method according to any one of the preceding numbered paragraphs, comprising delivering multiple Rt-gRNAs, wherein each Rt-gRNAs is specific for a different target RNA whereby there is multiplexing.

66. A host cell or cell line comprising the vector system, vector, or composition according to any one of numbered paragraphs 1-18 or 35-65, or progeny thereof.

67. The host cell or cell line or progeny thereof according to numbered paragraph 66, which is ex vivo or in vitro.

68. The host cell or cell line or progeny thereof according to any one of numbered paragraphs 66-67, which is a stem cell or a stem cell line, or a plant cell or a plant cell line.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A non-naturally occurring or engineered vector system comprising one or more vectors comprising:
  a) a first regulatory element operably linked to a first polynucleotide sequence encoding an RNA-targeting guide RNA (Rt-gRNA), wherein said Rt-gRNA is designed to hybridize with a target RNA, wherein said Rt-gRNA comprises:
    (i) a small CRISPR/Cas system associated RNA (scaRNA) sequence, and
    (ii) a trans-activating CRISPR/Cas system RNA (tracrRNA) sequence, wherein said scaRNA and said tracrRNA are designed to at least partially hybridize to each other, and
  b) a second regulatory element operably linked to a second polynucleotide sequence encoding
    (i) a *Francisella novicida* Cas protein (FnCas) or ortholog, homolog, or fragment thereof comprising a Rec1 domain, Rec2 domain, HNH domain, and PAM Interacting (PI) domain, and
    (ii) one or more heterologous functional domains positioned at one or more sites in FnCas that are analogous to amino acid positions 534-676 corresponding to a wild type *Streptococcus pyogenes* Cas9 (SpCas9) Rec1 domain
    wherein the Rt-gRNA is capable of forming an RNA-targeting complex with the FnCas and of directing sequence-specific binding of the RNA-targeting complex to the target RNA,
    wherein each of the one or more heterologous functional domains comprise one or more of the following activities: methylase activity, demethylase activity, translation activation activity, translation repression activity, histone modification activity, RNA cleavage activity, or DNA cleavage activity, and
    wherein components (a) and (b) are located on the same or different vectors of the system and wherein the Rt-gRNA and said FnCas protein do not naturally occur together.

2. The vector system according to claim 1, wherein said FnCas protein is a type II Cas protein.

3. The vector system according to claim 1, wherein said scaRNA sequence is fused to said tracrRNA sequence.

4. The vector system according to claim 1, wherein said FnCas protein is codon optimized for expression in a eukaryotic cell.

5. The vector system according to claim 1, wherein said one or more vectors are viral vectors, or wherein said one or more vectors are selected from the group consisting of retroviral, lentiviral, adenoviral, adeno-associated and herpes simplex viral vectors.

6. The vector system according to claim 1, wherein said RNA-targeting guide RNA is designed to direct said FnCas protein to said target RNA.

7. A composition comprising a vector system according to claim 1.

8. A method for modulating synthesis of a protein comprising introducing into a cell containing an RNA molecule encoding said protein, the vector system of claim 1.

9. The method according to claim 8, wherein the synthesis of said protein is suppressed; or the synthesis of said protein is modulated by editing of said RNA molecule encoding said protein or splicing of said RNA molecule encoding said protein.

10. The method according to claim 9, wherein the synthesis of said protein is suppressed by knock-down of said RNA molecule encoding said protein.

11. The method according to claim 10, wherein said RNA-targeting Cas protein is codon optimized for expression in a eukaryotic cell.

12. The method according to claim 11, wherein said one or more vectors are viral vectors, or wherein said one or more vectors are selected from the group consisting of retroviral, lentiviral, adenoviral, adeno-associated and herpes simplex viral vectors.

13. The method according to claim 12, wherein the cell is a eukaryotic cell.

14. The method according to claim 11, wherein the eukaryotic cell is a mammalian or human cell.

15. The composition according to claim 7, wherein one or more amino acid residues of the FnCas protein, other than those amino acid positions in FnCas that are analogous to amino acid positions 534-676 corresponding to a *Streptococcus pyogenes* Cas9 (SpCas9) Rec1 domain at which the one or more heterologous functional domains are positioned are modified.

16. The composition according to claim 15, wherein the modification comprises mutation of one or more, or two or more, or three or more amino acid residues of the FnCas protein.

17. The composition according to claim 16, wherein the one or more,
  or two or more, or three or more mutations are in one or more catalytically active domains of the FnCas protein.

18. The composition according to claim 17, wherein the FnCas protein has reduced or abolished nuclease activity compared with an FnCas protein lacking said mutation(s).

19. The composition according to claim 18, wherein the one or more,
  or two or more mutations are in a catalytically active domain of the FnCas protein comprising a RuvCI, RuvCII or RuvCIII domain.

20. The vector system according to claim 1, wherein the FnCas further comprises one or more heterologous functional domains selected from the group consisting of transcriptional activation domain, transcriptional repression domain and nuclease domain.

21. The vector system according to claim 20, wherein the transcriptional activation domain comprises VP64.

22. The vector system according to claim 20, wherein the transcriptional repression domain comprises a KRAB domain or a SID domain.

23. The vector system according to claim 20, wherein the nuclease domain comprises Fok1.

24. The vector system according to claim 1, wherein the one or more functional domains further have one or more of the following activities: deaminase activity, transcription activation activity, transcription repression activity, transcription release factor activity, nuclease activity, single-strand RNA cleavage activity, double-strand RNA cleavage activity, single-strand DNA cleavage activity, double-strand DNA cleavage activity and nucleic acid binding activity.

25. The composition according to claim 7, wherein the tracrRNA or the scaRNA comprises one or more protein-binding RNA aptamers.

26. The composition according to claim 25, wherein the one or more aptamers is designed to bind a bacteriophage coat protein.

27. The composition according to claim 26, wherein the bacteriophage coat protein is selected from the group consisting of QB, F2, GA, fr, JP501, MS2, M12, R17, BZ13, JP34, JP500, KU1, M11, MX1, TW18, VK, SP, FI, ID2, NL95, TW19, AP205, ¢Cb5, ¢Cb8r, ¢Cb12r, ¢Cb23r, 7s and PRR1.

28. The composition according to claim 7, wherein the tracrRNA is 30 or more, 40 or more or 50 or more nucleotides in length.

29. The composition according to claim 7, wherein the FnCas protein is modified to comprise a PAM sequence specificity which is different from the PAM sequence specificity of the FnCas protein without said further modification.

30. The composition according to claim 29, wherein said modification comprises the introduction of one or more amino acid mutations into the FnCas protein, or by truncation of the FnCas protein, or by deletion and/or insertion of specific amino acids or amino acid sequences into the FnCas protein.

31. The composition according to claim 7, wherein the one or more vectors comprise a plurality of polynucleotide sequences encoding multiple Rt-gRNAs, wherein each Rt-gRNAs is specific for a different target RNA whereby there is multiplexing.

32. A host cell or cell line comprising the composition according to claim 7, or progeny thereof.

33. The host cell or cell line or progeny thereof according to claim 32, which is ex vivo or in vitro, a stem cell or a stem cell line, or a plant cell or a plant cell line.

34. The vector system according to claim 1, wherein the one or more functional domains are associated with an adaptor protein.

35. The vector system according to claim 1, wherein the FnCas protein comprises two or more functional domains.

36. The vector system according to claim 1, wherein the FnCas protein or ortholog, homolog, or fragment thereof, further comprises one or more heterologous thereof, further comprises one or more heterologous functional domains positioned at one or more sites in FnCas that are analogous to amino acid positions 175-306 of a wild type SpCas9 Rec1 domain.

* * * * *